US008134047B2

(12) United States Patent
Stonaker et al.

(10) Patent No.: US 8,134,047 B2
(45) Date of Patent: Mar. 13, 2012

(54) MAIZE PLANTS WITH REDUCED GENE SILENCING

(75) Inventors: Jennifer L. Stonaker, Fremont, CA (US); Christopher J. Hale, El Cerrito, CA (US); Jay B. Hollick, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 301 days.

(21) Appl. No.: 12/400,727

(22) Filed: Mar. 9, 2009

(65) Prior Publication Data

US 2009/0265811 A1 Oct. 22, 2009

Related U.S. Application Data

(60) Provisional application No. 61/034,802, filed on Mar. 7, 2008.

(51) Int. Cl.
*C12N 15/82* (2006.01)
*A01H 5/10* (2006.01)

(52) U.S. Cl. ...... 800/286; 800/285; 800/298; 800/320.1

(58) Field of Classification Search .................. 800/286
See application file for complete search history.

(56) References Cited

U.S. PATENT DOCUMENTS 6,153,741 A * 11/2000 Richards et al. ............ 536/23.6
7,264,970 B2 * 9/2007 Chandler et al. ............. 435/468

OTHER PUBLICATIONS

Lehner et al. How to Use RNA Interference (2004) Briefings in Functional Geomics and Proteomics. 3: 68-83.*
McGinnis, K. M. RNAi for Functional Genomics (2010) Briefings in Functional Genomics 9: 111-117.*
Watson et al. RNA silencing platforms in plants (2005) FEBS Letters 5982-5987.*
Schwab et al. Highly specific gene silencing by artificial microRNAs in *Arabidopsis* (2006) Plant Cell 18: 1121-1133.*
Hale et al. A nocel SNF2 protein maintains trans-generational regualtory states established by paramutation in Maize (2007) 5: e275.*
Alexeev, A. et al. (2003). "Rad54 protein possesses chromatin-remodeling activity stimulated by the Rad51-ssDNA nucleoprotein filament," Nat Struct Biol. 10(3):182-186.
Alleman, M. et al. (2006). "An RNA-dependent RNA polymerase is required for paramutation in maize," Nature 442:295-298.
Auble, DT. et al. (1994). "Mot1, a global repressor of RNA polymerase II transcription, inhibits TBP binding to DNA by an ATP-dependent mechanism," Genes Dev. 8(16):1920-1934.
Bakshi, R. et al. (2006). "Characterization of a human SWI2/SNF2 like protein hINO80: demonstration of catalytic and DNA binding activity," Biochem Biophys Res Commun. 339(1):313-320.
Bercury, SD. et al. (2001). "Molecular analysis of the *doppia* transposable element of maize," Plant Mol Biol 47:341-351.
Blewitt, ME. et al. (2006)."Dynamic reprogramming of DNA methylation at an epigenetically sensitive allele in mice," PLoS Genet 2:e49.
Bourc'his, D. and Bestor, TH. (2002). "Helicase homologues maintain cytosine methylation in plants and mammals," Bioessays 24:297-299.
Brink, RA. (1958). "Paramutation at the *R* locus in maize," Cold Spring Harb Symp Quant Biol 23:379-391.
Brink, RA. (1973). "Paramutation," Annu Rev Genet 7:129-152.
Brzeski, J. and Jerzmanowski, A. (2003). "Deficient in DNA methylation 1 (DDM1) defines a novel family of chromatin-remodeling factors," J Biol Chem 278: 823-828.
Buhler, M. et al. (2006). "Tethering RITS to a nascent transcript initiates RNAi- and heterochromatin-dependent gene silencing," Cell 125:873-886.
Buhler, M. et al. (2007). "RNAi-dependent and -independent RNA turnover mechanisms contribute to heterochromatic gene silencing," Cell 129:707-721.
Cao, X. et al. (2002). "Locus-specific control of asymmetric and CpNpG methylation by the DRM and CMT3 methyltransferase genes," Proc Natl Acad Sci USA 99:16491-16498.
Cao, X. et al. (2002). "Role of the *Arabidopsis* DRM methyltransferases in de novo DNA methylation and gene silencing," Curr Biol 12:1138-1144.
Cao, X. et al. (2003). "Role of the DRM and CMT3 methyltransferases in RNA-directed DNA methylation," Curr Biol 13:2212-2217.
Chan, SW. et al. (2004). "RNA silencing genes control de novo DNA methylation," Science 303:1336.
Chan, SW. et al. (2006). "RNAi, DRD1, and histone methylation actively target developmentally important non-CG DNA methylation in *Arabidopsis*," PLoS Genet 2:e83.
Chandler, VL. et al. (2004). "Chromatin conversations: Mechanisms and implications of paramutation," Nat Rev Genet 5:532-544.
Chandler, VL. (2007) "Paramutation: From maize to mice," Cell 128:641-645.
Cocciolone, SM. et al. (2001). "Tissue-specific patterns of a maize Myb transcription factor are epigenetically regulated," Plant J. 27(5):467-478.
Cone, KC. et al. (1993). "Maize anthocyanin regulatory gene *pl* is a duplicate of *c1* that functions in the plant," Plant Cell 5:1795-1805.
Cone, KC. et al. (1993). "Role of the regulatory gene *pl* in the photocontrol of maize anthocyanin pigmentation," Plant Cell 5:1807-1816.
Dennis, K. et al. (2001). "Lsh, a member of the SNF2 family, is required for genome-wide methylation," Genes Dev 15:2940-2944.
Domanskyi, A. et al. (2006). "Biochemical characterization of androgen receptor-interacting protein 4," Biochem J. 393(Pt 3):789-795.
Dorweiler, JE. et al. (2000). "Mediator of *paramutation1* is required for establishment and maintenance of paramutation at multiple maize loci," Plant Cell 12:2101-2118.
Durr, H. et al. (2006). "Snf2 family ATPases and DExx box helicases: Differences and unifying concepts from high-resolution crystal structures," Nucleic Acids Res 34:4160-4167.
Edgar, RC. (2004) "MUSCLE: Multiple sequence alignment with high accuracy and high throughput," Nucleic Acids Res 32:1792-1797.
Eissenberg, JC. et al. (2006). "Leaving a mark: The many footprints of the elongating RNA polymerase II," Curr Opin Genet Dev 16:184-190.

(Continued)

*Primary Examiner* — Russell Kallis
*Assistant Examiner* — Steven Bernacki
(74) *Attorney, Agent, or Firm* — Morrison & Foerster LLP

(57) ABSTRACT

Maize plants with reduced gene silencing are disclosed.

6 Claims, 22 Drawing Sheets

OTHER PUBLICATIONS

Farris, SD. et al. (2005). "Transcription-induced chromatin remodeling at the c-myc gene involves the local exchange of histone H2A. Z," J Biol Chem 280:25298-25303.
Fedoroff, NV. (1999). "The *Suppressor-mutator* element and the evolutionary riddle of transposons," Genes Cells 4:11-19.
Flaus, A. et al. (2006). "Identification of multiple distinct Snf2 subfamilies with conserved structural motifs," Nucleic Acids Res 34:2887-2905.
Girard. A. et al. (2006). "A germline-specific class of small RNAs binds mammalian Piwi proteins," Nature 442(7099):199-202.
Gross, SM. et al. (2007). "Multiple *trans*-sensing interactions affect meiotically heritable epigenetic states at the maize *pl1* locus," Genetics 176:829-839.
Hale, CJ. et al. (2007). "A novel Snf2 protein maintains trans-generational regulatory states established by paramutation in maize," PLoS Biol. 5(10):e275.
Hartley, JL. et al. (2000). "DNA cloning using in vitro site-specific recombination," Genome Res. 10(11):1788-1795.
Hollick, JB. (1997). "Paramutation and related allelic interactions," Trends Genet 13:302-308.
Hollick, JB. et al. (1995). "Allelic interactions heritably alter the activity of a metastable maize *pl* allele," Genetics 141:709-719.
Hollick, JB. et al. (1998). "Epigenetic allelic states of a maize transcriptional regulatory locus exhibit overdominant gene action," Genetics 150:891-897.
Hollick, JB. et al. (2000). "Paramutation alters regulatory control of the maize *pl* locus," Genetics 154:1827-1838.
Hollick, JB. et al. (2001). "Genetic factors required to maintain repression of a paramutagenic maize *pl1* allele," Genetics 157:369-378.
Hollick, JB. et al. (2005). "*Rmr6* maintains meiotic inheritance of paramutant states in *Zea mays*," Genetics 171:725-740.
Huettel, B. et al. (2006), "Endogenous targets of RNA-directed DNA methylation and Pol IV in *Arabidopsis*," EMBO J 25:2828-2836.
Irvine, DV. et al. (2006). "Argonaute slicing is required for heterochromatic silencing and spreading," Science 313:1134-1137.
Jeddeloh, JA. et al. (1999). "Maintenance of genomic methylation requires a SWI2/SNF2-like protein," Nat Genet 22:94-97.
Jones, DT. (1999). "GenTHREADER: An efficient and reliable protein fold recognition method for genomic sequences," J Mol Biol 287:797-815.
Kanno, T. et al. (2004), "Involvement of putative SNF2 chromatin remodeling protein DRD1 in RNA-directed DNA methylation," Curr Biol 14:801-805.
Kanno, T. et al. (2005). "A SNF2-like protein facilitates dynamic control of DNA methylation," EMBO Rep 6:649-655.
Karimi, M. et al. (2002). "GATEWAY vectors for Agrobacterium-mediated plant transformation," Trends Plant Sci. 7(5):193-195.
Kasschau, KD. et al. (2007), "Genome-wide profiling and analysis of *Arabidopsis* siRNAs," PLoS Biol 5:e57.
Kermicle, JL. et al. (1995). "Organization of paramutagenicity in *R-stippled* maize," Genetics 141:361-372.
Kinoshita, T. et al. (2004). "One-way control of FWA imprinting in *Arabidopsis* endosperm by DNA methylation," Science 303:521-523.
Knauert, MP. and Glazer, PM. (2001). "Triplex forming oligonucleotides: sequence-specific tools for gene targeting," Hum Mol Genet. 10(20):2243-2251.
Konieczny, A. and Ausubel, FM. (1993). "A procedure for mapping *Arabidopsis* mutations using co-dominant ecotype-specific PCR-based markers," Plant J 4:403-410.
Laurent, BC. et al. (1993). "The yeast SNF2/SWI2 protein has DNA-stimulated ATPase activity required for transcriptional activation," Genes Dev 7(4):583-91.
Lawrence, CJ. et al. (2007). "Maize GDB's new data types, resources and activities," Nucleic Acids Res 35:D895-D900.
Lisch, D. et al. (2002). "A mutation that prevents paramutation in maize also reverses *Mutator* transposon methylation and silencing," Proc Natl Acad Sci USA 99:6130-6135.
Liu, M. et al. (1998) "A human RNA polymerase II transcription termination factor is a SWI2/SNF2 family member," J Biol Chem 273(40):25541-25544.
Lu, C. et al. (2006). "MicroRNAs and other small RNAs enriched in the *Arabidopsis* RNA-dependent RNA polymerase-2 mutant," Genome Res 16(10):1276-88.
Martienssen, R. et al. (1990). "Somatically heritable switches in the DNA modification of mu transposable elements monitored with a suppressible mutant in maize," Genes Dev 4:331-343.
Mathieu, O. and Bender, J. (2004). "RNA-directed DNA methylation," J Cell Sci 117:4881-4888.
McClintock, B. (1951). "Chromosome organization and genic expression," Cold Spring Harb Symp Quant Biol 16:13-47.
McGinnis, KM. et al. (2006). "Transcriptionally silenced transgenes in maize are activated by three mutations defective in paramutation," Genetics 173:1637-1647.
Miki, D. et al. (2004). "Simple RNAi vectors for stable and transient suppression of gene function in rice," Plant Cell Physiol 45(4):490-495.
Owen-Hughes, T. et al. (1999). "Analysis of nucleosome disruption by ATP-driven chromatin remodeling complexes," Methods Mol Biol. 119:319-331.
Panavas, T. et al. (1999). The structure and paramutagenicity of the *R-marbled* haplotype of *Zea mays*, Genetics 153:979-991.
Parkinson, SE. et al. (2007). "Maize sex determination and abaxial leaf fates are canalized by a factor that maintains repressed epigenetic states," Dev Biol. 308(2):462-473.
Patterson, GI. et al. (1993). "Paramutation, an allelic interaction, is associated with a stable and heritable reduction of transcription of the maize *b* regulatory gene," Genetics 135:881-894.
Pontes, O. et al. (2006). "The *Arabidopsis* chromatin-modifying nuclear siRNA pathway involves a nucleolar RNA processing center," Cell 126:79-92.
Raabe, EH. et al. (2001). "An SNF2 factor involved in mammalian development and cellular proliferation," Dev Dyn 221:92-105.
Rassoulzadegan, M. et al. (2006). "RNA-mediated non-mendelian inheritance of an epigenetic change in the mouse," Nature 441:469-474.
Rohila, JS. et al. (2006). "Protein-protein interactions of tandem affinity purification-tagged protein kinases in rice," Plant J 46(1):1-13.
Sainz, MB. et al. (1997). "Evidence for direct activation of an anthocyanin promoter by the maize C1 protein and comparison of DNA binding by related Myb domain proteins," Plant Cell 9:611-625.
Shaked, H. et al. (2006). "Involvement of the *Arabidopsis* SWI2/SNF2 chromatin remodeling gene family in DNA damage response and recombination," Genetics 173:985-994.
Shevchenko, Y. et al. (2002). "Systematic sequencing of cDNA clones using the transposon Tn5," Nucleic Acids Res. 30(11):2469-2477.
Shuman S. (1994). "Novel approach to molecular cloning and polynucleotide synthesis using vaccinia DNA topoisomerase," J Biol Chem 269(51):32678-32684.
Slotkin, RK. et al. (2005). "Heritable transposon silencing initiated by a naturally occurring transposon inverted duplication," Nat Genet 37:641-644.
Smith, CL. and Peterson, CL. (2005). "ATP-dependent chromatin remodeling," Curr Top Dev Biol. 65:115-148.
Smith, LM. et al. (2007). "An SNF2 protein associated with nuclear RNA silencing and the spread of a silencing signal between cells in *Arabidopsis*," Plant Cell 19:1507-1521.
Stam, M. et al. (2002). "The regulatory regions required for *B'* paramutation and expression are located far upstream of the maize *b1* transcribed sequences," Genetics 162:917-930.
Swigonova, Z. et al. (2004). "On the tetraploid origin of the maize genome," Comp Funct Genomics 5(3):281-284.
Thomä, NH. et al. (2005). "Structure of the SWI2/SNF2 chromatin-remodeling domain of eukaryotic Rad54," Nat Struct Mol Biol 12(4):350-356.
Walker, EL. et al. (1995), "Transposon-mediated chromosomal rearrangements and gene duplications in the formation of the maize *R-r* complex," EMBO J 14:2350-2363.

Whitehouse, I. et al. (2003). "Evidence for DNA translocation by the ISWI chromatin-remodeling enzyme," Mol Cell Biol 23(6):1935-1945.
Woodhouse, MR. et al. (2006). "Initiation, establishment, and maintenance of heritable *MuDR* transposon silencing in maize are mediated by distinct factors," PLoS Biol 4:e339.
Xie, Z. et al. (2004). "Genetic and functional diversification of small RNA pathways in plants," PLoS Biol 2:642-652.
Zilberman, D. et al. (2003). "ARGONAUTE4 control of locus-specific siRNA accumulation and DNA and histone methylation," Science 299:716-719.
Zilberman, D. et al. (2004). "Role of *Arabidopsis* ARGONAUTE4 in RNA-directed DNA methylation triggered by inverted repeats," Curr Biol 14:1214-1220.

* cited by examiner

```
                             20                  40                  60
RMR1        HQREAFEFMWTNLVGDIRLDEIKHGA------------------------KPDVVGGCVI   36 SEQ ID NO 1
At1g05490   HQQEGFEFIWKNLAGTIMLNELKDFE------------------------NSDETGGCIM   36 SEQ ID NO 2
At3g24340   HQQEGFEFIWKNLAGTTKINELNSVGV-------------------------KGSGGCII   35 SEQ ID NO 3
Os5g32610   HQREAFEFMWTNLVGDIRLNEIKHGA------------------------KPDVVGGCVI   36 SEQ ID NO 4
AtCLSY1     HQKKAFEFLWKNLAGSVVPAMMDPSS--------------------------DKIGGCVV   34 SEQ ID NO 5
At5g20420   HQRRAFEFLWRNVAGSVEPSLMDPTS--------------------------GNIGGCVI   34 SEQ ID NO 6
Os7g49210   HQRKALDFLWKNLAGSIQVEGMDNSN--------------------------VSTGGCVI   34 SEQ ID NO 7
Os7g25390   HQLEGFSFLVKNLVG-------------------------------------DKPGGCIL   23 SEQ ID NO 8
CHR156      HQVEGFNFLVKNLIG---------------------------------------------   15 SEQ ID NO 9
At2g21450   HQTEGFRFLCNNLAA-------------------------------------DEPGGCIL   23 SEQ ID NO 10
AtDRD1      HQIEGFQFLCSNLVA-------------------------------------DDPGGCIL   23 SEQ ID NO 11
CHR127      ------------------------------------------------------------    - SEQ ID NO 12
ScRAD54     HQVEGVRFLYRCVTGLVMKDYLEAEAFNTSSEDPLKSDEKALTESQKTEQNNRGAYGCIM   60 SEQ ID NO 13
AtDDM1      YQLKGVKWLISLW--------------------------------------QNGLNG-IL   21 SEQ ID NO 14
ScSNF2      YQIKGLQWMVSLF--------------------------------------NNHLNG-IL   21 SEQ ID NO 15

                             80                 100                 120
RMR1        CHAPGTGKTRLAIVFIQTYMK-VFEDCRPV-----IIAPRGMLFAWDEEFKKWNV-DVEF   89
At1g05490   SHAPGTGKTRLTIIFLQAYLQ-CFEDCKPV-----IIAPASLLLTWAEEFKKWNI-SIPF   89
At3g24340   SHKAGTGKTRLTVVFLQSYLK-RFENSHPM-----VLAPATLMRTWEDEVRKWNV-NIPF   88
Os5g32610   CHAPGTGKTRLAIVFIQTYMK-VFEDCRPV-----IIAPRGMLFAWEQEFKKWNV-NVEF   89
AtCLSY1     SHTPGAGKTFLIIAFLASYLK-IFPGKRPL-----VLAPKTTLYTWYKEFIKWEI-PVPV   87
At5g20420   SHSPGAGKTFLIIAFLTSYLK-LFPGKRPL-----VLAPKTTLYTWYKEFIKWEI-PVPV   87
Os7g49210   AHTPGSGKTLLLISFLVSYMK-AHPRSRPL-----VLTPKAAIHTWKREFEKWGI-SLPL   87
Os7g25390   AHAPGSGKTFMLISFIQSFLA-KYPSARPL-----VVLPKGILGTWKREFQRWQVEDIPL   77
CHR156      -DKPG-GKTFLLISFIQSFMA-RYPSARPL-----VVLPKGILVIWKKEIQRWQVQDIPV   67
At2g21450   AHAPGSGKTFLLISFLQSFMA-MDPQARPL-----VVLPKGIIESWKREFTLWEVEKIPL   77
AtDRD1      AHAPGSGKTFMILSFMQSFLA-KYPQAKPL-----VVLPKGILPTWKKEFVRWQVEDIPL   77
CHR127      ------------------------------------------------------------    -
ScRAD54     ADEMGLGKTLQCIALMWTLLR-QGPQGKRLIDKCIIVCPSSLVNNWANELIKW----LGP  115
AtDDM1      ADQMGLGKTIQTIGFLSHLKG-NGLDGPYL-----VIAPLSTLSNWFNEIARF----TP-   70
ScSNF2      ADEMGLGKTIQTISLLTYLYEMKNIRGPYL-----VIVPLSTLSNWSSEFAKW----AP-   71

                            140                 160                 180
RMR1        HILN------------TTDYTGKEDREICKLI---------KKEHRTEKLTRLVKLLSWN  128
At1g05490   HNLS------------SLDFTGKENSAALGLL------MQKNATARSNNEIRMVKLYSWI  131
At3g24340   YNMN------------SLQLSGYEDAEAVSRL----------EGNRHHNSIRMVKLVSWW  126
Os5g32610   HIMN------------TTDYSCKEDRDICRLI---------KKEHRTEKLTRLVKLFSWN  128
AtCLSY1     HLLHGRRTYCMSKE-KTIQFEGIPK----------------PSQDVMHVLDCLDKLQKWH  130
At5g20420   HLIHGRRTYCTFKQNKTVQFNGVPK----------------PSRDVMHVLDCLEKLQKWH  131
Os7g49210   HVFH------------HANRSGKPLGAMDSKLRSLLNNFHRPTWTNMRLMDSLDKLFKWH  135
Os7g25390   YDFY------------SVKADKRTE--------------------------QLEVLKSWE   99
CHR156      YDFY------------SVKVEKRVE--------------------------QLQILKSWE   89
At2g21450   LDFY------------SVKAESRKQ--------------------------QLKVLGQWI   99
AtDRD1      LDFY------------SAKAENRAQ--------------------------QLSILKQWM   99
CHR127      ------------------------------------------------------------    -
ScRAD54     NTLT------------PLAVDGKKS------------------SMGGGNTTVSQALHAWA  145
AtDDM1      -SIN------------AIIYHGDKN--------------------------QRDELRRKH   91
ScSNF2      -TLR------------TISFKGSPN--------------------------E----RKAK   88
```

Figure 8A

```
                                   200                            220                          240
RMR1        KGHG------IIGISYGLYTKLTSEKPGC------------TEENKVRSILLDNP-GLLV   169
At1g05490   KSKS------ILGISVNLYEKLAGVKDEDKKTKMVREVKPDKELDDIREILMGRP-GLLV   184
At3g24340   KQKS------ILGISYPLYEKLAANKNT-------------EGMQVFRRMLVELP-GLLV   166
Os5g32610   RGHG------VLGISYGLYMKLTSEKVGC------------TGENKVRTILLENP-GLLV   169
AtCLSY1     AQPS------VLVMGYTSFLTLMREDSKF------------AHRKYMAKVLRESP-GLLV   171
At5g20420   AHPS------VLVMGYTSFTTLMREDSKF------------AHRKYMAKVLRESP-GLLV   172
Os7g49210   AHPS------VLLMTYSSFLGMTKQDSKVRN----------RYREFIAFVLMNNP-GLLI   178
Os7g25390   ARMS------ILFLGYKQFSRIICGDGDG------------NIAAACRDRILMVP-NLLI   140
CHR156      DKMG------ILFLGYKQFSTIVTDDGGS------------KVTAACRDRLLKVP-NLLI   130
At2g21450   KERS------ILFLGYQQFTRIICDDNFE------------AASEDCKLILLEKP-TLLI   140
AtDRD1      EKKS------ILFLGYQQFSTIVCDDT--------------TDSLSCQEILLKVP-SILI   138
CHR127      ------------------------------------------------------------     -
ScRAD54     QAQGRNIVKPVLIISYE-----------------------TLRRNVDQLKNCNV-GLMI    180
AtDDM1      MPKTVGPKFPIVITSYE-----------------------VAMNDAKRILRHYPWKYVV    127
ScSNF2      QAKIRAGEFDVVLTTYE-----------------------YIIKE-RALLSKVKWVHMI    123

                                   260                            280                          300
RMR1        LDEGHTPRNERSVIWKTLG-NVKTEKRIILSGTPFQNNFLELYNILCLVRPRFGEMFLTK   228
At1g05490   LDEAHTPRNQRSCIWKTLS-KVETQKRILLSGTPFQNNFLELCNVLGLARPKYLERLTST   243
At3g24340   LDEGHTPRNQSSLIWKVLT-EVRTEKRIFLSGTLFQNNFKELSNVLCLARPADKD-----   220
Os5g32610   LDEGHTPRNERSVIWKTLG-KVKTEKRIILSGTPFQNNFLELYNILCLVRPRFGEMFLTK   228
AtCLSY1     LDEGHNPRSTKSRLRKALM-KVDTDLRILLSGTLFQNNFCEYFNTLCLARPKFVHEVLVE   230
At5g20420   LDEGHNPRSTKSRLRKALM-KVGTDLRILLSGTLFQNNFCEYFNTLCLARPKFIHEVLME   231
Os7g49210   LDEGHNPRSNKSKLRKLLM-KVKTEFRILLSGTAFQNNFEEYFNTLCLARPRFIGDIMSE   237
Os7g25390   LDEGHTPRNRETDVLASLK-RVQTPRKVVLSGTLFQNHVSEVFNILDLVRPKFLKMESSR   199
CHR156      LDEGHTPRNKETDVLESLS-RVETPRKVVLSGTLFQNHVEEVFNILNLVRPKFLRMESSR   189
At2g21450   LDEGHTSRNKETYVLSSLA-RVKTRRKVVLTGTLFQNNVEEVFNILDLVRPKFLKRPGTR   199
AtDRD1      LDEGHTPRNEDTNVLQSLA-QVQTPRKVVLSGTLYQNHVKEVFNILNLVRPKFLKLDTSK   197
CHR127      ------------------------------------------------------------     -
ScRAD54     ADEGHRLKNGDSLTFTALD-SISCPRRVILSGTPIQNDLSEYFALLSFSNPGLLGS----   235
AtDDM1      IDEGHRLKNHKCKLLRELK-HLKMDNKLLLTGTPLQNNLSELWSLLNFILPDIFTS----   182
ScSNF2      IDEGHRMKNAQSKLSLTLNTHYHADYRLILTGTPLQNNLPELWALLNFVLPKIFNS----   179

                                   320                            340                          360
RMR1        ------------SRVGRRHYVSKKQKDKFSDKYEKGVWASLTSNVTDDNAEKVRSILKPF   276
At1g05490   ------------LKKSGMTVTKRGKKNLGNEINNRGI-------------EEIKAVMLPF   278
At3g24340   ------------TISSRIHELSKCSQEGEHGRVNEEN-----------RIVDLKAMIAHF   257
Os5g32610   ------------TRVGRRHCVSKKQRDKFSDKYEKGVWASLTSNVTDDNAEKVRSILKPF   276
AtCLSY1     LDKKFQTNQ---AEQKAPHLLENRARKFFLDIIAKKI-DTKVGDERLQGLNMLRNMTSGF   286
At5g20420   LDQKFKTNH---GVNKAPHLLENRARKLFLDIIAKKI-DASVGDERLQGLNMLKNMTNGF   287
Os7g49210   LVPERKRET---VGRRAKH-QEAVARRAFVEKVGQKI-ESDNKHIRSDGISLLNKLTRGF   292
Os7g25390   PIARRIMSQ---VAISGIRSLKGVHDSAFTESVEDTLLNDDNFTRKSHVIRSLREITKDV   256
CHR156      PIARRIMSQ---VEIFGRS-SKGLADGAFTEAVEGTLLNDENFKRKVHVIRGLREITRDV   245
At2g21450   EIVSRIMSKAEIPRGKQVNQSSSSIEGTFFAAVELTLQRSTNFSAKASLIKDLREMTRNI   259
AtDRD1      SAVKRILAYTPCDVRGRLTGSNSDMASMFNETVEHTLQKSEDFTVKIKVIQDLREMTKKV   257
CHR127      ------------------------------------------------------------     -
ScRAD54     ------------RAEFRKNFENPILRGRDADATDKEI------TKGEAQLQKLSTIVSKF   277
AtDDM1      ------------HDEFESWFDFSEKNKNEATK-EEEE------KRRAQVVSKLHGILRPF   223
ScSNF2      ------------VKSFDEWFNTPFANTGGQDKIELSE------EETLLVIRRLHKVLRPF   221
```

Figure 8B

```
                                     380                           400                           420
RMR1          VHIHNGNILR---TLPGLRESVLILKPLPLQKSILKKVENIG---S-------GNNFEHE   323
At1g05490     VHVHKGSILQS--SLPGLRECVVVLNPPELQRRVLESIEVTHNRKT-------KNVFETE   329
At3g24340     VHVHEGTILQE--SLPGLRDCVVVLNPPFQQKKILDRIDT-----S-------QNTFEFE   303
Os5g32610     VHIHNGTILR---TLPGLRECVLVLKPLPLQKSILRKVENVG---S-------GNNFEHE   323
AtCLSY1       IDNYEGSGSGSGDVLPGLQIYTLLLNSTDVQHKSLTKLQNIMSTYH-------GYPLELE   339
At5g20420     IDNYEGSGSGSGDALPGLQIYTLVLNSTDIQHKILTKLQDVIKTYF-------GYPLEVE   340
Os7g49210     IDSFEGAKLI---NLPGIHVYTVFLKPTDIQEEMLAKVTMPKLGSS-------RFPLEVE   342
Os7g25390     LHYYKGDILD---ELPGLVDFSVFLKLSTKQKEIVHKIEA-------------YEKFKRS   300
CHR156        LHYYKGAILD---ELPGLVDFSVFLKLTPKQKDIVHKIEM-------------HDRFKRS   289
At2g21450     LHYHKADFSG---LLPGLSEFTVMLNLSSIQRDEVKGLRK-------------MELFKQI   303
AtDRD1        LHYYKGDFLD---ELPGLADFTVVLNLSPKQLNEVKKLRR-----E-------KRKFKVS   302
CHR127        LHYYKGDILD---ELPGLVDFSVFLKLTPKQKDIVYKIEA-------------HDRGGGF    44
ScRAD54       IIRRTNDILAK--YLPCKYEHVIFVNLKPLQNELYNKLIKSREVKKVVKGVGGSQPLRAI   335
AtDDM1        ILRRMKCDVEL--SLPRKKEIIMYATMTDHQKKFQEHLVNNTLEAH-------LGENAIR   274
ScSNF2        LLRRLKKDVEK--ELPDKVEKVVKCKMSALQQIMYQQMLKYRRLFI-------GDQNNKK   272

                                     440                           460                           480
RMR1          YVISLASTHPSLVTAINMSEEEA--SLIDKP--------MLAKVRSNPYEGVKTRFVIEV   373
At1g05490     HKLSLVSVHPSLVSRCKISEKER--LSIDEA-----LLAQLKKVRLDPNQSVKTRFLMEF   382
At3g24340     HKLSAVSVHPSLYLCCNPTKKED--LVIGPA-----TLGTLKRLRLKYEEGVKTKFLIDF   356
Os5g32610     YVISLASTHPSLVNAINMTEEEA--SLIDKP--------MLERLRSNPYEGVKTRFVMEV   373
AtCLSY1       LLITLAAIHPWLVKTTTCCA-----KFFNPQ-----ELLEIEKLKHDAKKGSKVMFVLNL   389
At5g20420     LQITLAAIHPWLVTSSNCCT-----KFFNPQ-----ELSEIGKLKHDAKKGSKVMFVLNL   390
Os7g49210     LLITIGSIHPWLIKTTKAVS-----TFFSPA-----EVKKVERYKRDFAAGCKAKFVIDL   392
Os7g25390     AVGTALYIHPCLSEISEGDAADRATNLTDAT-----VDSLIESL--IIKDGVKAKFFFNL   353
CHR156        AVGSALYIHPCLSGLSEVNAENRAHTLRDDS-----VDSLMDSL--NVRDGVKANFFMNL   342
At2g21450     SLGAALYIHPKLKSFLEENPSNGEKGFSDNNTTVMKLDKMLKKL--NVRDGVKMKFFLNL   361
AtDRD1        AVGSAIYLHPKLKVFSDKSD-----DVSDTT-----MDEMVEKL--DLNEGVKAKFFLNL   350
CHR127        FFGSALYIHPCVSELSEVNAEHRANTFRDDL-----VDSLVDSL--TVRDGVKANFFMNI    97
ScRAD54       GILKKLCNHPNLLNFEDEFDDEDDLELPDDY-----NMPGSKARDVQTKYSAKFSILERF   390
AtDDM1        GQGWKGKLNNLVIQLRKNCNHP---DLLQGQIDGSYLYPPVEEI---VGQCGKFRLLERL   328
ScSNF2        MVGLRGFNNQ-IMQLKKICNHPFVFEEVEDQ-----INPTRETNDDIWRVAGKFELLDRI   326

                                     500                           520                           540
RMR1          VRLSEA-LREKVLIFSQFIQPLELIKEHLRKFFKWREGKEILQMDGKILPRYRQASIEAF   432
At1g05490     VELCEV-IKEKVLVFSQYIDPLKLIMKHLVSRFKWNPGEEVLYMHGKLEQKQRQTLINEF   441
At3g24340     IRISGT-VKEKVLVYSQYIDTLKLIMEQLIAECDWTEGEQILLMHGKVEQRDRQHMIDNF   415
Os5g32610     VRLCEA-LKEKVLIFSQFIQPLELIKEHLRKIFKWREGKEILQMDGKILPRYRQNSIEVF   432
AtCLSY1       VFRVV--KREKILIFCHNIAPIRLFLELFENVFRWKRGRELLTLTGDLELFERGRVIDKF   447
At5g20420     IFRVV--KREKILIFCHNIAPIRMFTELFENIFRWQRGREILTLTGDLELFERGRVIDKF   448
Os7g49210     LHKSSF-RGERVLIFCHNVSPITFLVKLIEMVFGWRLGEEVLVLQGDQELPVRSDVMDKF   451
Os7g25390     LSLANS-AGEKLLAFSQYILPMKFLERLLVKRLGWHVGKEIFMISGDTSADDREVAMDQF   412
CHR156        LSLANS-AGEKVLAFSQYILPMTFFERLLVKKKGWHVGREIFMISGDTSQEDREAAVDRF   401
At2g21450     LALCES-TGEKLLVFSQYIVPIKTLERLMSSMKGWRLGKEMFTITGDSSNEQREWSMERF   420
AtDRD1        INLCDS-AGEKLLVFSQYLIPLKFLERLAALAKGWKLGKEVFVLTGNTSSEQREWSMETF   409
CHR127        LSLANS-AGEKVLAFSQYISPMIFFERLLVKKKGWHVGKEIFMISGDTSQEDRELATDHF   156
ScRAD54       LHKIKTESDDKIVLISNYTQTLDLIEKMCR-----YKHYSAVRLDGTMSINKRQKLVDRF   445
AtDDM1        LVRLFA-NNHKVLIFSQWTKLLDIMDYYFS-----EKGFEVCRIDGSVKLDERRRQIKDF   382
ScSNF2        LPKLKA-TGHRVLIFFQMTQIMDIMEDFLR-----YINIKYLRLDGHTKSDERSELLRLF   380

                                     560                           580
RMR1          N-NPNNDSRVLLASTRACCEGISLTGASRIVLLDVVWNPAVGRQAISRAFRIGQ   485
At1g05490     N-DPKSKAKVFLASTKACSEGISLVGASRVILLDVVWNPAVERQAISRAYRIGQ   494
At3g24340     N-KPDSGSKVLLASTKACSEGISLVGASRVVILDVVWNPSVESQAISRAFRIGQ   468
Os5g32610     N-NPDSDARVLLASTRACCEGISLTGASRVVLLDVVWNPAVGRQAISRAFRIGQ   485
AtCLSY1       E-EPGGQSRVLLASITACAEGISLTAASRVIMLDSEWNPSKTKQAIARAFRPGQ   500
At5g20420     E-EPGNPSRVLLASITACAEGISLTAASRVIMLDSEWNPSKTKQAIARAFRPGQ   501
Os7g49210     NGDSAGKRKVLIASTTACAEGISLTGASRLVMLDSEWNHSKTRQAIARAFRRGQ   505
Os7g25390     N-N-SADAKVLFGSIKACGEGISLVGASRVIILDVHLNPSVTRQAIGRAFRPGQ   464
CHR156        N-S-SADAKVLFGSIRACGEGISLVGASRVVILDVHLNPSVTRQAIGRAFRPGQ   453
At2g21450     N-N-SLEAKVFFGSIKACGEGISLVGASRVLILDVHLNPSVTQQAVARAYRPGQ   472
AtDRD1        N-S-SPDAKIFFGSIKACGEGISLVGASRILILDVPLNPSVTRQAIGRAFRPGQ   461
CHR127        N-N-SADAKVMFGSIKACGEGISLVGASRAVILDVHLNPSVTRQAIGRAFRPGQ   208
ScRAD54       N-DPEGQEFIFLLSSKAGGCGINLIGANRLILMDPDWNPAADQQALARVWRDGQ   498
AtDDM1        S-DEKSSCSIFLLSTRAGGLGINLTAADTCILYDSDWNPQMDLQAMDRCHRIGQ   435
ScSNF2        N-APDSEYLCFILSTRAGGLGLNLQTADTVIIFDTDWNPHQDLQAQDRAHRIGQ   433
```

Figure 8C

A
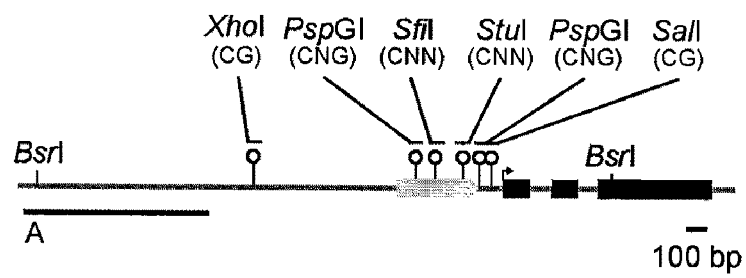
B
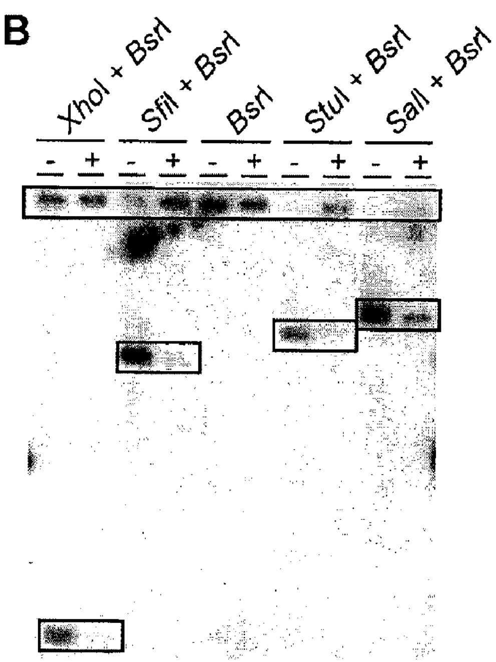
C
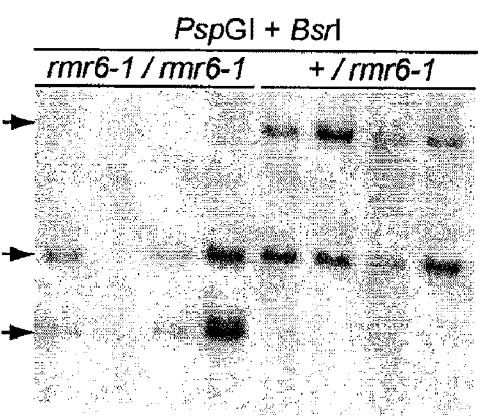
Figure 10

A
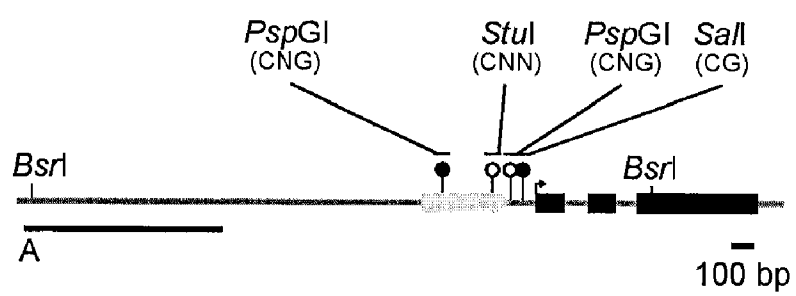
B
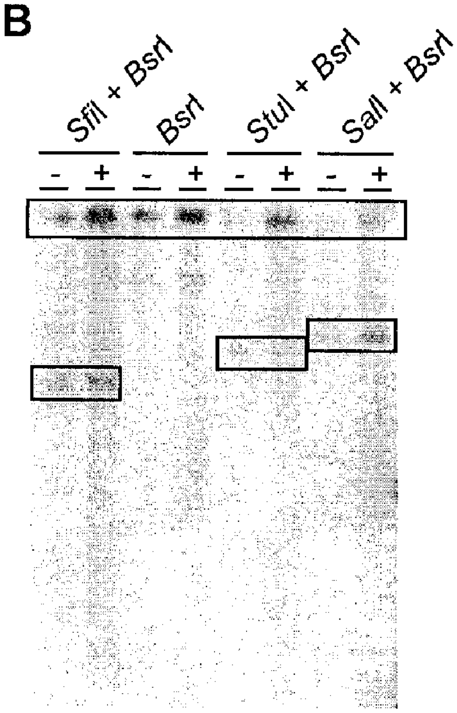
C
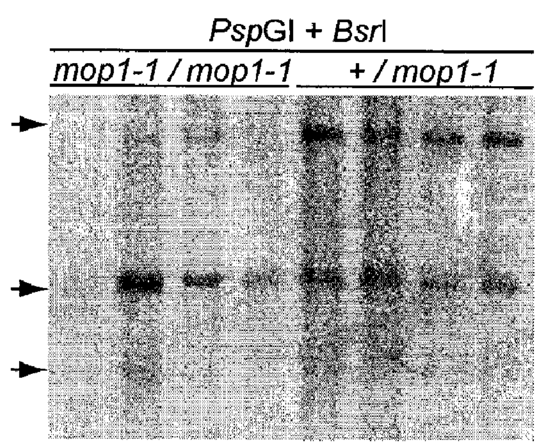
Figure 11

MAIZE PLANTS WITH REDUCED GENE SILENCING

RELATED APPLICATION

This application claims the benefit of U.S. Provisional Application No. 61/034,802, filed Mar. 7, 2008, which is hereby incorporated by reference in its entirety.

STATEMENT AS TO RIGHTS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of Grant No: CSREES-NRI-CGP-2005-35301-15891 awarded by the Department of Agriculture.

FIELD

The field generally relates to gene silencing in plants.

BACKGROUND

The goal of *Zea mays* L. (corn) breeding is to combine various desirable traits in a single variety/hybrid. Such desirable traits include greater yield, better stalks, better roots, resistance to pesticides, pests and disease, tolerance to heat and drought, reduced time to crop maturity, better agronomic quality, higher nutritional value, and uniformity in germination times, stand establishment, growth rate, maturity and fruit size.

Modern molecular biology and transgenic technologies (genetic engineering) have greatly accelerated the introduction of new genes and, hence, new traits into corn lines. While useful, genetic engineering is hampered by transgene silencing problems. Transgene silencing is a little understood process by which genes introduced by genetic engineering are silenced or turned off. As such, transgene silencing is a major impediment to the use of genetic engineering for corn improvement. At present, the solution to transgene silencing is to search through a large number of transgenic events for transgene loci that are active and stable. This is a painstaking and laborious process, which greatly increases the cost of corn breeding using genetic engineering techniques.

In addition to transgene silencing, there are other examples of gene silencing that are variable, unstable, but heritable. In corn these include the cycling of transposable elements between active and inactive states and paramutation, gene silencing that occurs through interactions between specific alleles of a gene. The mechanism of silencing is not understood in any case, but current hypotheses invoke heritable alterations to chromatin structure.

Although mutants are known in corn that can prevent or reverse gene silencing (U.S. Pat. No. 7,264,970), the molecular identity of these factors remains unknown. There thus remains a need to identify the molecular identity of these factors. There is also a need to reduce or mitigate gene silencing in transgenic plants and to reduce inbreeding depression during plant breeding.

SUMMARY

In order to meet these needs the present invention provides a method for reducing or mitigating gene silencing of a transgene by providing a transgenic plant with a transgene and introducing a recombinant nucleic acid to the transgenic plant, in which the recombinant nucleic acid includes a nucleic acid in an antisense orientation in which the sense orientation of the nucleic acid encodes a polypeptide selected from the group consisting of SEQ ID NOs 1-15, and in which the level of expression of the transgene is increased relative to the level of expression of the transgene in a transgenic plant that does not contain the recombinant nucleic acid.

The present invention is further directed to a method for reducing or mitigating gene silencing of a transgene by providing a transgenic plant with a transgene and introducing a recombinant nucleic acid to the transgenic plant, in which the recombinant nucleic acid includes an RNA interference (RNAi) construct including at least a fragment of 20 contiguous nucleotides of a nucleic acid that encodes a polypeptide including but not limited to SEQ ID NOs 1-15 and in which the level of expression of the transgene is increased relative to the level of expression of the transgene in a transgenic plant that does not contain the recombinant nucleic acid.

The methods may further include the step of screening the resulting plants for reduced gene silencing relative to the plant that does not contain the recombinant nucleic acid.

The present invention is further directed to a transgenic plant comprising a recombinant nucleic acid including a nucleic acid in an antisense orientation in which the sense orientation of the nucleic acid encodes a sequence selected from the group consisting of SEQ ID NOs 1-15.

The present invention is further directed to a transgenic plant comprising a recombinant nucleic acid including an RNA interference (RNAi) construct including at least a fragment of 20 contiguous nucleotides of a nucleic acid that encodes a polypeptide selected from the group consisting of SEQ ID NOs 1-15.

The present invention is further directed to seeds from the transgenic plants described above.

The present invention further describes a method for reducing or mitigating inbreeding depression in a plant by providing a plant and introducing a recombinant nucleic acid to the plant, in which the recombinant nucleic acid includes a nucleic acid in an antisense orientation in which the sense orientation of the nucleic acid encodes a polypeptide including but not limited to SEQ ID NOs 1-15, and in which the level of inbreeding depression is reduced relative to the level of inbreeding depression in a plant that does not contain the recombinant nucleic acid.

The present invention is further directed to a method for reducing or mitigating inbreeding depression in a plant by providing a plant and introducing a recombinant nucleic acid to the plant, in which the recombinant nucleic acid comprises an RNA interference (RNAi) construct including at least a fragment of 20 contiguous nucleotides of a nucleic acid that encodes a polypeptide selected from the group consisting of SEQ ID NOs 1-15, and in which the level of inbreeding depression is reduced relative to the level of inbreeding depression in a plant that does not contain the recombinant nucleic acid.

The methods may further include the step of screening the resulting plants for reduced inbreeding depression relative to the plant without the recombinant nucleic acid.

Expression between rmr1 mutants and heterozygous siblings. pl1 RNA levels increase significantly in rmr1 mutants, while transcription rates of paramutant alleles are unaffected.

(A) The relative mean transcription rates from four independent sets of +/rmr1-3 (open) and rmr1-3/rmr1-3 (filled) siblings (±standard error of the mean) at the indicated loci.

(B) RNase protection analysis comparing pl1 and actin1 RNA levels in the same individual plants and tissues used for in vitro transcription analysis.

(C) Quantification of relative pl1 RNA levels from analyses as represented in (B).

Figure 2:
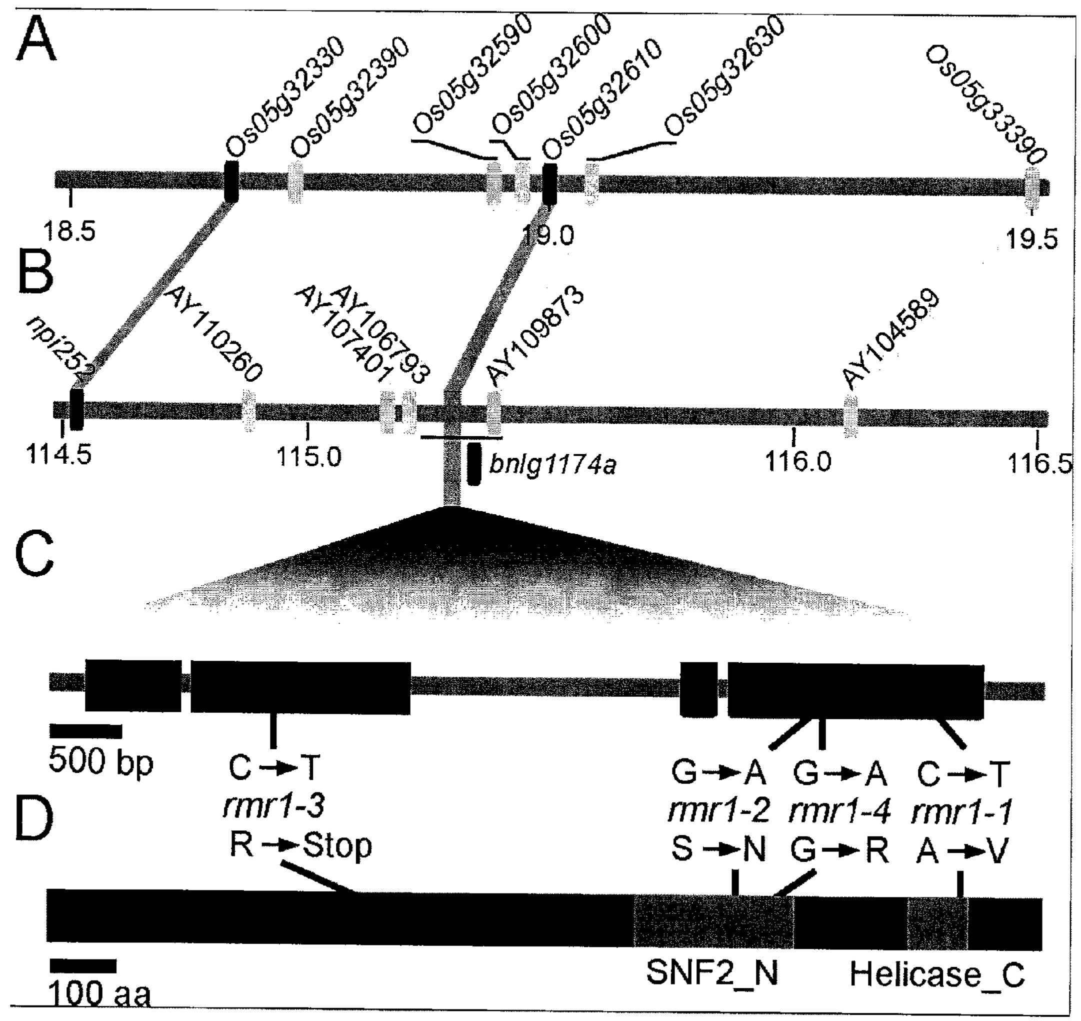

FIG. 2: Map-Based Cloning of rmr1

(A and B) Rice Chromosome 5 (http://rice.tigr.org/) (A) and maize Chromosome 6 (B) (2005 FPC map, contig 285; http://www.genome.arizona.edu/fpc/maize/) with synteny of annotated rice loci and orthologous maize markers (gray boxes) highlighted. Black boxes indicate the rice rmr1 ortholog, Os05g32610, and the SSLP marker npi252. Neither rmr1 nor SSLP marker bnlg1174a are represented on the FPC map, though both can be amplified from a BAC (c0007N19), identified by GenBank ID AY109873, which maps to the region identified by the black line.

(C) Gene structure of rmr1 with exons in black; EMS-derived mutations are noted.

(D) Gray boxes highlight conserved Pfam SNF2_N (E-value=$1.3\times10^{-8}$; amino acids 851 to 1214) and Helicase_C (E-value=$1.1\times10^{-11}$; amino acids 1255 to 1334) profiles in the RMR1 protein. Predicted translational consequences of each rmr1 mutation are indicated.

Figure 3:
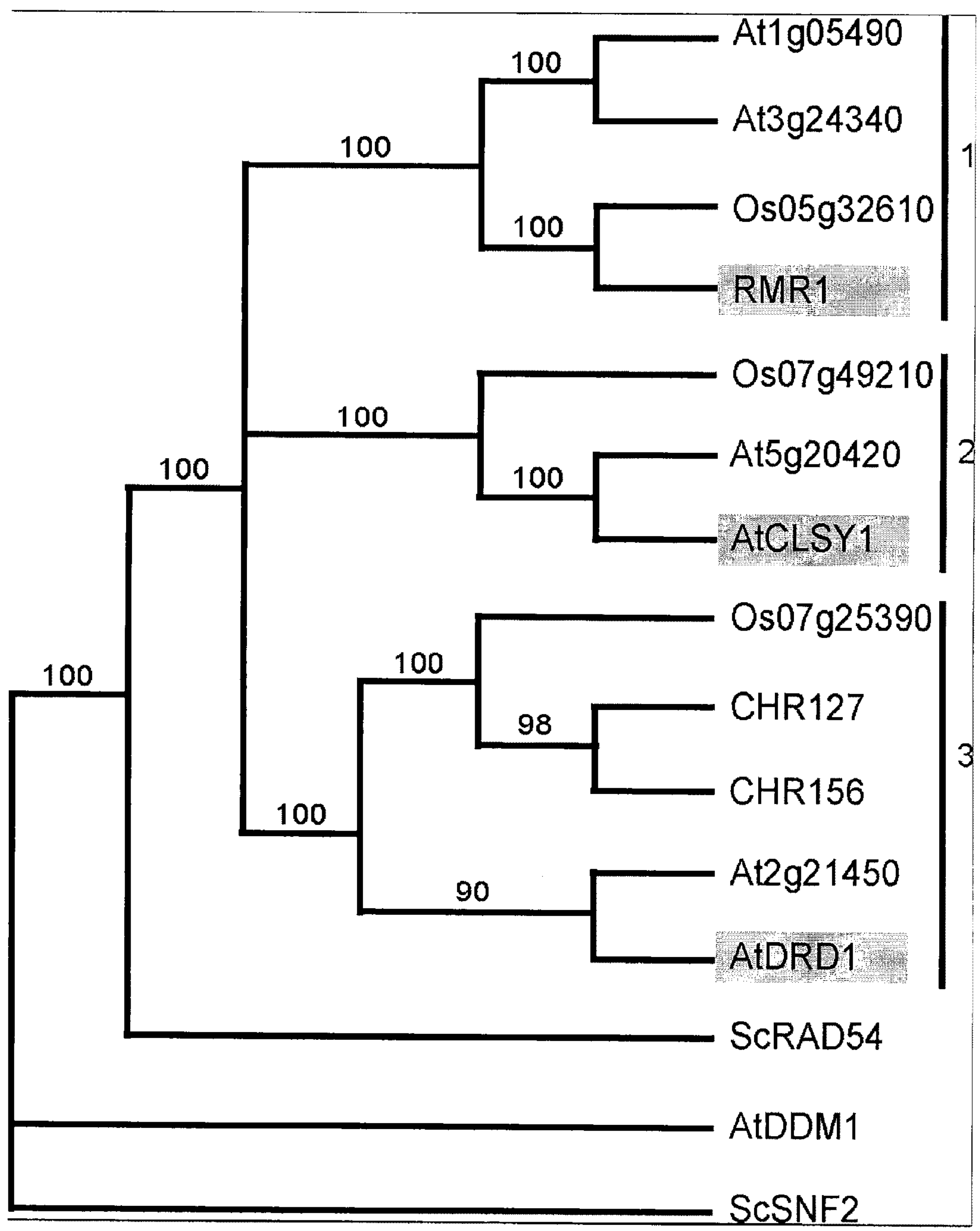

FIG. 3: RMR1 Defines a Monophyletic Clade Distinct from DRD1

Distance tree with bootstrap values produced from alignment (FIG. 8) of the predicted Snf2 domain with other Snf2 proteins: the tree shows that RMR1, CLSY1, and DRD1 (highlighted in gray) are members of a Rad54-like subfamily of Snf2 proteins. Three distinct monophyletic groups compose this subfamily, numbered 1 to 3. Prefixes: At, *Arabidopsis*; Os, rice; Sc, *S. cerevisiae.*

Figure 4:
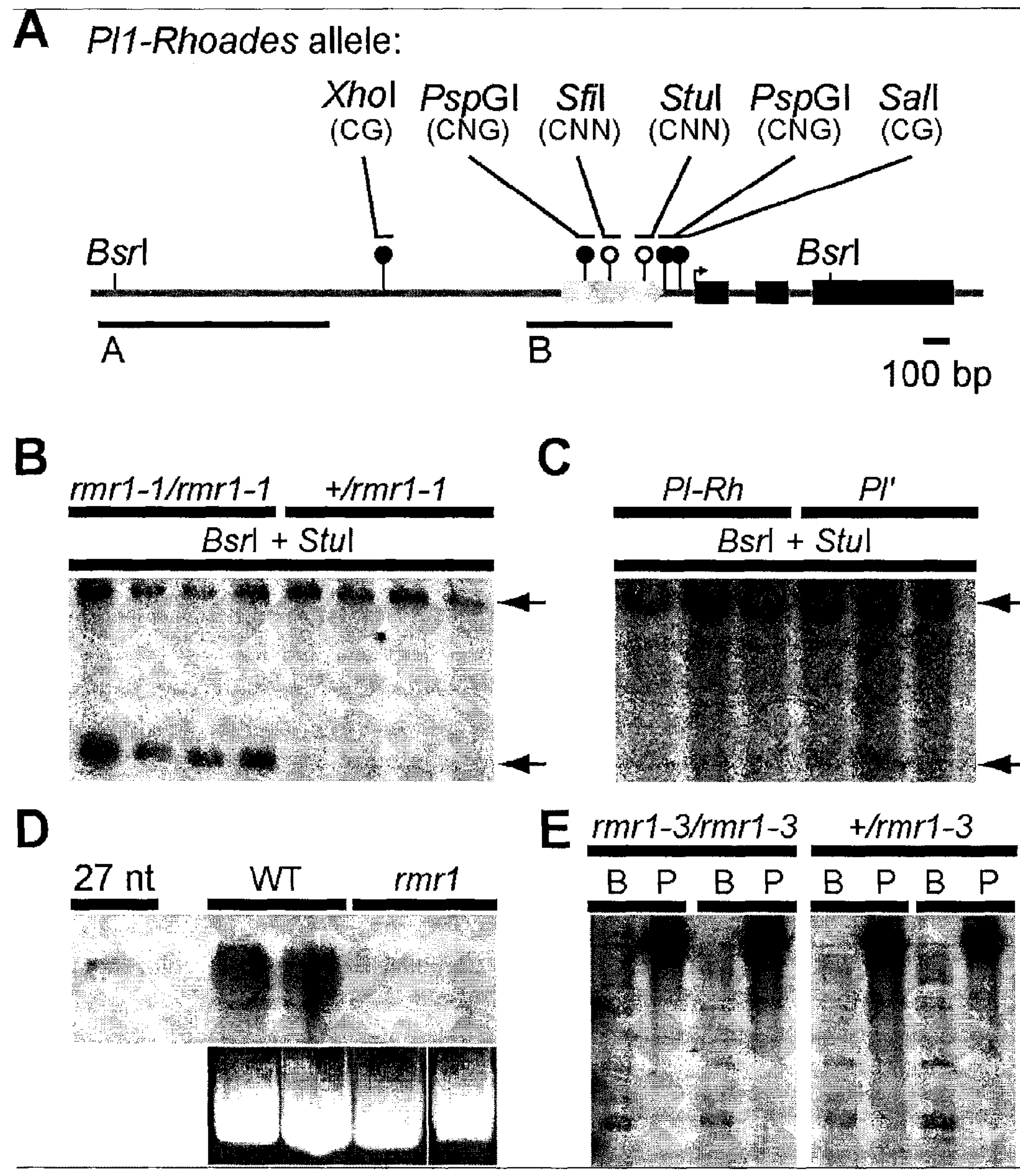

FIG. 4: Cytosine Methylation Patterns and Small RNA Accumulation Are Altered at Pl1-Rhoades in rmr1 Mutants (A) Schematic of Pl1-Rhoades locus with exons highlighted in black and the upstream doppia element represented by the gray arrow. The methylation context of sites cut by methylation-sensitive enzymes are shown in parentheses. Open circles denote sites hypomethylated in rmr1-1 mutants while filled circles are sites methylated in both wild-type and rmr1 mutants. BsrI restriction sites and the regions used to generate probes for blot hybridization analysis, denoted A and B, are also shown.

(B and C) Representative Southern blots hybridized with probe A showing methylation status at a StuI site in rmr1 mutants and heterozygous siblings (B), as well as Pl' and Pl-Rh plants (C) with a larger 2.9-kb band (upper arrow) representative of a fully methylated BsrI fragment, and a 2.1-kb band (lower arrow) indicative of a hypomethylated StuI site. Additional primary blots shown in FIGS. 9 and 14.

(D) Small RNA northern blot probed with doppia sequence from probe B showing changes in amount of small RNAs between rmr1-1 plants and wild-type (WT) siblings.

(E) Southern blot of genomic DNA digested with BstNI ("B" lanes) and methylation-sensitive PspGI ("P" lanes) hybridized with probe B, showing no bulk changes in doppia methylation genome-wide.

Figure 5:
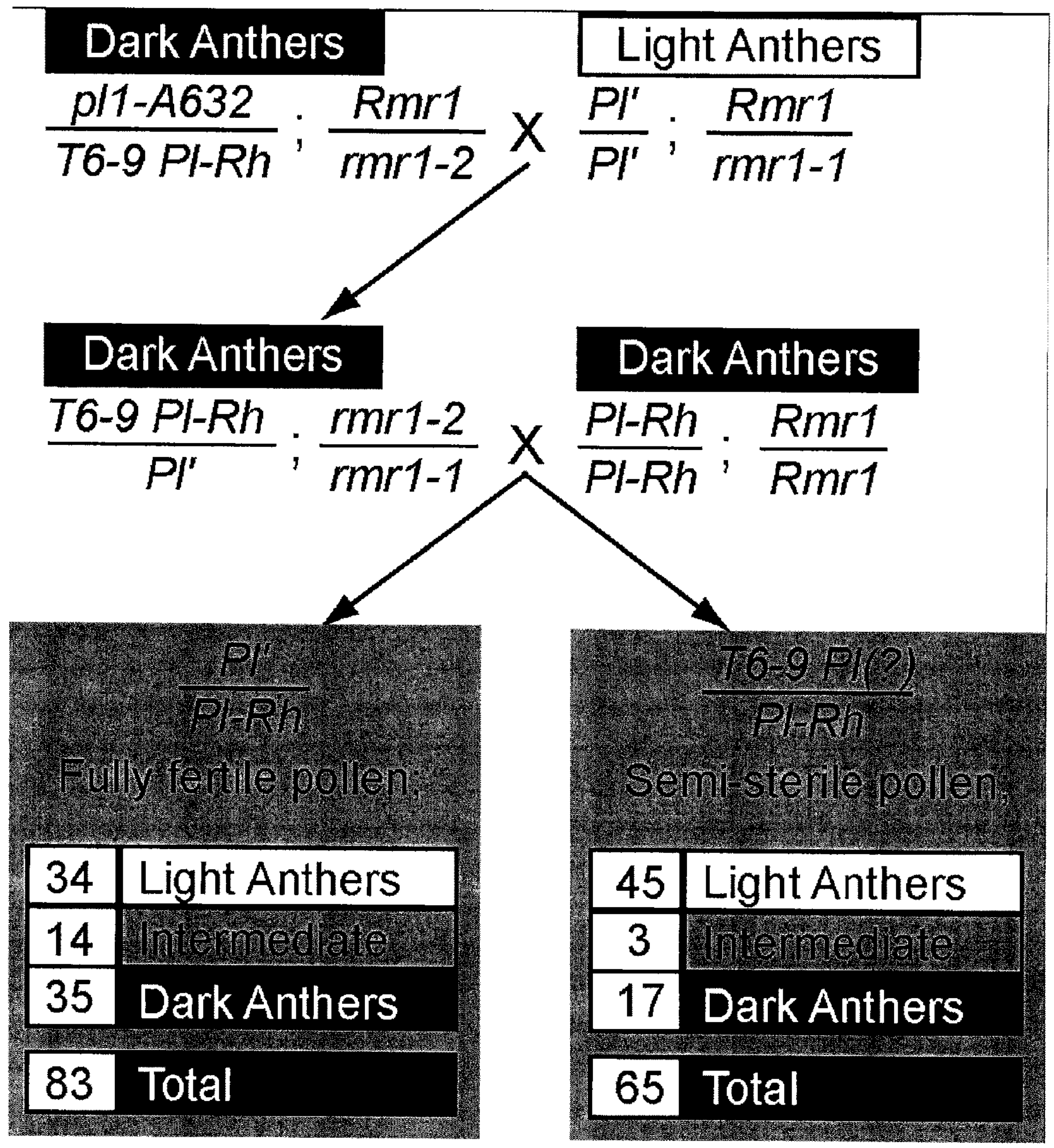

FIG. 5: Pl' Establishment in an rmr1 Mutant Background

Plants with a T6-9 translocation chromosome carrying Pl1-Rhoades in the Pl-Rh state (dark anther pigmentation) and heterozygous for the rmr1-2 allele were crossed to Pl' plants (light anther pigmentation) heterozygous for the rmr1-1 allele. Of the resultant progeny with semi-sterile pollen (heterozygous for the T6-9 interchange pair), plants homozygous for a mutation at rmr1 were chosen based on the dark anther phenotype. These plants were then crossed to a Pl-Rh tester with the expectation that in progeny inheriting the interchange, the expression status of the Pl1-Rhoades allele on the T6-9 translocation chromosome (T6-9 Pl(?)) would indicate if establishment of the Pl' state was affected in the F1. The numbers represent the number of plants displaying a given anther phenotype, indicating that the Pl' state was established on the interchange chromosome in the rmr1 mutants.

Figure 6:
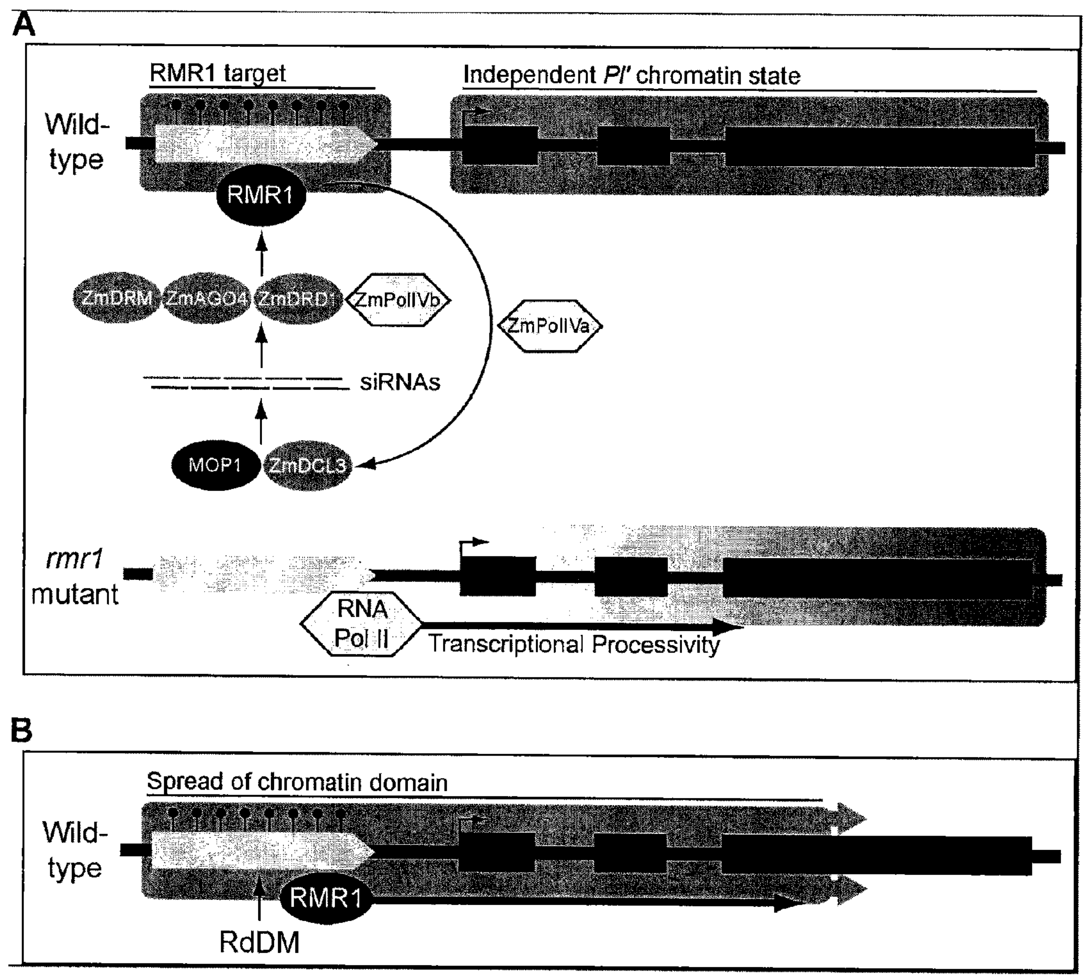

FIG. 6: Two General Models for RMR1 Action at the Pl1-Rhoades Allele

RMR1 maintains nonsymmetrical methylation of the doppia element (light gray arrow) upstream of the pl1 coding region (exons in black) via an RdDM pathway. Small RNAs are produced in a RMR1-dependent fashion with homology to the doppia element, and maize orthologs of characterized RdDM proteins, as well as RMR1, then act as effectors of these siRNAs, facilitating cytosine methylation at complementary sequences of the DNA template. In the model shown in (A), the heterochromatic region of doppia is maintained and established independently of the Pl1-Rhoades chromatin state, but derepression of the upstream repetitive element in an rmr1 mutant causes changes in the nearby genic region through processivity of RNA polymerase II or other general transcription factors that bind the upstream elements. In the model shown in (B), the doppia element is repressed by the same RdDM pathway shown in (A), but the Pl' state represents a spread of the heterochromatic domain beyond the region targeted by the siRNAs for cytosine methylation. This spread might be mediated by RMR1 activity, or by another chromatin modifier. In (B), loss of RMR1 would lead to a loss of the repressive chromatin state at doppia and the ability for it to spread.

Figure 7:
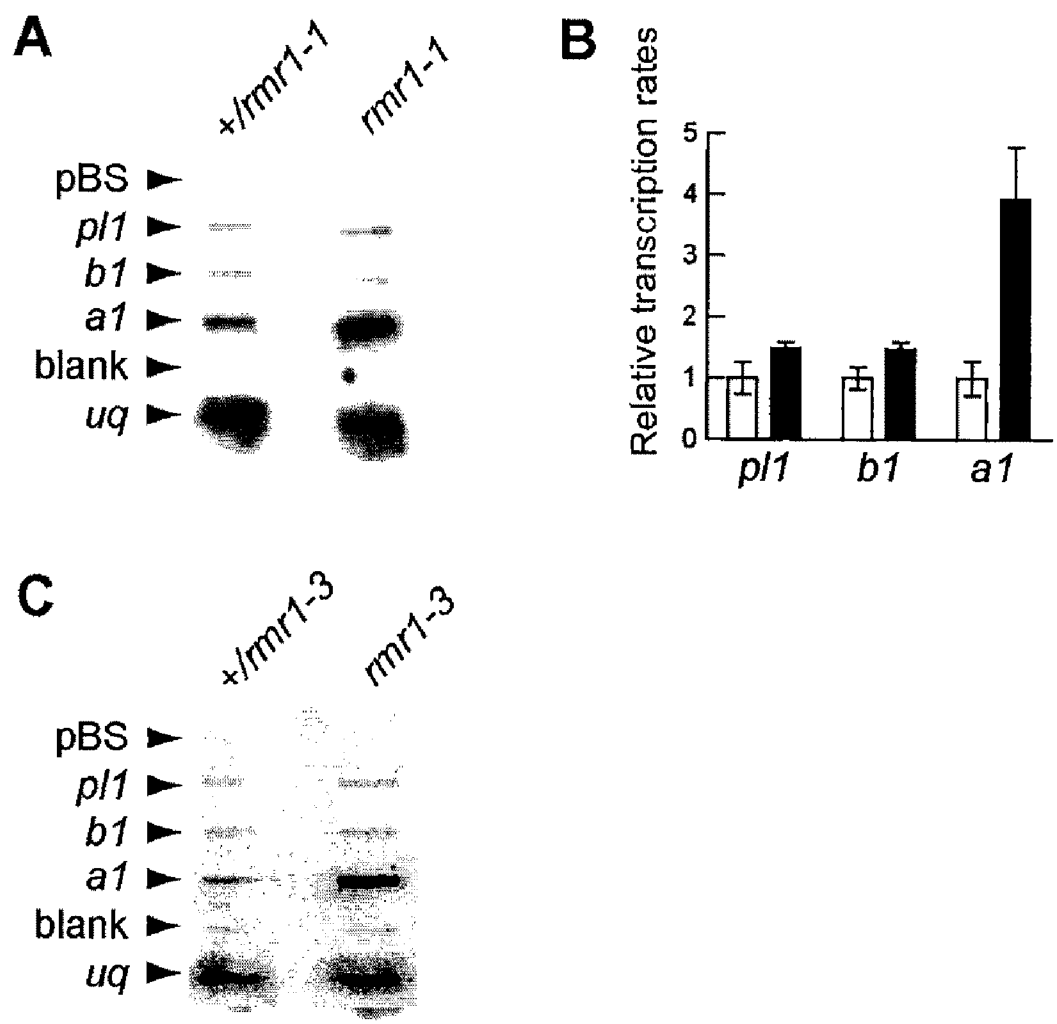

FIG. 7: Run-on transcription assay comparing rmr1 mutants to non-mutant heterozygotes.

Transcription rates of paramutant alleles are unaffected by Rmr1 action (A) In vitro radiolabeled RNAs corresponding to the indicated genes from isolated husk nuclei of sibling plants detected with slotblot hybridizations (pBS, bacterial plasmid DNA; pl1, purple plant1; b1, booster1; a1, anthocyaninless1; uq, ubiquitin). (B) Quantification of relative mean transcription rates from five independent sets of +/rmr1-1 (open) and rmr1-1/rmr1-1 (closed) siblings (±s.e.m.) showing no significant difference between pl1 transcription rates ($n=5$, 2-tailed 2-sample t-test, $t=2.1$, $P=0.1$). (C) In vitro radiolabeled RNAs from isolated husk nuclei of rmr1-3 mutants and heterozygous siblings used to generate quantification in FIG. 1.

FIG. 8: Alignment of RMR1 helicase domain with other known and predicted Snf2 proteins (SEQ ID NOs: 1-15)

Figure 9:
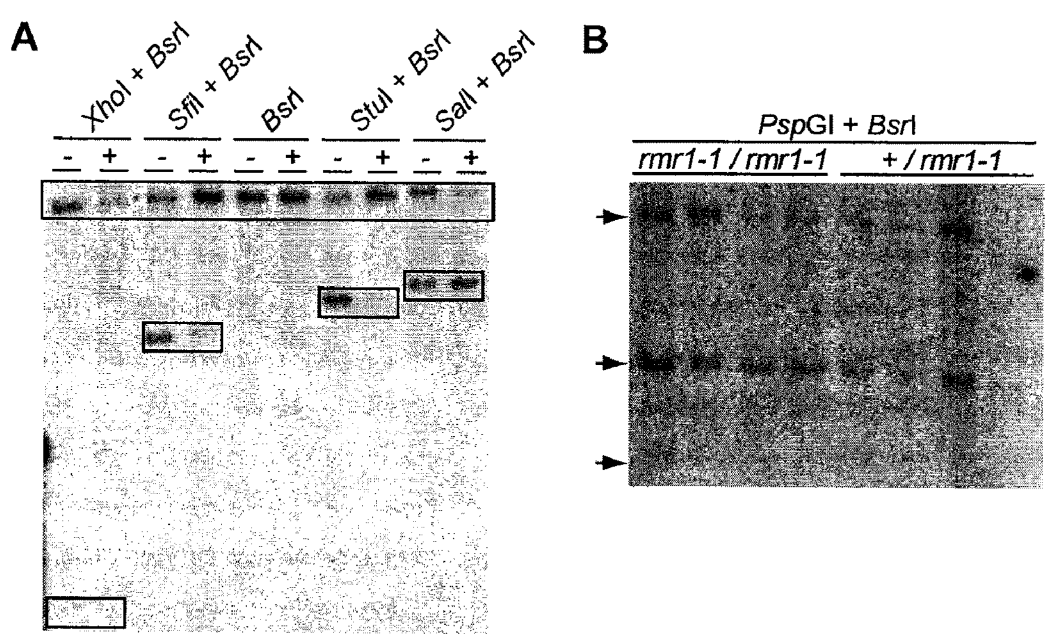

FIG. 9: Southern blots comparing the DNA methylation status of the region upstream of Pl1-Rhoades in rmr1-1 mutants and heterozygous siblings.

Additional Southern blots used to generate methylation profile in FIG. 4A. (A) Genomic digests of an rmr1-1 mutant (−) and heterozygous sibling (+) using the listed methylation-sensitive restriction enzymes in concert with BsrI, hybridized with probe A (FIG. 4A). The top box defines the band representing the full length BsrI fragment, and lower boxes represent digest products hypomethylated at the restriction site being tested. A site was considered hypomethylated if the lower band was of greater intensity in the mutant as compared to the non-mutant and this was accompanied by a concomitant depletion of the upper band. (B) Blot hybridized with probe A comparing rmr1-1 mutants to heterozygous siblings with respect to methylation at a PspGI site. The top arrow represents a fully methylated BsrI fragment, the second arrow represents the expected size of a BsrI fragment hypomethylated at a PspGI site 123 bp upstream of Pl1-Rhoades, and the lowest arrow represents a hypomethylated PspGI site internal to doppia, 389 bp upstream.

FIG. 10: Comparison of Pl1-Rhoades upstream methylation status in rmr6-1 mutants and heterozygous siblings.

(A) Shows a methylation profile similar to that shown in FIG. 4A showing sites at the Pl1-Rhoades locus hypomethylated (open circle) in an rmr6-1 mutant as compared to heterozygous siblings. Blots (B) and (C) were used to generate this profile and are analogous to the blots shown for rmr1 mutants in FIGS. 10 A and B respectively.

FIG. 11: Comparison of Pl1-Rhoades upstream methylation status in mop1-1 mutants and heterozygous siblings.

(A) Shows a methylation profile similar to that shown in FIG. 4A showing sites at the Pl1-Rhoades locus hypomethylated (open circle) in a mop1-1 mutant as compared to heterozygous siblings. Blots (B) and (C) were used to generate this profile and are analogous to the blots shown for rmr1 mutants in FIGS. 10 A and B respectively.

Figure 12:
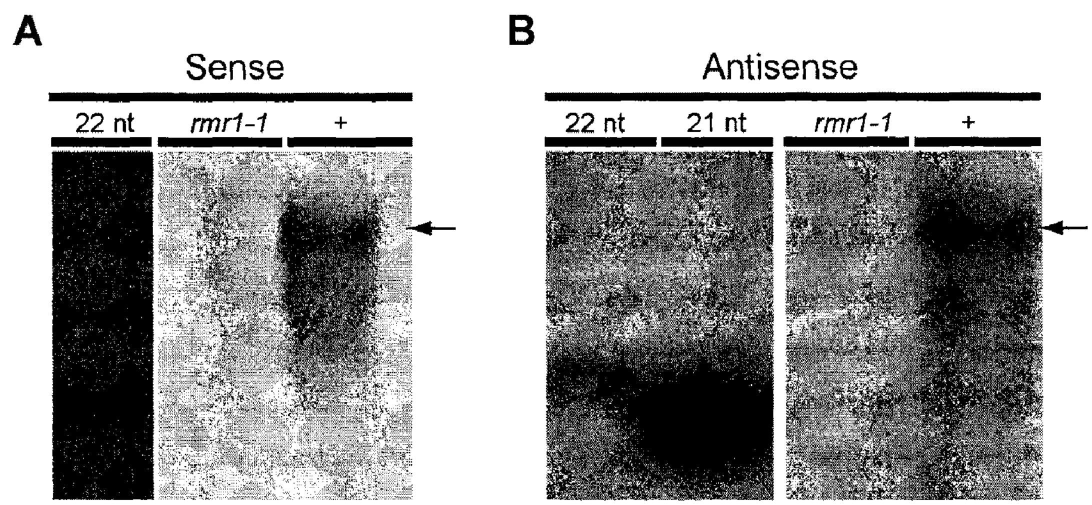

FIG. 12: Additional small RNA northern blots showing accumulation of doppia small RNAs are lost in both sense and antisense orientations in rmr1 mutants.

Small RNA northern blots were probed with Probe B (FIG. 4A) in both the sense (A) and antisense (B) orientations showing small RNAs (~26 nt) with doppia sequence similarity are present in sense and antisense orientation in rmr1-1 heterozygotes (+) and are lost in rmr1-1 mutants. 22 and 21 nt DNA oligos used as sizing standards are also shown.

Figure 13:
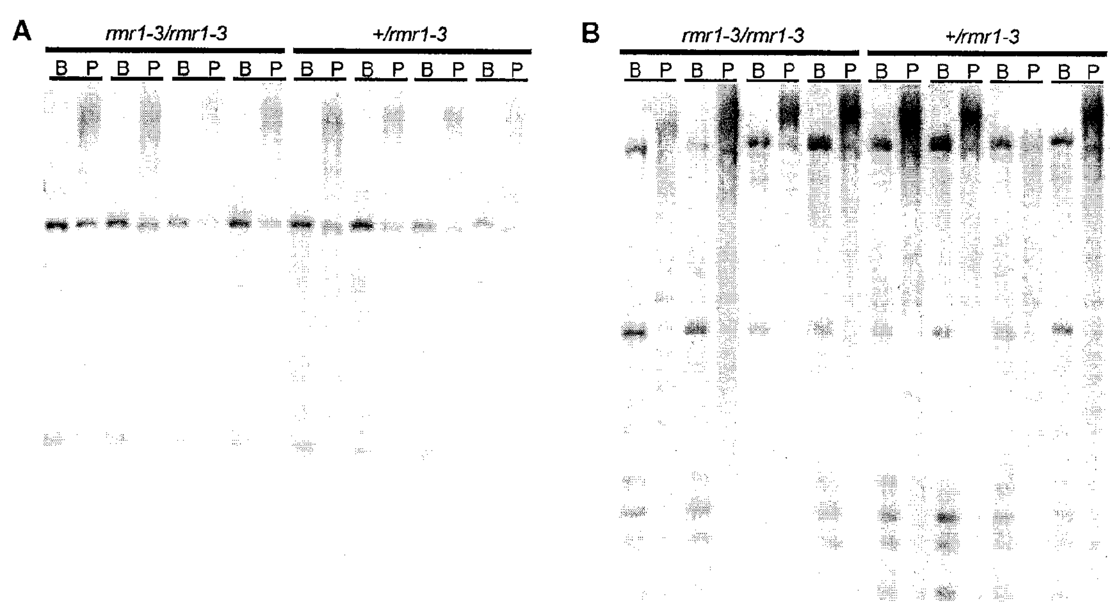

FIG. 13: Mutations at rmr1 do not affect genome-wide methylation levels.

(A) Genomic DNA from four rmr1-3 mutants and non-mutant siblings, digested with BstNI (B) and a CNG methylation-sensitive enzyme, PspGI (P) which has the same recognition site, probed with radiolabled centromere sequence and (B) 45S repeat sequence. A comparison between the PspGI digests in mutant and non-mutant individuals reveals no gross methylation differences.

Figure 14:
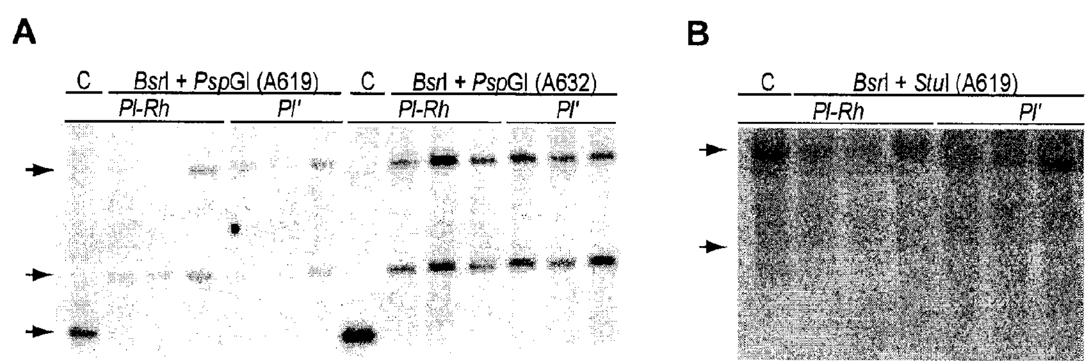

FIG. 14: Additional Southern blots showing no changes in Pl1-Rhoades methylation status between the Pl-Rh and Pl' states.

(A) The methylation status of upstream PspGI sites was compared for Pl'/Pl' and Pl-Rh/Pl-Rh plants with the Pl1-Rhoades allele introgressed into distinct A619 and A632 backgrounds via hybridization with probe A. The arrows are as indicated on FIG. 10B and the blot reveals no methylation differences at this site between the two Pl1-Rhoades regulatory states. The 'C' lanes indicated control lanes where the digest was carried out with the BstNI, methylation-insensitive, restriction enzyme.

(B) Is analogous to blot shown in FIG. 4C though the plants are from a different background (A619 introgression) than the plants used in FIG. 4C (A632 introgression) showing that there are no methylation differences at the StuI site in either background.

Figure 15:
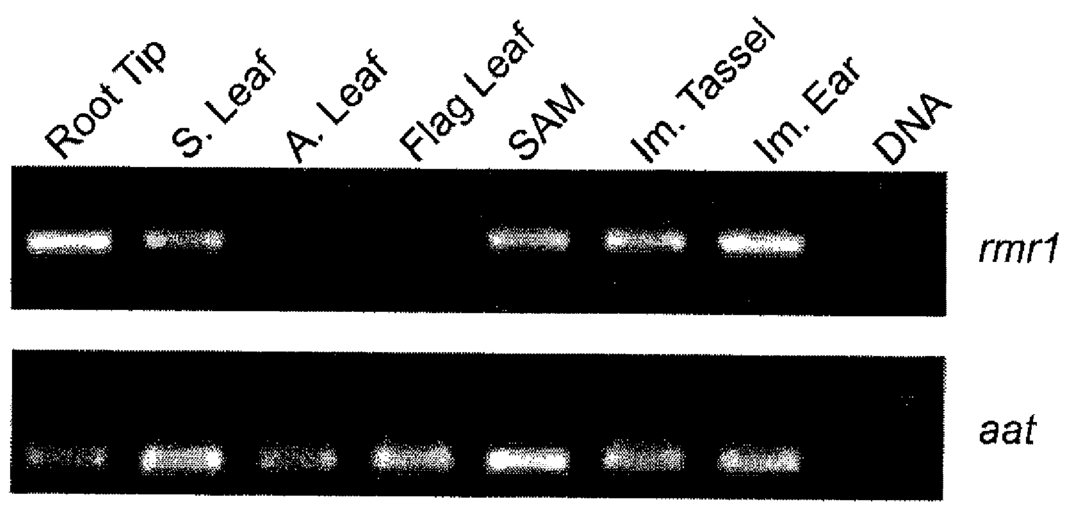

FIG. 15: RT-PCR expression profile of rmr1 in wild-type tissue S. Leaf, seedling leaf; A. Leaf, adult leaf; SAM, shoot apical meristem; Im. Tassel, immature tassel; Im. Ear, immature ear. RT-PCR was carried out using primers that span the first and second introns of rmr1.

Figure 16:
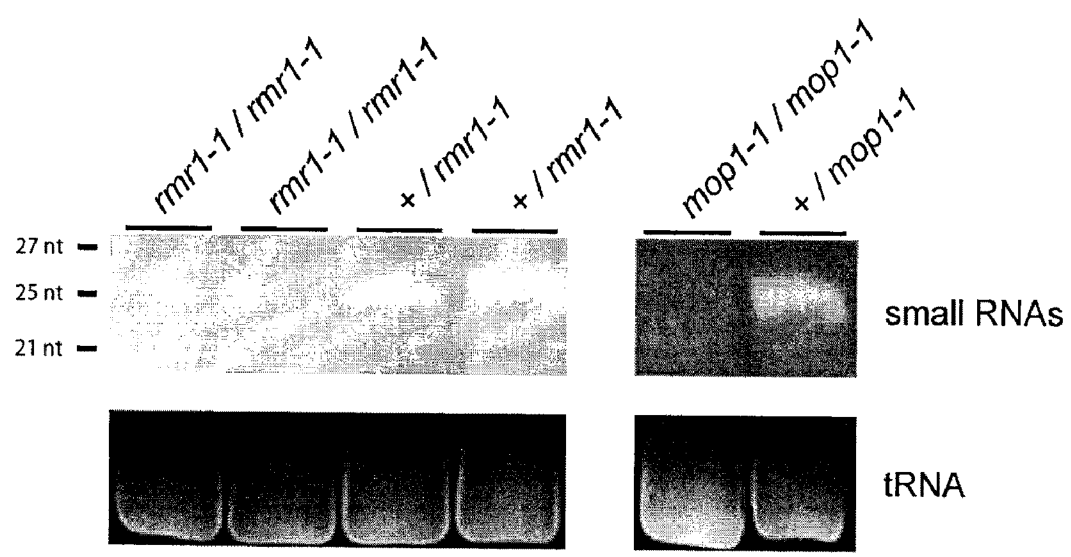

FIG. 16: RMR1 and MOP1 small RNA profiles. Etbr staining of 20 μg enriched small RNAs following PAGE separation. Sizes of DNA oligonucleotides is noted for reference.

Figure 17:
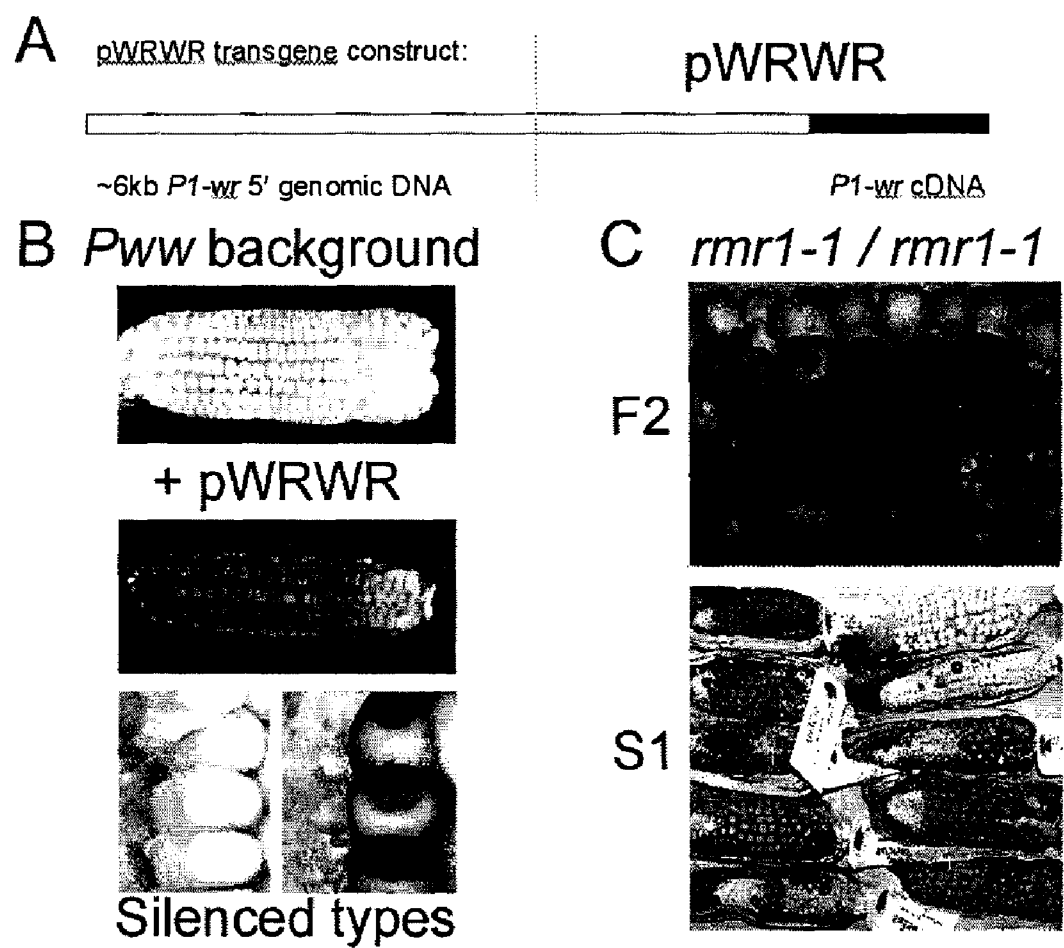

FIG. 17: Reactivation of silenced pWRWR transgenes.

(A) Schematic of pWRWR design.

(B) Pericarp phenotype of Pww null, Pww line with an active pWRWR transgene and subsequent silenced epigenotypes.

(C) Example of somatic reactivation of silenced pWRWR in ear of one rmr1-1 F2 homozygote and subsequent S1 progeny.

Figure 18:
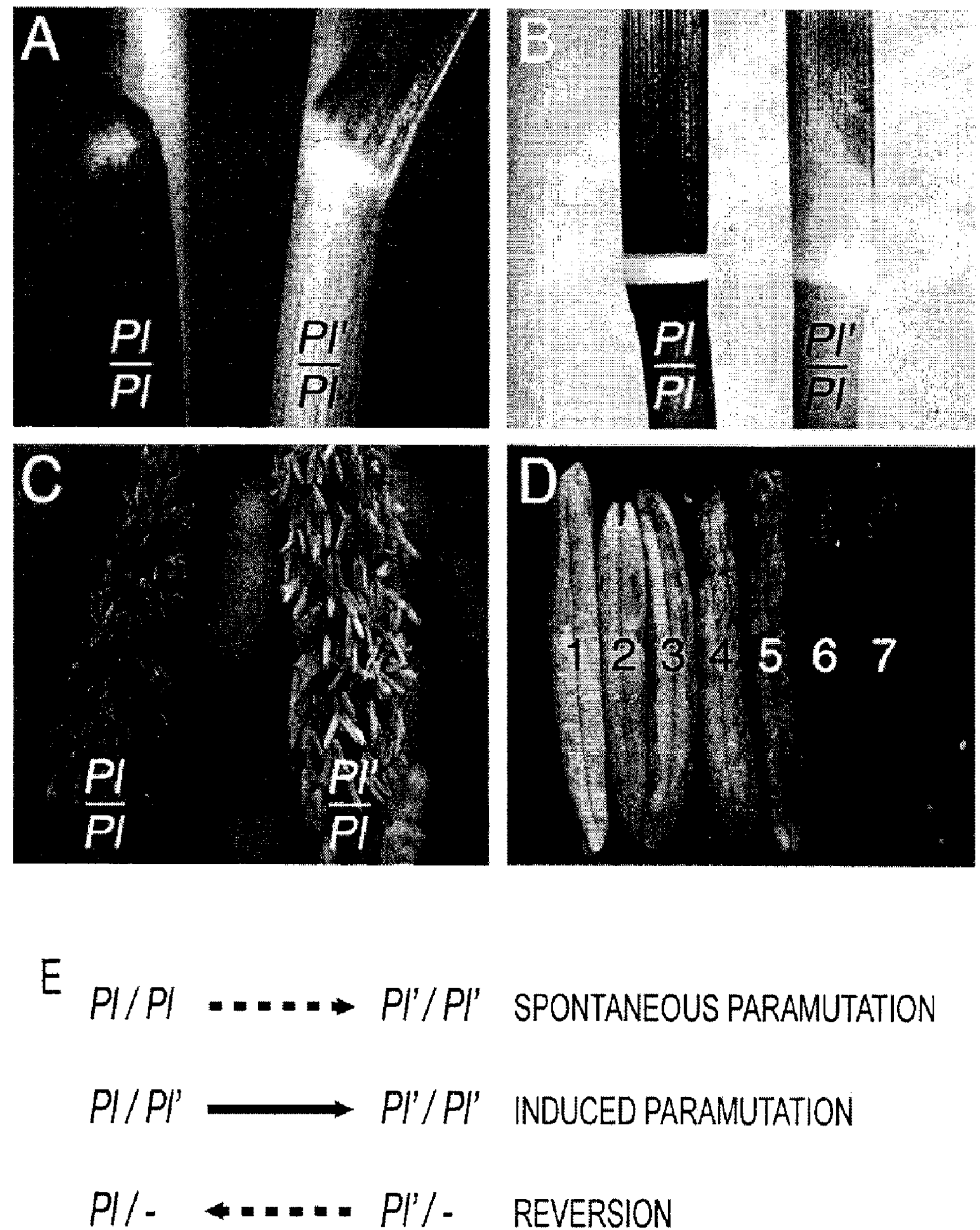

FIG. 18: pl1 paramutation.

Pl and Pl' phenotypes from (A) seedling leaf sheath, (B) mature leaf sheath and (C) tassels.

(D) Quantification of pl1 expression in anther tissues is determined by a 1-7 graded series of Another Color Scores (ACS).

(E) Allelic behaviors. Pl is unstable and can, at various frequencies (indicated by dashed line), change to a transcriptionally repressed state referred to as Pl' (spontaneous paramutation). Pl invariably (indicated by solid line) changes to a Pl' state when Pl is exposed to Pl' (induced paramutation). Pl' can revert, at various frequencies (indicated by dashed line), to Pl, when heterozygous with some alleles or when hemizygous.

Figure 19:
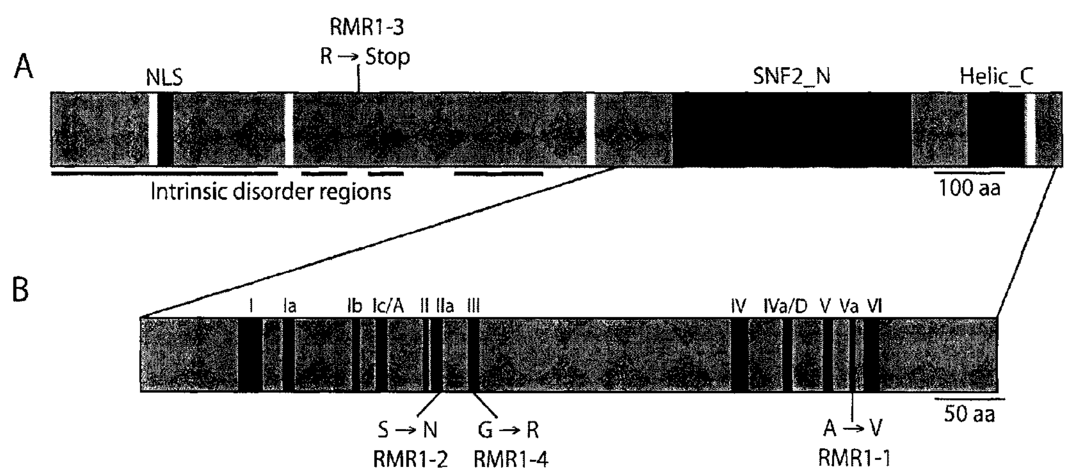

FIG. 19: RMR1 features.

(A) In silico translation of rmr1 genomic sequence highlighting a canonical bipartite nuclear localization signal (NLS, dark grey box, PredictNLS: http://cubic.bioc.columbia.edu/predictNLS/), highly conserved SNF2_N and Helic_C domains (black boxes), regions of high intrinsic disorder (underlined, see text), and locations of intended peptides for antisera production (white boxes). Position and nature of the rmr1-3 nonsense lesion is noted.

(B) RMR1 conserved domain (RMR1cd; aa813-1423) highlighting helicase motifs found within the SNF2_N and Helic_C profiles, and three non-functional RMR1 variants. Non-traditional motifs Ib, Ic, IVa, and Va were described by Dürr et al. (2006) in the analysis of the *Sulfolobus solfataricus* RAD54 structure; A and D denote motifs described by Thoma et al. (2005) in the analysis of *D. rerio* Rad54 structure that overlap with Ic and IVa. Functions of these motifs are based on available structural data: I—Walker A box, binds γ-P of ATP; Ia—3' to 5' DNA contacts; Ib—5' to 3' DNA contacts; Ic/C—minor grove contacts; II—Walker B box (DExx helicase motif), provides the Glu residue involved in ATP hydrolysis; Ia—thought to interface DNA binding to catalytic ATP hydrolysis by facilitating conformational change; III and VI—ATP binding; IV and V—DNA binding. Mutations in IVa inhibit ATP hydrolysis.

Figure 20:
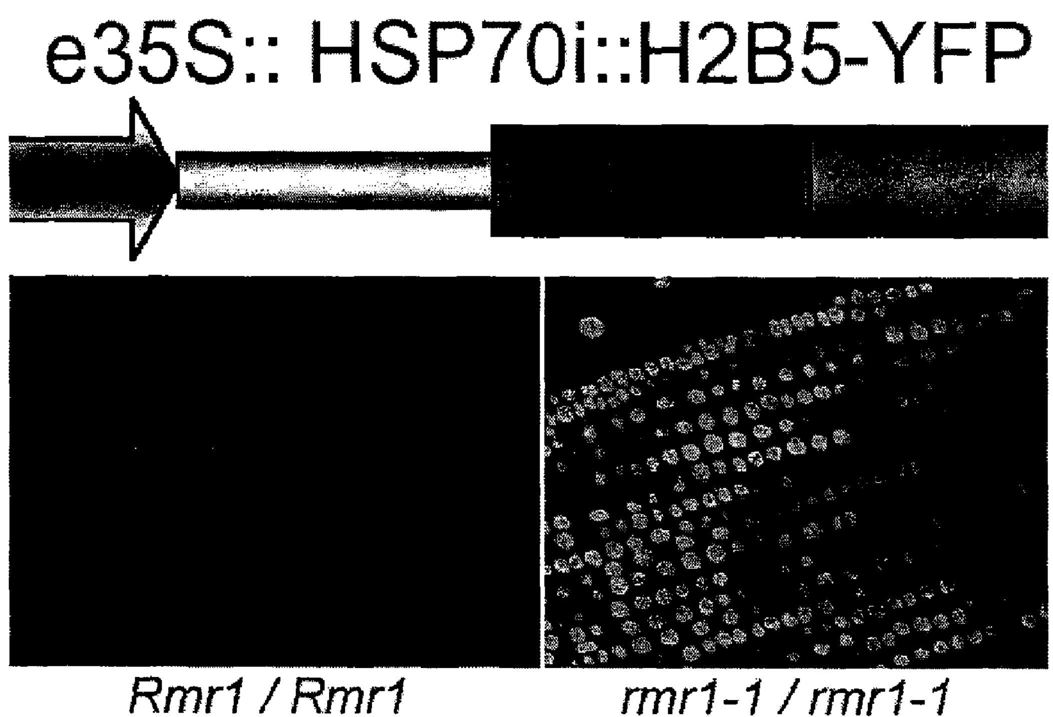

FIG. 20: Cell-autonomous transgene marker construct and root tips images from silenced and reactivated lines. (courtesy of J. Gutiérrez-Marcos)

DETAILED DESCRIPTION OF THE INVENTION

Genetics is founded on the principle that heritable changes in genes are caused by mutations and that the regulatory state of gene pairs (alleles) is passed on to progeny unchanged. An exception to this rule, paramutation, produces changes in gene control that are stably inherited without altering the DNA sequence. It is currently thought that these allelic interactions cause structural alterations to the chromatin surrounding the gene. Recent work in both maize and mice suggests that RNA molecules may be responsible for paramutations. Several genes are required to maintain the repressed paramutant state of a maize purple plant1 (pl1) allele, and here we report that one of these genes encodes a protein (RMR1) with similarity to a protein previously implicated in facilitating genomic DNA modifications via small RNA molecules. Genetic and molecular experiments support a similar role for RMR1 acting at a repeated sequence found adjacent to this pl1 gene. Although loss of these DNA modifications leads to heritable changes in gene regulation, the data indicate these changes do not represent the heritable feature responsible for paramutation. These findings highlight an unusual but dynamic role for repeated genomic features and small RNA molecules in affecting heritable genetic changes independent of the DNA template. Paramutations represent heritable epigenetic alterations that cause departures from Mendelian inheritance. While the mechanism responsible is largely unknown, recent results in both mouse and maize suggest paramutations are correlated with RNA molecules capable of affecting changes in gene expression patterns. In maize, multiple required to maintain repression (rmr) loci stabilize these paramutant states. Here we show rmr1 encodes a novel Snf2 protein that affects both small RNA accumulation and cytosine methylation of a proximal transposon fragment at the Pl1-Rhoades allele. However, these cytosine methylation differences do not define the various epigenetic states associated with paramutations. Pedigree analyses also show RMR1 does not mediate the allelic interactions that typically establish paramutations. Strikingly, our mutant analyses show that Pl1-Rhoades RNA transcript levels are altered independently of transcription rates, implicating a post-transcriptional level of RMR1 action. These results suggest the RNA component of maize paramutation maintains small heterochromatic-like domains that can affect, via the activity of a Snf2 protein, the stability of nascent transcripts from adjacent genes by way of a cotranscriptional repression process. These findings highlight a mechanism by which alleles of endogenous loci can acquire novel expression patterns that are meiotically transmissible.

The term "paramutation" describes a genetic behavior in which the regulatory state of specific alleles is heritably altered through interactions with their homologous partners in trans [1,2]. This behavior presents an exception to the Mendelian principle that alleles segregate from a heterozygous state unchanged [3]. Paramutations have been best characterized at loci encoding transcriptional regulators of pigment biosynthesis in maize, but similar behaviors have been described in other plant and animal systems, most recently in mice [4,5]. While the broader roles of paramutation in genome-wide regulation and evolution remain to be seen, the Pl1-Rhoades allele of the maize purple plant1 (pl1) locus presents a tractable system to study the paramutation process.

The pl1 locus encodes a Myb-like protein that acts as a transcriptional activator of genes required for anthocyanin pigment production [6]. Inheritance patterns illustrate that the Pl1-Rhoades allele can exist in quantitatively distinct regulatory states, reflected by differences in plant color. When individuals with a highly expressed reference state of Pl1-Rhoades, termed Pl-Rh, are crossed with plants having a repressed state, referred to as Pl', only progeny with weak pigmentation are produced [7,8]. Pl-Rh states invariably change to Pl' in Pl-Rh/Pl' heterozygotes [7]; this is a typical hallmark of paramutation. Relative to Pl-Rh, the Pl' state displays reductions in both Pl1-Rhoades RNA levels (~10-fold) and transcription rate (~3-fold) that are associated with a reduction in plant pigment [8]. This repressed Pl' state is meiotically stable when maintained in a Pl1-Rhoades homozygote, with no reversion to Pl-Rh seen to date. Pl' can, however, revert to Pl-Rh when heterozygous with some pl1 alleles other than Pl1-Rhoades, when maintained in a hemizygous condition, or in the presence of specific recessive mutations [9-12].

Genetic screens for ethane methyl sulfonate (EMS)-induced recessive mutations identify at least ten loci, including required to maintain repression1 (rmr1), rmr2, rmr6, and mediator of paramutation1 (mop1), whose normal functions maintain the repressed Pl' state ([10,11,13]; J. B. H., unpublished data). These rmr mutations specifically affect the expression of Pl1-Rhoades and not other pl1 alleles [10,11], indicating that the Pl1-Rhoades allele is a direct and specific target of paramutation-based epigenetic changes. mop1 was recently identified [14,15] as encoding the putative ortholog of the *Arabidopsis* protein RDR2, a presumed RNA-dependent RNA polymerase involved in siRNA-based maintenance of de novo cytosine methylation [16]. Recessive mutations defining rmr1, rmr2, and rmr6 destabilize the repressed Pl' state, resulting in darkly pigmented plant tissues, an increase in pl1 RNA levels, and meiotic transmission of Pl-Rh revertant states [10,11]. To date, the molecular identity of these rmr factors remains unknown. There thus remains a need to identify the molecular identity of these rmr factors. There is also a need to reduce or mitigate gene silencing in transgenic plants and to reduce inbreeding depression during plant breeding.

In this report we identify rmr1 as encoding a novel Snf2 protein that represents a founding member of a subgroup of factors similar to proteins involved in plant small RNA metabolism. Our analyses show that RMR1 affects both pl1 RNA transcript stability as well as small interfering RNA (siRNA) accumulation and DNA methylation patterns at Pl1-Rhoades. These results support a model in which maintenance of paramutant states is dependent on a repression mechanism similar to the recently proposed cotranscriptional gene silencing mechanism in fission yeast [17,18]. To our knowledge, RMR1 is the first protein identified that maintains trans-generationally repressed states established by paramutation.

DEFINITIONS

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions and in most plant tissues. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "plant promoter" is a promoter capable of initiating transcription in plant cells.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. The expression vector can be an RNA or a DNA vector. Typically, the expression vector includes a nucleic acid to be transcribed operably linked to a promoter (an expression cassette). An "expression cassette" refers to a subsequence of the expression vector.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 6 7 amino acids or 25 nucleotides in length, or more preferably over a region that is 50 100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389 3402 (1977) and Altschul et al., J. Mol. Biol. 215:403 410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873 5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Cloning of Target Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, (1989) or Current Protocols in Molecular Biology Volumes 1 3 (Ausubel, et al., eds. 1994 1998).

The isolation of nucleic acids corresponding to target genes may be accomplished by a number of techniques. For instance, oligonucleotide probes based on known sequences can be used to identify the desired gene in a cDNA or genomic DNA library. To construct genomic libraries, large segments of genomic DNA are generated by random fragmentation, e.g. using restriction endonucleases, and are ligated with vector DNA to form concatamers that can be packaged into the appropriate vector. To prepare a cDNA library, mRNA is isolated from the desired organ, such as flowers, and a cDNA library which contains the target gene transcript is prepared from the mRNA. Alternatively, cDNA may be prepared from mRNA extracted from other tissues in which target genes or homologs are expressed.

The cDNA or genomic library can then be screened using a probe based upon the sequence of a cloned target gene. Probes may be used to hybridize with genomic DNA or cDNA sequences to isolate homologous genes in the same or different plant species. Alternatively, antibodies raised against an target polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the target genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis et al., eds. 1990).

Polynucleotides may also be synthesized by well-known techniques as described in the technical literature (see, e.g., Carruthers et al., Cold Spring Harbor Symp. Quant. Biol. 47:411 418 (1982), and Adams et al., J. Am. Chem. Soc. 105:661 (1983). Double stranded DNA fragments may then be obtained either by synthesizing the complementary strand and annealing the strands together under appropriate conditions, or by adding the complementary strand using DNA polymerase with an appropriate primer sequence.

Promoters and Expression Vectors

As described below, a vector containing a recombinant nucleic acid can be introduced into a plant by any suitable method. For example, the construct can be introduced into a plant via stable transformation with *Agrobacterium*, particle bombardment, electroporation, or transduction with a viral particle. A suitable expression vector is therefore selected according to the desired method of plant transformation.

In one embodiment, the construct is expressed via a DNA expression vector. Such expression vectors comprise DNA dependent RNA polymerase promoters that are active in plant cells, e.g., constitutive plant promoters such as those described herein and above (e.g., the nopaline synthase promoter, Sanders et al., Nuc. Acids Res. 15:1543 1558 (1987); or the CaMV 35S promoter, Urwin et al., Mol. Plant Microbe Interact. 10:394 400 (1997)) or tissue specific plant promoters such as those described herein and above.

In another embodiment, the gene silencing construct is transcribed via an RNA expression vector. The RNA expression vector encodes an RNA dependent RNA polymerase active in plant cells, and the gene silencing construct is transcribed via an RNA dependent RNA polymerase promoter active in plant cells. Suitable RNA dependent RNA polymerases and their corresponding promoters and expression vectors are derived, e.g., from potato virus X (Chapman et al., Plant J. 2:549 557 (1992), tobacco mosaic virus (see, e.g., Dawson et al., Virology 172:285 292 (1989)), tobacco etch virus (see, e.g., Dolja et al., Proc. Nat'l Acad. Sci. USA 89:10208 10212 (1992)), tobacco rattle virus (see, e.g., Ziegler-Graff et al., Virology 182:145 155 (1991)), tomato bushy stunt virus (see, e.g., Scholthof et al., Mol. Plant Microbe Interact. 6:309 322 (1993)), brome mosaic virus (see, e.g., Mori et al., J. Gen. Virol. 74:1255 1260 (1993)). Such expression vectors are prepared using techniques known to those of skill in the art, e.g., by using bacterial RNA polymerases such as SP6 and T7 followed by manual inoculation, or by introduction of the vectors into plants by *Agrobacterium*-mediated transformation (Angell & Baulcombe, EMBO J. 16: 3675 3684 (1997)).

In another embodiment, optionally, a DNA expression vector also comprises a gene encoding an RNA dependent RNA polymerase active in plant cells. The RNA dependent RNA polymerase is then used to amplify the construct (either the positive and/or the negative strand).

In another embodiment, the construct is expressed via a DNA expression vector derived from a plant DNA virus, e.g., cauliflower mosaic virus (see, e.g., Futterer & Hohn, EMBO J. 10:3887 3896 (1991), African cassaya mosaic virus (see, e.g., Ward et al., EMBO J. 7:1583 1587 (1988)) and the tomato golden mosaic virus.

In the present invention, a plant promoter may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include for example, ACT11 from *Arabidopsis* (Huang et al. Plant Mol. Biol. 33:125 139 (1996)), Cat3 from *Arabidopsis* (GenBank No. U43147, Zhong et al., Mol. Gen. Genet. 251:196 203 (1996)), the gene encoding stearoyl-acyl carrier protein desaturase from *Brassica napus* (Genbank No. X74782, Solocombe et al. Plant Physiol. 104:1167 1176 (1994)), GPc1 from maize (GenBank No. X15596, Martinez et al., J. Mol. Biol. 208:551 565 (1989)), and Gpc2 from maize (GenBank No. U45855, Manjunath et al., Plant Mol Biol. 33:97 112 (1997)).

Alternatively, the plant promoter may direct expression of the construct in a specific tissue, organ or cell type (i.e. tissue-specific promoters) or may be otherwise under more precise environmental or developmental control (i.e. inducible promoters). Examples of environmental conditions that may effect transcription by inducible promoters include pathogen challenge, anaerobic conditions, elevated temperature, the presence of light, or spraying with chemicals/hormones. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in roots and feeding cells can be used. In particular, such promoters are useful for using the methods of the invention to inhibit nematode endoparasites that live in roots. The root-specific ANR1 promoter is suitable for use in the present invention (Zhang & Forde, Science 279:407 (1998)). The wound specific promoter wun-1 from potato can be used, as it respond to intracellular root migration by *Globodera* sp. (see, e.g., Hansen et al., Physiol. Mol. Plant Pathol. 48:161 170 (1996)). Other genes that demonstrate parasitic nematode feeding-cell specific expression have been reported, and their promoters are suitable for use in the present invention (see, e.g., Bird et al., Mol. Plant Microbe Interact. 7:419 424 (1994); Gurr et al., Mol. Gen. Genet. 226:361 366 (1991)); Lambert et al., Nucl. Acids. Res. 21:775 776 (1993); Opperman et al., Science 263:221 223 (1994); Van der Eycken et al., Plant J. 9:45 54 (1996); and Wilson et al., Phytopathology 84:299 303 (1992)). Phloem specific promoters, which can be used to express the gene silencing construct of the invention for uptake by sap-sucking insects, include those referenced in Shi et al., J. Exp. Bot. 45:623 631 (1994).

The vector comprising the gene silencing construct will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfaron or Basta.

Plant Transformation

Expression vectors of the invention may be introduced into the genome of the desired plant host by a variety of conventional techniques. For example, the expression vector may be introduced directly into the genomic DNA of the plant cell using techniques such as electroporation and microinjection of plant cell protoplasts, or the expression vectors can be introduced directly to plant tissue using ballistic methods, such as particle bombardment. In addition, the constructs of the invention may be introduced in plant cells as DNA or RNA expression vectors or viral particles that co-express an RNA dependent RNA polymerase.

Microinjection techniques are known in the art and well described in the scientific and patent literature. The introduction of expression vectors using polyethylene glycol precipitation is described in Paszkowski et al. EMBO J. 3:2717 2722 (1984). Electroporation techniques are described in Fromm et al., Proc. Natl. Acad. Sci. USA 82:5824 (1985). Ballistic transformation techniques are described in Klein et al. Nature 327:70 73 (1987).

Alternatively, the expression vectors may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*—mediated transformation techniques, including disarming and use of binary vectors, are well described in the scientific literature (see, e.g., Horsch et al., Science 233:496 498 (1984); Fraley et al. Proc. Natl. Acad. Sci. USA 80:4803 (1983) and Gene Transfer to Plants (Potrykus, ed. 1995)).

Transformed plant cells which are derived by any of the above transformation techniques can be cultured to regenerate a whole plant which possesses the transformed genotype and thus the desired phenotype such as enhanced resistance to pathogens. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124 176 (1983); and Binding, Regeneration of Plants, Plant Protoplasts, pp. 21 73 (1985). Regeneration can also be obtained from plant callus, explants, organs, or parts thereof. Such regeneration techniques are described generally in Klee et al., Ann. Rev. of plant Phys. 38:467 486 (1987).

The nucleic acids of the invention can be used to confer desired traits on essentially any plant. Thus, the invention has use over a broad range of plants, including wheat, corn, rice, sorghum, pepper, tomato, squash, banana, strawberry, carrot, bean, cabbage, beet, cotton, grape, pea, pineapple, potato, soybean, yam, and alfalfa, as well as other species described herein.

One of skill will recognize that after the expression cassette is stably incorporated in transgenic plants, if such a technique is used, and confirmed to be operable, it can be introduced into other plants by sexual crossing. Any of a number of standard breeding techniques can be used, depending upon the species to be crossed.

Using known procedures one of skill can screen for plants of the invention by detecting the effect of the construct of the invention in the target organism, either using in vitro assays such as plant culture, or in vivo assays such as transgenic plants. Means for directly and indirectly detecting and quantitating protein and RNA expression in vitro and in cells are well known in the art.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledenous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., Eds., (1984) Handbook of Plant Cell Culture—Crop Species, Macmillan Publ. Co., New York, N.Y.; Shimamoto et al. (1989) Nature 338: 274-276; Fromm et al. (1990) Bio/Technol. 8: 833-839; and Vasil et al. (1990) Bio/Technol. 8: 429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Antisense and RNAi Constructs

Antisense and RNAi treatments represent one way of altering rmr1 expression in accordance with the invention. In particular, constructs comprising an rmr1 sequence, including fragments thereof, in sense and/or antisense orientation, may be used to decrease or effectively eliminate its expression in a plant.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host plant or part thereof. In certain embodiments of the invention, such an RNAi or antisense oligonucleotide may comprise any unique portion of a nucleic acid sequence provided herein.

Constructs may be designed that are complementary to all or part of the promoter and other control regions, exons, introns or even exon-intron boundaries of a gene. It is contemplated that the most effective constructs will include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

All publications, patents, and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1

Rmr1 Defects Affect Pl1 RNA Stability

The rmr1 locus is defined by four recessive mutations characterized by a darkly pigmented plant phenotype that results from loss of Pl repression. Previous RNase protection experiments showed a 26-fold increase in pl1 RNA in floret tissue between rmr1-1 mutant plants and heterozygous siblings [10]. However, these experiments did not address if changes in pl1 transcript abundance correlated with changes in actual transcription at the pl1 locus.

In vitro transcription assays using nuclei isolated from husk leaf tissue revealed there was no statistically significant change in relative transcription rates of the Pl1-Rhoades allele between rmr1-1 mutants and heterozygous siblings (FIG. 7). However, transcription rates of anthocyaninless1 (a1), a direct target of the PL1 transcriptional activator [7,19], were ~4-fold greater in rmr1-1 mutants (FIG. 7), reflecting significantly increased PL1 activity. Transcription rates from colored plant1 (b1)—a locus encoding a basic helix-loop-helix factor genetically required for a1 transcription—remained unchanged. These results were recapitulated in comparisons between nuclei isolated from rmr1-3 mutants and heterozygous siblings in which in vitro transcription assays revealed no significant change in transcription rate of Pl1-Rhoades (FIGS. 1A and 7; n=4, two-tailed two-sample t-test, t=0.8, p=0.5) while RNase protection experiments showed a 5.7-fold increase in pl1 RNA for rmr1-3 mutants (FIGS. 1B and 1C; n=2, two-tailed two-sample t-test, t=10.8, p<0.01) using RNA isolated from the same tissues of the same individuals. Similar comparisons from identical tissues but in a different genetic background again showed that transcription rates at pl1 remained unchanged while pl1 RNA levels increased 7.52-fold in rmr1-3 mutants compared to heterozygous siblings (n=1; see).

These RNA expression results sharply contrast those of previous reports using identical in vitro transcription assays that detected significant differences in Pl1-Rhoades transcription rates between Pl' and Pl-Rh states and between rmr6 mutants and non-mutants [8,11]. This indicates our in vitro results represent an accurate assessment of transcription rates and not a limitation of the assay to detect rate differences at the pl1 locus. Combined, these results imply an increase of pl1 RNA abundance disproportionate to insignificant changes in transcription rate in rmr1 mutants, the most direct interpretation being that RMR1 functions at a post-transcriptional level to stabilize Pl1-Rhoades RNA.

Example 2

Rmr1 Encodes a Novel Protein with a Snf2 Domain

To better understand rmr1 function and the paramutation mechanism, we used a map-based approach to identify the rmr1 gene. Using a polymorphic F2 population we looked for genetic linkage between the mutant phenotype and previously mapped chromosome markers [20]. The dark-color phenotype of rmr1-1 homozygotes showed invariant cosegregation with the mutant parent polymorphism of SSLP markers bnlg174a (680 chromosomes tested; <0.15 cM) and npi252 (60 chromosomes tested; <1.7 cM), indicating rmr1 was tightly linked to those markers in bin 6.05 on Chromosome 6. We used the high degree of synteny between this region and rice Chromosome 5 to identify candidate rmr1 orthologs (FIGS. 2A and 2B).

Within the syntenic rice region we identified a gene model, Os05g32610 (http://rice.tigr.org/), predicted to encode a Snf2 protein. The Snf2 protein family is composed of members similar to *Saccharomyces cerevisiae* Snf2p with a bipartite helicase domain containing Pfam SNF2_N and Helicase_C profiles, and includes many proteins involved in ATP-dependent chromatin remodeling [21,22]. While there was no public maize expressed sequence tag for this candidate, we used BLAST searches to identify genomic survey sequence similar to Os05g32610. Oligonucleotide primers were designed from these sequences and used to generate PCR amplicons spanning the maize Os05g32610 ortholog, which were sequenced from individuals homozygous for rmr1 progenitor alleles and mutant derivatives (see Example 5). The maize sequence generated from each of the homozygous mutants revealed single unique transition-type base pair changes consistent with EMS mutagenesis relative to the progenitor (FIG. 2C). The amino acid change associated with the rmr1-1 allele is predicted to prevent proper folding of the helicase domain [23], while the non-conservative amino acid substitutions associated with the rmr1-2 and rmr1-4 alleles occur at highly conserved residues in the SNF2_N profile (FIG. 2D). The rmr1-3 allele is associated with a nonsense mutation predicted to truncate the peptide before the conserved helicase domain (Full rmr1 sequence information is disclosed in GenBank accession numbers EU154999, EU155000, EU155001, EU155002, EU155003, EU155004, and EU155005; SEQ ID NOs: 16-29). CAPS markers were designed to the potential rmr1-1 and rmr1-3 lesions and used to show that the base pair polymorphisms at each of the probable lesions invariably cosegregate with the mutant phenotype (see Example 5). These results support these polymorphisms as bona fide molecular lesions in the rmr1 gene. Based upon molecular genetic mapping data, DNA sequencing results, and the relevance of the fact that Snf2 proteins affect chromatin environments, we conclude the rmr1 locus encodes a protein containing a Snf2 helicase domain.

Os05g32610 gene models and our cDNA sequencing analysis (see Example 5) indicate rmr1 encodes a 1,435-amino-acid protein. In addition to having the conserved Snf2 helicase domain, the protein has a large N-terminal region with no significant identity to any known or predicted proteins. Phylogenetic comparison with other known Snf2 proteins in maize, rice, *Arabidopsis*, and budding yeast shows RMR1 is a member of a Rad54-like subfamily defined by DRD1 (FIG. 3). *Arabidopsis* DRD1 is a putative chromatin remodeling factor affecting RNA-directed DNA methylation (RdDM) patterns [24-26]. In the emerging RdDM pathway model, DNA sequences are targeted for de novo cytosine methylation by complementary siRNA molecules generated from "aberrant" RNA transcripts. The putative MOP1 ortholog in *Arabidopsis*, RDR2, is required in this pathway to presumably generate double-stranded RNA from these transcripts and provide a substrate for siRNA biogenesis through activity of a Dicer-like enzyme [27]. DRD1 is thought to be a downstream effector protein that facilitates de novo methylation of targeted DNA sequences, possibly by modulating chromatin architecture to provide access to de novo methyltransferases [24-26,28]. The DRD1 subfamily also includes the recently identified CLSY1 protein implicated in the systemic spreading of siRNA-mediated silencing in *Arabidopsis* [29].

Multiple sequence alignments (FIG. 8) indicate RMR1 is not the structural ortholog of either DRD1 or CLSY1. The DRD1 subfamily can be divided into three distinct monophyletic groups, with RMR1, DRD1, and CLSY1 defining different groups (FIG. 3). The presumed maize ortholog of DRD1 is likely one of two proteins in the DRD1 subgroup, Chromatin remodeling complex subunit R 127 (CHR127) (http://chromdb.org/), a partial protein predicted from maize expressed sequence tag sequences, or CHR156, a full-length protein predicted from maize genomic sequence (see Example 5). RMR1 is more similar to *Arabidopsis* proteins predicted from At1g05490 and At3g24340. RNA interference knockdowns of these putative *Arabidopsis* orthologs are known to have little to no effect in response to DNA damage [30].

Taking into account the phylogenetic analysis of the predicted coding sequence, it is possible RMR1 function may be similar to, but distinct from, that of DRD1 and CLSY1. The three proteins may fulfill a similar role in RdDM, but perhaps function under different conditions or in distinct genomic contexts. Alternatively, they could perform different roles within an RdDM pathway, or function in separate epigenetic mechanisms altogether. Given the results of our pl1 RNA expression analyses, it is possible that RMR1 represents a Snf2 protein that links chromatin organization to RNA transcript stability.

Example 3

RMR1 Maintains Cytosine Methylation and Small RNA Accumulation at Pl1-Rhoades In the described *Arabidopsis* RdDM pathway, DRD1 maintains cytosine methylation at nonsymmetrical CNN sequences represented by siRNAs [24-26]. Many endogenous genomic targets of DRD1 appear to be repetitive elements [31]. At Pl1-Rhoades there is a 402-bp terminal fragment of a CACTA-like type II DNA transposon, similar to doppia, 129 bp upstream of the translational start site [8,32,33]. Assuming analogous functional roles of RMR1 and DRD1 we compared DNA methylation patterns at this upstream repetitive element in rmr1 mutants and non-mutant siblings.

Previous restriction-enzyme-based comparisons of DNA methylation status between Pl-Rh and Pl' states found no differences, although few 5' proximal sites were evaluated [8]. Using Southern blot hybridization analysis following digestion of genomic DNA with methylation-sensitive restriction enzymes, we found that the doppia fragment is hypomethylated at specific sites in plants homozygous for the rmr1-1 mutation compared to heterozygous wild-type siblings (FIGS. 4A, 4B, and 9). Consistent with findings in *Arabidopsis* RdDM mutants [16, 34-36], the sites hypomethylated in rmr1 mutants were of the CNN context. A relative hypomethylation pattern in 5' sequences is also present in plants homozygous for mutations at either rmr6 or mop1 (FIGS. 10 and 11). In rmr6 mutants the extent of hypomethylation was greater than that of either rmr1 or mop1 mutants and encompassed CG methylation sites as well as non-CG targets, suggesting rmr6 has a broader effect in cytosine methylation maintenance. The presence of these methylation differences in multiple mutant backgrounds indicates that this hypomethylation pattern reflects the chromatin status at doppia in plants where maintenance of repressed paramutant states is compromised.

Consistent with the *Arabidopsis* RdDM model, small RNAs (~26 nt) with sequence similarity to the doppia element are detected in wild-type Pl' plants in both sense and antisense orientations (FIGS. 4D and 12). These small RNAs are undetectable in rmr1 mutants, unlike in wild-type siblings. This result contrasts those in *Arabidopsis* showing that DRD1 deficiencies do not affect the abundance of endogenous siRNAs representing repetitive elements [31]. However, it has been reported that the abundance of endogenous siRNA and trans-acting siRNA populations are highly reduced in CLSY1 mutants [29].

To test if the doppia fragment hypomethylation was indicative of genome-wide changes we assayed the cytosine methylation status at centromeres and 45S repeat sequences. Cytosine methylation patterns were unaffected in either of these regions in rmr1 mutants as compared to non-mutant siblings (FIG. 13). Additionally, we examined the methylation status of doppia-like loci genome-wide (FIG. 4E) and found no obvious differences between rmr1 mutants and non-mutant siblings. These results indicate that while RMR1 acts on the doppia sequence upstream of Pl1-Rhoades, doppia elements appear unaffected throughout the genome. This specificity of RMR1 function may be due to its intimate and exclusive involvement with alleles that undergo paramutation, or may be indicative of differential regulation of repetitive elements depending on their genomic and epigenetic context.

If RMR1 is involved in maintaining cytosine methylation patterns characteristic of repressed paramutant states then a prediction would be that the methylation differences seen between mutants and non-mutants would reflect the Pl' and Pl-Rh regulatory states. Surprisingly, there are no methylation differences at the doppia fragment between Pl-Rh and Pl' states (FIGS. 4C and 14). These results suggest that while the upstream doppia element of Pl1-Rhoades is a target of multiple factors involved in maintaining the epigenetic repression associated with paramutation, the actual process of paramutation does not result in similar changes of DNA methylation at this element.

Example 4

RMR1 Is Not Required for Establishment of Paramutant States

Based on a reverse transcriptase PCR (RT-PCR) expression profile (FIG. 15) rmr1 appears to be expressed in all rapidly dividing somatic tissues, consistent with a role in maintaining paramutant states throughout development. However, since the methylation patterns maintained by RMR1 appear unrelated to the paramutant state of Pl1-Rhoades, we questioned whether RMR1 is directly required for paramutation to occur. This process results in the invariable establishment of the Pl' state in Pl'/Pl-Rh plants, as evidenced by the observation that only Pl'/Pl' progeny are found when Pl'/Pl-Rh plants are crossed to Pl-Rh/Pl-Rh testers [7,8]. If RMR1 were directly involved in this process we would expect that an rmr1 deficiency might interfere with the Pl' establishment event. To test this, we tracked the behavior of individual Pl1-Rhoades alleles in test crosses to assess the ability of the Pl' state to facilitate paramutations in Pl'/Pl-Rh; rmr1-1/rmr1-2 plants. The Pl1-Rhoades allele in a Pl-Rh state was genetically linked (~1.5 cM) to a T6-9 translocation breakpoint. The T6-9 interchange can act as a dominant semi-sterility marker, allowing us to trace specific Pl1-Rhoades alleles through genetic crosses [11]. rmr1 mutants heterozygous for the T6-9 interchange (T6-9 Pl-Rh/Pl') were crossed to a Pl-Rh/Pl-Rh tester (FIG. 5; Table 1). If establishment of the Pl' state was prevented in rmr1 mutants, we would expect all progeny receiving the interchange to display a Pl-Rh/Pl-Rh phenotype (dark anther pigmentation). We observed that over half the progeny inheriting the interchange displayed a Pl'/Pl'-like phenotype (light anther pigmentation), indicating that paramutation was established in the rmr1 mutant parent. It should also be noted that Pl-Rh/Pl-Rh plants, and those of an intermediate phenotype of partial pigmentation [7], were present in both progeny inheriting the interchange and those inheriting a normal chromosome. These results are consistent with previous work showing Pl' can revert to a Pl-Rh state in rmr1 mutants [10].

Corresponding analysis of the establishment of paramutant states at the b1 locus generated similar results (Table 2). The repressed B' state of the B1-Intense allele [37] was established in B'/B-I rmr1 mutants greater than 95% of the time. While it is possible that rmr1 defects affect establishment efficiency, it will be difficult to differentiate any such effects from its clear role in maintenance [11]. These results point to an interesting duality in RMR1 function in which the wild-type protein is necessary for meiotic heritability of repressed epigenetic states, but is not required to establish these states. This duality is markedly different from results generated in the analysis of DRD1, which was shown to be necessary for the maintenance, establishment, and removal of repressive epigenetic marks [24,25].

Example 5

Materials and Methods

Scoring of the Pl1-Rhoades Allele Expression State and Rmr Mutants

Plants were scored as carrying Pl-Rh or Pl' states through visual inspection of anther pigmentation and assignment of an anther color score as previously described [7]. Pl'/Pl' (anther color score 1 to 4) anthers show little to no pigmentation while Pl-Rh/Pl-Rh (anther color score 7) anthers are dark red to purple. Mutants were scored in the same way, with rmr and mop mutants showing a Pl-Rh/Pl-Rh-like phenotype, except in the case of the F2 rmr1 mapping populations, in which mutants were chosen on the basis of a dark seedling leaf phenotype [10].

Genetic Stocks

Elite inbred lines (B73, A619, and A632) were provided by the North Central Regional Plant Introduction Station (http://www.ars.usda.gov/main/site_main.htm?modecode=36-25-12-00). Color-converted versions of A619 and A632 inbred lines were created by introgressing the Pl1-Rhoades allele into each [11]. The rmr1-1, rmr1-2, mop1-1, and rmr6-1 alleles have been previously described [8,10,13]. The rmr1-3 allele was derived from identical materials used to isolate rmr1-1 and rmr1-2; rmr1-4 was derived from EMS-treated pollen from an A619 color-converted line applied to a color-converted A632 line [11] (see Table 3 for complementation tests). The T6-9 translocation line carrying the Pl1-Rhoades allele used in Pl' establishment tests has been described previously [11].

Pl1 Expression Analyses

Figure 1:
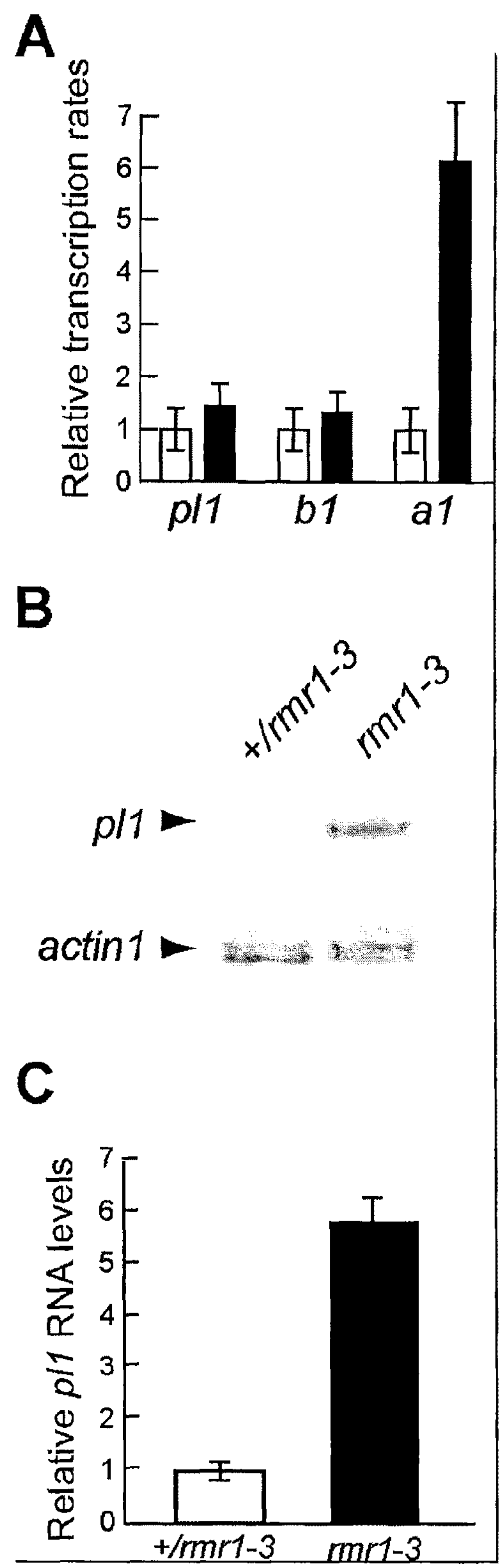
FIG. 1: Comparison of pl1

In vitro transcription assays (rmr1-1 and rmr1-3; FIGS. 1 and 7) and RNase protection assays (rmr1-3 only; FIG. 1) were carried out as described [8] with husk nuclei and RNA isolated from single ears of the same genetic stocks used to measure pl1 RNA differences in rmr1-1 anthers [10]. The b1 and pl1 genotypes of these plants are as follows: B-Intense (B-I)/B-I, Pl1-Rhoades (Pl') rmr1/Pl' rmr1-1 and B-I/B-I; Pl' rmr1-1/Pl' rmr1-1, or B-I/B-I, Pl' rmr1/Pl' rmr1-3 and B-I/B-I; Pl' rmr1-3/Pl' rmr1-3. Identical procedures were applied to single ears from plants homozygous for Pl' and either homozygous or heterozygous for rmr1-3 following a single backcross into the KYS inbred line [12].

Genetic Mapping of Rmr1

A F2 mapping population was created from inbred (S9) rmr1-1/rmr1-1, Pl'/Pl', and color-converted A632 inbred (Pl'/Pl', >93% A632) parents. DNA was isolated using the DNeasy 96 plant kit (Qiagen, http://www1.qiagen.com/) from F2 mutant seedlings, mapping parents, and F1 hybrid leaf tissue. These DNA samples were screened with SSLP markers developed from the Maize Mapping Project (http://www.maizemap.org/; US National Science Foundation award number 9872655; primer sequences and protocol available at http://maizegdb.org/). Initial marker choice was restricted to Chromosomes 6 and 9 because of linkage of rmr1 to a T6-9 breakpoint. In addition to the rmr1-1 mapping population, a second F2 mapping population created with inbred (S7) rmr1-3/rmr1-3, Pl'/Pl', and color-converted A632 parents showed similar cosegregation with marker bnlg1174a (178 chromosomes tested; <0.56 cM). CAPS [61] markers were designed to test cosegregation of the rmr1-1- and rmr1-3-associated lesions with the rmr1 mutant phenotype. No recombinant chromosomes (876 chromosomes tested for rmr1-1,268 chromosomes tested for rmr1-3) were found using either marker.

Candidate Gene Selection and Sequencing

A BLAST search using the rice Os05g326100RF as a query identified maize GSS and sorghum expressed sequence tag sequences that were used to generate a contig representing the putative maize gene (see Candidate Gene Selection and Sequencing section below for sequence identifiers). Oligonucleotide primers (Sigma-Genosys, http://www.sigmaaldrich.com/Brands/Sigma_Genosys.html) were designed from these sequences and used in PCR amplification of genomic DNA from three separate individuals homozygous for each rmr1 mutant allele as well as functional reference alleles rmr1-B73, rmr1-A632, and rmr1-A619. PCR amplicons were purified using QIAquick gel extraction kit (Qiagen) and dideoxy sequenced (UC Berkeley DNA Sequencing Facility, http://mcb.berkeley.edu/barker/dnaseq/). To verify the intron/exon structure of rmr1, cDNA was generated from rmr1-1 mutants as well as non-mutant B73 plants as described [15], and rmr1 was amplified via RT-PCR. The resulting products, which were the predicted size for spliced rmr1 transcript, were sequenced to validate the intron/exon structure shown in FIG. 2. See Table 4 for oligonucleotide primer sequences used (SEQ ID NOs: 30-46).

Phylogenetic Analysis

Sequencing reads from genomic and cDNA were aligned and edited with Sequencer (Gene Codes, http://www.genecodes.com/) to create a contig representing rmr1. The N-terminal prediction is based on alignment of RMR1 with the protein model for Os05g32610. A search of the Pfam database (http://www.sanger.ac.uk/Software/Pfam/) with the predicted RMR1 protein sequence was used to identify the conserved SNF2_N and Helicase_C protein profiles of the Snf2 helicase domain. MUSCLE [62] was used to generate an alignment between RMR1 and proteins from *Arabidopsis*, rice, maize (CHR127 and CHR156), and budding yeast over the helicase domain (FIG. S2). Sequences for CHR127 and CHR156 were retrieved from ChromDB (http://www.chromdb.org/). Additional sequence information for CHR156 was identified from BAC CH201-3L17 (GenBank accession AC194602), and gene model prediction was performed using FGENESH+ (Softberry, http://www.softberry.com/) with RMR1 as similar protein support. A distance tree was created and bootstrap values were calculated using PAUP* 4.0 from the above alignment (Sinauer Associates, http://www.sinauer.com/).

Southern Blot Analysis

Genomic DNA was isolated as described [63] from the terminal flag leaves of adult plants segregating for rmr1, rmr6, and mop1 mutants and heterozygous siblings as well as Pl' and Pl-Rh plants as assayed by anther pigmentation [7,8,10, 13]. Restriction digest and subsequent Southern blots were carried out as previously described [13], using the restriction enzymes listed in FIG. 4 (New England Biolabs, http://www.neb.com/). The probes specific to pl1 are shown in FIG. 4; the 45S and centromere probes are as described [13].

Small RNA Northern Blots

Small RNAs were prepared from 10-mm immature ear tissue and used to generate small RNA northern blots as previously described [64]. In FIG. 4D the small RNAs were run with a 27-bp DNA oligonucleotide containing doppia sequence that hybridized with the riboprobe used to identify the small RNAs. The riboprobe was synthesized as described [64] from a plasmid containing the region denoted probe B in FIG. 4A linearized at an AseI site so as to contain only doppia sequence.

Pl' Establishment Tests

Establishment of the Pl' state in rmr1 mutants was assayed essentially as described previously [11]. When the T6-9 interchange pair is heterozygous with structurally normal chromosomes, the plants display ~50% pollen sterility due to meiotic-segregation-induced aneuploidy in the resulting gametes. Pollen sterility was assayed in the field using a pocket microscope. rmr1 mutants were crossed to Pl-Rh/Pl-Rh A619 or A632 inbreds (Table 1), and the resultant progeny were scored with respect to Pl1-Rhoades expression state.

Complementation Tests of New Mutant Alleles

Complementation test results (Table 3) show ems98292 and ems98941 mutations define alleles of mop1 and that ems98287 and ems051069 mutations define alleles of the rmr1 locus. The ems98287, ems98292, and ems98291 mutations were isolated using an ems pollen mutagenesis and genetic screening strategy as previously described. The ems051069 mutation was similarly generated and isolated using color converted A619 and A632 inbred parental lines.

Homozygous ems98262/ems98262 plants having a Pl-Rh-like phenotype (ACS 7) were outcrossed to Pl'/Pl' testers. All F1 progeny plants (39 individuals from 3 independent outcrosses) had a Pl'-like anther phenotype (5 ACS 1; 22 ACS 2; 12 ACS 3) indicating the ems98262 allele is recessive and further that Pl' alleles transmitted from homozygous ems98262/ems98262 plants are capable of inciting paramutation. The Pl-Rh-like anther phenotype was recovered in 10/62 F2 plants derived from three independent self-pollinations of F1 plants (30 ACS 1; 15 ACS 2; 2 ACS 3; 10 ACS 7). The observed frequency of Pl-Rh-like phenotypes (16%) is not significantly different from the 25% expected from a single locus recessive mutation (Pearson's goodness of fit x2=0.28; P=0.59). All F2 progeny with ACS 7 anthers were ~⅔ the height of their Pl'-like siblings. Five of the 62 F2 progeny produced barren (no flowers) tassels so it was not possible to assign these to a given Another Color Score class. However, these five anther-less progeny were short in stature and had very strong plant color similar to all other F2 plants that had ACS 7 anthers. If we include these five anther-less progeny among the "ACS 7" mutant class, then 15/62 (24%) of the F2 progeny have the mutant phenotype. These F2 segregation ratios are consistent with the hypothesis that the dark-anther and dark-plant phenotypes are due to a single locus recessive mutation. Homozygous ems98941/ems98941 plants having a Pl-Rh-like phenotype were outcrossed to Pl'/Pl' testers. All F1 progeny plants (14 individuals from 2 independent outcrosses) had a Pl'-like anther phenotype (2 ACS 1; 9 ACS 2; 2 ACS 3; 1 ACS 4) indicating that the ems98941 allele is recessive and further that Pl' alleles transmitted from homozygous ems98941/ems98941 plants are not recalcitrant to subsequent paramutation.

Results of genetic crosses (Table 3) indicate the ems98262 and ems98941 mutations complement mutations at rmr1, rmr2 and rmr6. However, the two mutations fail to complement each other and the mop1-1 mutation. If the ems98262 mutation represents an allele of mop1, then ½ of all progeny (14-15 individuals) from the two complementation crosses with mop1-1 should have a Pl-Rh-like anther phenotype. The observed frequency of Pl-Rh-like types is not significantly different from the expected frequency for this hypothesis (Pearson's goodness of fit x2=3.07; P=0.08) suggesting ems98262 defines an allele of mop1 hereafter designated mop1-3. If the ems98941 mutation defines an allele of mop1, then 50% of the complementation cross progeny made with mop1-1 (9-10 individuals) should have a Pl-Rh-like anther phenotype. The observed frequency is not significantly different from this hypothesis (Pearson's goodness of fit x2=0.67; P=0.41) suggesting ems98941 defines an allele of mop1 hereafter designated mop1-4. These assignments are consistent with the complementation results of mop1-3 heterozygotes crossed by mop1-4 homozygotes (Table S3). If the two mutations represent alleles of mop1, then ½ of all progeny (13 individuals) from the two complementation crosses should have a Pl-Rh-like anther phenotype. The observed frequency of Pl-Rh-like types is not significantly different from the expected frequency for this hypothesis (Pearson's goodness of fit x2=2; P=0.16).

Plants homozygous for the ems98287 mutation, having a Pl-Rh-like phenotype, were outcrossed to Pl-Rh/Pl-Rh plants. Almost ½ of F1 plants (8 of 25 individuals from two independent outcrosses) had a Pl-Rh anther phenotype (2 ACS 1; 12 ACS 2; 2 ACS 4; 1 ACS 5; 8 ACS 7) suggesting ems98287 might represent a dominant mutation. However, the Pl-Rh-like phenotype was recovered in 12/40 (30%) F2 plants derived from two independent self-pollinations of ACS 3 F1 plants (3 ACS 1; 19 ACS 2; 5 ACS 3; 1 ACS 4; 12 ACS 7). The observed frequency of F2 mutant phenotypes (30%) is not significantly different from the 25% expected from a single locus recessive mutation (Pearson's goodness of fit x2=0.25; P=0.62) and is consistent with the hypothesis that the dark-anther phenotype, is due to a single locus recessive mutation. Complementation test results (Table 3) indicate the ems98287 mutation complements mutations at rmr2, rmr6, and mop1. If the ems98287 mutation was an allele of rmr1, then ½ of all progeny (24-25 individuals) from the two complementation crosses should have a Pl-Rh-like anther phenotype. The observed frequency of Pl-Rh-like types (20/49) is not significantly different from the expected frequency for this hypothesis (Pearson's goodness of fit x2=0.83; P=0.36), suggesting the ems98287 and rmr1-1 mutations define the same locus. Subsequent molecular mapping of the ems98287 mutation also placed it in the same position as rmr1-1 (bin6.05) thus allowing us to conclude that ems98287 defines an allele of rmr1 hereafter designated rmr1-3.

Using color-converted A619 and A632 inbred lines [2], EMS pollen mutagenesis [1] was repeated and M2 families were screened for the appearance of plants with darkly colored anthers. In separate growouts, the M2 progeny designated 34833 segregated 5/27 plants with ACS 7 anthers. This frequency is not statistically different from the 25% expectation for a single locus recessive mutation (Pearson's goodness of fit x2=0.33; P=0.56) plants with ACS 7 anthers. Pollen from a single ACS 7 plant was used for genetic complementation crosses. This mutation (ems051069) fully complemented mutations defining mop1, rmr2 and rmr6 but failed to complement both rmr1-1 and rmr1-3 (Table S3). If the ems051069 mutation represents an allele of rmr1, then ½ of all progeny (26-27 individuals) from the two rmr1 complementation crosses should have a Pl-Rh-like anther phenotype. The observed frequency of Pl-Rh-like types (28/53) is not significantly different from the expected frequency for this hypothesis (Pearson's goodness of fit x2=0.08; P=0.77), suggesting the ems051069 mutation defines the same locus. The allele defined by the ems051069 mutation is hereafter referred to as rmr1-4.

Pl' Establishment Tests

Table 1 details crosses done to generate families for genetic tests used to determine the effect of rmr1 mutations on establishment of Pl' states. Families 05-541 and 05-542 were segregating Pl' rmr1-1/T6-9 Pl-Rh rmr1-2 plants (FIG. 4). These plants were selected using the dark anther mutant phenotype and then crossed to or by a Pl-Rh homozygous tester. Plants in families 05-103 and 05-539 are the color-converted A632 and A619 testers respectively. The structural genotype (presence or absence of the T6-9 interchange pair) was scored in the field by assaying pollen fertility. The state of the Pl1-Rhoades allele was assayed by evaluating anther pigmentation on a 1 to 7 scale as previously described. Plants with an ACS of 1-4 (representing the Pl'/Pl' phenotype) are referred to as having light anthers, plants with an ACS of 7 (representing the Pl-Rh/Pl-Rh phenotype) are referred to as having dark anthers, and plants with an ACS of 5-6 phenotype are described as intermediate (FIG. 5).

B' Establishment Tests

To test the role of rmr1 in b1 paramutation, isogenic B-I and B' stocks (B1-I; Pl'-Rhoades) were first pollinated by rmr1-1/rmr1-1; b1-W23/b1-W23; Pl1-Rhoades/Pl1-Rhoades plants. Intercrossing the resulting F1 plants (B-I/b1-W23×B'/b1-W23) gave rise to progenies in which there was segregation of Pl-Rh-like and Pl'-like plants. Among these Pl-Rh-like plants, the following b1 genotypes occurred at a 1:1:1:1 frequency: b1-W23/b1-W23; b1-W23/B'; b1-W23/B-I; B-I/B'. Blind test crosses of parental plants displaying dark plant colors (rmr1-1/rmr1-1) were made to b0-CO159/b1-CO159 pistillate testers (Pl-Rh/Pl-Rh; C0159/W23 stock). Actual b1 genotypes of the staminate parents were assigned ex post facto based on segregation of plant color types among resulting test cross progenies (Table 2). An identical strategy using rmr6 mutations has been described.

In Vitro Transcription Reactions

This was carried out as described with husk nuclei isolated from single ears of the same genetic stocks used to measure pl1 RNA differences in anthers (FIG. 7). The anthocyanin genotype of these plants is B1-I (B-I)/B1-I (B-I); Pl1-Rhoades (Pl') Rmr1/Pl1-Rhoades (Pl') rmr1-1 and B1-I (B-I)/B1-I (B-I); Pl1-Rhoades (Pl') rmr1-1/Pl1-Rhoades (Pl') rmr1-1. The same procedure was applied to single ears of B1-I (B-I)/B1-I (B-I); Pl1-Rhoades (Pl') Rmr1/Pl1-Rhoades (Pl') rmr1-3 and B1-I (B-I)/B1-I (B-I); Pl1-Rhoades (Pl') rmr1-3/Pl1-Rhoades (Pl') rmr1-3 plants with the following results: four biological replicates pl1, 1.4+/−0.4; b1, 1.3+/−0.6; a1, 6.2+/−1.2 (mean difference+/−s.e.m.).

Alignment of the Helicase Domain of RMR1 with Other Known and Predicted Snf2 Protein Family Members MUSCLE was used to generate the alignment of the Snf2 helicase domains. The alignment figure (FIG. 8) was shaded with GeneDoc 2.6.03 using a combination of manual and identity modes, with RMR1 being selected as the identity comparison sequence. The lightest level of shading represents conserved residues in at least 60% of the sequences, the middle level is conserved residues is at least 80% of the sequences, and the darkest level is amino acid identity in all sequences.

RT-PCR Expression Analysis

Fully expanded adult leaf (fourth node), flag leaf (terminal leaf), immature tassel, and immature ear tissue was harvested from an adult B73 elite inbred plant 83 days post-germination (FIG. 11). Seedling leaf tissue was harvested from a non-mutant seedling from the F2 rmr1-1 mapping population 10 days post-germination. Seedling root tissue was harvested from a non-mutant seedling from the F2 rmr1-3 mapping population 10 days post-germination. Shoot apical meristem tissue was collected from a seedling (color converted A619 stock) 10 days post-germination. RNA was isolated from the above tissues using TRIzol reagent (Invitrogen, Carlsbad, Calif.) and following the manufacturer's protocol. 10 μg of total RNA was treated with DNase I (Invitrogen) and then reverse transcribed using SuperScript II reverse transcriptase (Invitrogen) and Oligo dT(17) primers (Promega). The resulting cDNA was PCR amplified using rmr1 specific primers Os11F and Os15R (Table 4). RT-PCR products sized on a 1% agarose gel and stained with ethidium bromide for visualization. Amplifications of rmr1 from cDNA yields a 640 bp product, while amplification of rmr1 from genomic DNA generates a 2663 bp product (not shown). RT-PCR was also carried on the cDNA using primers specific to alanine aminotransferase (aat) to ensure equal starting amounts of RNA. Amplification of aat cDNA generates a 281 bp product and amplification from genomic DNA produces a 454 bp product. The DNA control was isolated from a color-converted A632 plant as described previously.

Genetic Mapping of Rmr1

The CAPS marker for rmr1-1 was identified by PCR amplifying genomic DNA from the mapping population with primers 1CAPS6F and 1CAPS6R (Table 4) and digesting the product with PvuII (NEB, Ipswich, Mass.). Digested samples represent individuals with the non-mutant polymorphism. For the rmr1-3 population, (134 individuals, 268 chromosomes scored) the primers were 1CAPS10F and 1CAPS10R, the restriction enzyme was BclI (NEB, Ipswich, Mass.), and digested samples represent mutant individuals. No recombinants were found with either marker.

Candidate Gene Selection and Sequencing

See Table 4 for all oligonucleotide primer sequences used. A BLAST search using the rice Os05g326100RF as a query identified maize GSS sequences CG886593, BZ668661, BZ681915, CZ392826, BH878936, CG882444 and sorghum EST sequences AW287235, BG322766, AW285838, BG323020. Sequence was generated for rmr1 from PCR amplicons from various primer pairs. The Os10F/Os10R primer pair amplified sequence identifying the rmr1-3 lesion, and the exonF/exonR amplicons contain the rmr1-1, rmr1-2 and rmr1-4 lesions. To verify the intron/exon structure of cDNA amplified across intron 1 with primers Intron0 F2/Intron0 R2, and across introns 2 and 3 with primers Os11F/Os15R. Additional sequence information was provided by the following primers: mid5'F, Os12F, Os13Rb, intronF, and intronR.

Small RNA Northern Blots

The blots shown in FIG. 8 were carried out as described in the Materials and Methods of the main text with the exception that the DNA oligonucleotides used did not contain doppia sequence, meaning the blots had to be striped and rehybridized with the complementary oligos end-labeled with polynucleotide kinase (Fermentas, EK0031) for accurate sizing.

Example 6

Discussion

RMR1 is the first protein identified whose function acts to maintain trans-generationally repressed states associated with paramutation, a genetic behavior that affects meiotically heritable epigenetic variation through allelic interactions at endogenous loci. The identification of RMR1 as a Snf2 protein highlights an emerging role of these proteins in establishing and maintaining epigenetic marks. In *Arabidopsis* the Snf2 proteins DRD1 and DDM1 [38,39] are known to maintain cytosine methylation patterns. Lsh1, the mammalian protein most closely related to DDM1, is also required for normal DNA methylation patterns [40-42]. There are some 42 Snf2 proteins in *Arabidopsis* and at least as many in maize (http://chromdb.org/). This diversity likely represents great functional specialization amongst these proteins. We have placed RMR1 in an RdDM pathway based on its helicase domain similarity to DRD1 and the recent identification of MOP1 as an RDR2 ortholog [14,15]. Consistent with this proposed pathway, the rmr1 mRNA expression profile (FIG. 15) closely matches that of mop1 [15]. Additionally, both RMR1 and MOP1 are necessary to maintain cytosine methylation patterns at silenced transgenes [43], the Pl1-Rhoades doppia sequences, and certain Mutator transposable elements ([15, 44]; J. B. H. and D. Lisch, unpublished data). DRD1 is also known to target repetitive elements found in euchromatic contexts through an RdDM pathway [31]. However, the role RMR1 plays to maintain the repressed paramutant states at Pl1-Rhoades appears different than the function of DRD1 in the *Arabidopsis* RdDM pathway, as RMR1 has, in addition to its requirement for CNN methylation at doppia, a role in the normal accumulation of small RNAs with similarity to that element.

It is unclear how RMR1 mediates the post-transcriptional regulation of pl1 transcripts as suggested by the in vitro transcription and RNase protection assays reported here. It is possible that pl1 transcripts resulting from Pl1-Rhoades in the Pl' state are less stable than those produced from the Pl-Rh state because of differences in the chromatin environment of Pl1-Rhoades. However, there do not appear to be any Pl'-specific small RNAs produced from the pl1 coding region [12]. In *S. pombe* it has been shown that the chromatin environment of a locus can affect RNA transcript levels without altering RNA polymerase II occupancy of that locus, leading to the proposal of a cotranscriptional gene silencing mechanism whereby nascent transcripts initiating in a heterochromatic environment are degraded by complexes targeted via heterochromatic small RNAs [17,18]. Chromatin differences in the upstream region of Pl1-Rhoades may favor recruitment of alternative RNA-processing factors or RNA polymerases, which in turn influence the stability of pl1 transcripts. In plants, localization of the large subunit 1a of RNA polymerase IV to loci targeted for RdDM appears necessary for the biogenesis of siRNAs from these loci [28]. When Pl' repression is disrupted in rmr1 mutants, this alternate genesis or processing of the pl1 transcript may also be lost. Alternatively, our results may highlight a novel role for RMR1-like Snf2 proteins in directly interacting with nascent RNA transcripts via a helicase domain, or in recruiting factors that directly destabilize these transcripts.

Importantly, our analysis of rmr1 mutants calls into question the relationship between RMR1 function and the mechanism of paramutation at Pl1-Rhoades. The mutational screens identifying rmr1, rmr6, and mop1 were designed to discover genetic components necessary to maintain the repressed state of Pl', not necessarily factors needed to establish this repressed state [10,13]. Therefore, it is possible that loci thus far identified may be indirectly related to the paramutation mechanism. Our results are consistent with a model wherein RMR1 functions in an RdDM pathway, along with an RDR2-like enzyme, MOP1, to maintain a persistent heterochromatic-like chromatin structure at the repetitive element found directly upstream of the pl1 coding region. While it is not clear where RMR1 acts in this pathway it presumably acts coordinately with the maize orthologs of known RdDM components identified in *Arabidopsis*, namely DCL3 [16,45], the DRM methyltransferases [36], AGO4 [46,47], the RNA polymerase IV subunits, and the maize DRD1 ortholog (FIG. 6A). In this model, doppia transcripts, perhaps because of the repetitive nature of the doppia genomic elements and/or the numerous internal subterminal repeats that are present in these elements [32,48], are the source of aberrant RNA that is processed via MOP1 and a DCL3 enzyme into siRNAs. This small RNA production is carried out in a manner that is dependent on RMR1 activity, possibly via direct interaction with a small RNA processing complex or by making the DNA accessible to factors necessary for siRNA precursor generation such as polymerase IVa. These siRNAs, through the activity of AGO4, DRM enzymes, and polymerase IVb, then establish a heterochromatic state at the Pl1-Rhoades doppia-like element that is present in both Pl-Rh and Pl' states. The methylation effects seen in rmr1 mutants might indicate that this heterochromatization machinery depends on the activity of RMR1 to feed back on the doppia element, or loss of RMR1 may short circuit this pathway and thus affect methylation activity indirectly. An RMR1 defect then affects stability of paramutant states at pl1 because of the chromatin context of the Pl1-Rhoades allele, and not through direct disruption of components required for paramutations to occur. This is in line with a report that MOP1-dependent small RNAs produced at the b1 locus are insufficient to mediate paramutation [49].

The relationship between RMR1 action, the chromatin organization of Pl1-Rhoades, and the repressed Pl' state is not clearly understood at this time. It is possible that derepression of the upstream repetitive element makes the region more accessible to general transcription factors whose actions could destabilize repressive Pl' chromatin states that are independent of those maintained at doppia (FIG. 6A). Indeed, RNA polymerase processivity can lead to changes in the chromatin environment through histone modifications or histone replacement [50,51]. Alternatively, Pl' chromatin states may represent a spreading of the heterochromatic domain at doppia into a euchromatic region defined by the Pl1-Rhoades gene space (FIG. 6B). In fission yeast, heterochromatic domains nucleated by small RNAs have the ability to spread in cis through successive H3 K9 methylation [52]. In this situation, loss of RMR1 function would alleviate Pl' repression by disrupting maintenance of this expanded heterochromatic domain. In either of these situations RMR1 affects Pl1-Rhoades paramutations by virtue of its role in maintaining heterochromatic states at a proximal repetitive element.

McClintock was the first to describe derivative alleles in which transposons acted to control the expression patterns of attendant genes [53]. It is now clear that epigenetic modulations of the transposons themselves—what McClintock referred to as "changes in state"—can alter the regulatory properties of individual genes both somatically [54] and trans-generationally [55,56]. Our results indicate that even transient changes in state of the Pl1-Rhoades doppia fragment can have trans-generational effects on pl1 gene expression patterns. These experimental examples, in the context of McClintock's thesis [53], point to a dynamic source of regulatory, and potentially adaptive, variation adjunct to the DNA itself. Precisely how this epi-variation relates to existing genome structure and function, as well as its evolutionary potential, remains a largely unexplored area of investigation.

Currently, well-characterized examples of paramutation are limited to loci where expression states have a clear phenotypic read-out, such as pigment synthesis. cis-Elements required to facilitate paramutation have been functionally identified at specific alleles of b1 and colored1 (r1) [57-59]. To date, there is no evidence that the chromatin status of these cis-elements is affected by mutations at trans-acting loci required for maintenance of repressed paramutant states. It appears that paramutations represent a type of emergent system wherein genomic context and maintenance of chromatin states interact to facilitate meiotically heritable epigenetic variation. In this view, it is possible that cis- and trans-elements necessary for maintenance of such variation might not interact in a direct and predictable manner. What remains to be seen is the extent to which this type of system acts throughout the genome. Genome-wide screens for paramutation-like behavior, in which expression states are affected by allele history, remain technologically and conceptually challenging. Recent work by Kasschau et al. [60] suggests that in *Arabidopsis*, few endogenous genes are regulated by proximal presumed RdDM targets. However, it is tempting to speculate that examples of paramutation represent an exception to this trend, representing a mechanism by which populations can quickly, and heritably, change their transcriptome profile and regulation.

Example 7

RMR1 Function Contributes to Inbreeding Depression

Our genetic and molecular studies show that Pl1-Rh favors a reduced activity state when maintained in homozygous condition [9] and that a RdDM/CTGS pathway involving RMR1 maintains this repressed state [65]. If significant numbers of alleles show behaviors similar to Pl1-Rh, then inbreeding could lead to widespread genetic repression affecting plant growth, development and homeostasis. The fact that rmr1 mutants have vastly reduced levels of genome-derived ~24 nt RNAs (FIG. 16) suggests many alleles that would otherwise be repressed by the RMR 1-dependent pathway would remain active. Hence inbreeding syndromes might be mitigated to some extent in rmr1 mutant lineages. For initial genetic mapping, the rmr1-1 mutation was crossed to the A632 inbred and recovered in homozygous condition from an F2 family. Three lines of single seed descent were initiated in the S1 progeny and it was surprising to find that plant quality remained fairly consistent in S2-S11 generations; silking and anthesis remained coincident, pollen shed remained copious with no evidence of aborted grains above the typical ~5% level, plant morphology appeared unaffected aside from mild stunting, and seed set was consistently full. This was unexpected as, in our experience, typically few recombinant inbred lines remain suitable for propagation past the S4 generation and most other rmr-class mutants display severe degradations in plant quality upon selfing [13, 66; J Hollick, unpublished]. As a control, parallel lines were developed from S1 progeny of a single Rmr1-A632/rmr1-1 individual from the same initial F2 mapping progeny in order to compare inbred Rmr1-A632/Rmr1-A632 versus rmr1-1/rmr1-1 genotypes. At the S5 generation, lines of both genotypes were planted in adjacent plots and visually evaluated for general plant characters and subsequent seed set on selfed ears. Plants from the four established rmr1-1/rmr1-1 lines were uniform and unremarkable in type, and selfed ears from all 39 plants had near full seed set. In contrast, 9 of 24 plants from the two Rmr1-A632/Rmr1-A632 lines (3/9 and 6/13 off-types in the respective lines) were phenotypically abnormal. Four of these 9 off-types were classified as "runts" as their heights were less than ~⅓ of their siblings and one of these had conspicuously narrow leaf blades. None of these four runts produced silking ears. Four plants had delayed silking relative to pollen shed; two of these plants produced tiny ears with no grains and two plants had normal sized ears with only a single grain each. One otherwise normal plant had vestigle apical leaves and no apical inflorescence. Thus only ~55% of the inbred plants with normal RMR1 function were phenotypically normal but all the inbred plants derived from the four founder rmr1-1/rmr1-1 mutants were of good quality similar to that seen in the original set of S2-S11 rmr1-1/rmr1-1 lines. These observations combined suggest that loss of RMR1 function helps prevent the degradation of plant quality typically seen in inbreeding depression.

Example 8

The Rmr1-1 Mutation Affects Transgressive Traits Manifest in Heterotic Crosses As heterosis and inbreeding depression are often thought to be opposite manifestations of a fundamentally similar genetic relationship, it seemed reasonable to test whether or not preconditioned epigenomes (+/−RMR1 function) would respond differentially in heterotic crosses. Two ears from the same A632, Mol7, or B73 plants were differentially pollinated using single pollen sources from S4 Rmr1-A632/Rmr1-A632, and S4 rmr1-1/rmr1-1 plants and small progenies (16-20 individuals) were evaluated for several traits including dry ear weight. Results of this initial test were striking (Table 5) as at least one non-anthocyanin trait was differentially affected in every cross. Most significant was the observation that dry ear weight was nearly 10% greater when the single B73 parent received pollen from the rmr1-1 line versus the Rmr1-A632 line. There are at least two major experimental concerns with this exciting result. First, this simple measurement does not control for differences in grain moisture and includes the cob, typically discarded in such yield evaluations. Secondly, and most problematic, the contrasting lines are only ~75% genetically identical. Ideally, these tests would use nearly isogenic parents (see Example 12).

These two sets of preliminary data regarding the differential breeding behaviors of rmr1-1/rmr1-1 and Rmr1-A632/Rmr1-A632 plants are consistent with a hypothesis in which genomes conditioned in the presence or absence of RMR1 function have unique epigenomic landscapes that dictate differential genic action or dynamic responses. Published data regarding Pl1-Rh action validates this hypothesis at a single locus level.

Example 9

Evaluate Rmr1 Knockdown (KD) Approaches to Mitigate Transgene Silencing

RNAi-based strategies will be tested on existing silenced transgenes and newly developed GFP/GUS reporter constructs in transgenic maize plants. Given the observations that rmr1-1 mutations are able to release transcriptional repression of a silenced 35S-B 1 transgene array [43], it is quite likely that RNAi-based knockdown (KD) lines of rmr1 RNA could be broadly employed to mitigate, or control, transgene silencing for commercial application. The fact that RMRI defects themselves appear not to affect plant development [10] suggests that such KD strategies can complement existing breeding programs without compromising biomass yields. As an experimental overview, CAMBIA-based vectors will be used to create both RMR1 KD and promoter-GFP reporter constructs, and fertile transgenic maize lines will be established to compare effects of RMR1 on existing and de novo reporter gene silencing.

Create and Validate Rmr1 Knockdown Lines

We will generate public lines that can be used to release and control transgene silencing. The NSF-sponsored maize chromatin consortium (NSF DBI-0421679; www.chromdb.org) has had good success using bioinformatics and subsequent double-stranded RNA (dsRNA) based constructs to molecularly knock-down RNA expression of specific endogenous maize genes even when they belong to multigene families ([43]; 26 individual genes validated for molecular KD phenotypes). Unfortunately, rmr1 was not among the ChromDB KD targets since it was, to this point, not represented in available EST collections. The pMGC161 vector and cloning technology developed in the maize chromatin consortium will be used to create a dsRNA expression construct specific for rmr1 (double CaMV35S promoter driving an inverted repeat of −1 kb of Rmr1 exon3 separated by a *O. sativa* waxy1 intron stuffer). Recombinant DNA manipulations will be carried out in *E. coli* and the sequence-validated construct will be electroporated into *A. tumefacians* strain EHA101. With appropriate APHIS permit, a transformed Agro strain will be shipped to the Iowa State Plant Transformation Facility (PTF) for maize (Hill line) transgenesis. We will request that PTF provide seeds from 8 separate glufosinate-resistant transformation events. Transgene-based effects on endogenous Rmr1 RNA levels will be assayed using RT-PCR, and Southern blotting will be employed to characterize insert structures for those plants demonstrating a molecular KD phenotype. Agro-mediated transformation will be chosen to establish these lines as there is a greater chance for single inserts of low transgene complexity that, in general, tend to escape gene silencing. If Rmr1 knockdowns help mitigate this type of general repeat-induced silencing, then transgenesis methods and insert complexity may be inconsequential. Molecularly-vetted lines will be advanced to specific transgene silencing tests as described in the following section and will be crossed to a B73 T Pl' line [a T6-9 (043-1) interchange with the Pl1-Rh allele of Pl' state −1.5cM from the breakpoint [11] introgressed (A) to −94% B73] to test effects on maintaining Pl' paramutant states. We fully expect that any functional KD lines will phenocopy the existing twirl mutations with this assay. Using the same B73 T Pl' line as recurrent female, 2 functional Rmr1 RNAi transgene inserts will be backcrossed for subsequent deposit to the Maize Genetics Cooperation Stock Center (Urbana, Ill.). As the Hill line is a B73 5 A188 hybrid, introgression to >90% B73 will be swift. The T Pl' interchange may prove useful for specific line developments by other researchers [11] but can just as easily be purged.

Test Effects of Rmr1 RNAi on a Silenced pWRWR Transgene Array

Prior results indicate that the rmr1-1 mutation mitigates transgene silencing both somatically [43] and sometimes meiotically (FIG. 17). As such, we expect that production of dsRNA specific to Rmr1 will similarly lead to the reactivation of the silenced pWRWR transgene array [67]. Although the test is genetically simple, both Rmr1 RNAi and pWRWR transgene loci are linked to a glufosinate-resistance marker. Fortunately, we have introgressed the silenced pWRWR transgene into a 4Co63 T Pl' line (null for pericarp color1 function) so that a dark anther phenotype is a proxy for Rmr1 knockdown (FIG. 18) and pericarp coloring of any kind reflects pWRWR transgene expression (FIG. 17). With these visual features, we can evaluate large numbers of individuals with each transgene combination to determine whether or not the RNAi constructs are effective at releasing silencing of the pWRWR repeated array. A molecularly vetted Rmr1 KD plant will be crossed with a plant hemizygous for the silenced pWRWR insert and −300 progeny grown to maturity. Individuals will be visually scored for anther phenotypes and each plant will be pollinated with the 4Co63 T Pl' line so that follow-up evaluations of meiotically-heritable reactivations can be documented in the next generation. Hand-harvested ears will be tagged and visually inspected for pericarp color. For those ears showing evidence of pWRWR reactivation, progeny sets will be grown out and similarly assayed. Additional backcrosses can be used to follow the stability of reactivated states for several more generations.

Test Effects of rmr1 RNAi on de novo Transgene Silencing

While Rmr1 KD lines promise to be extremely useful for controlling transgene function within the broader research community, the largest economic potential would appear to reside in mitigating de novo transgene silencing during the transgenesis procedure itself. Commercial lines are now so far removed from the academic inbreds used by most maize geneticists that an introgression-based plant improvement strategy is unattractive. Using Hill as a representative, we will compare PTF-generated transgenesis events with cell autonomous GFP/GUS-reporter constructs in the presence or absence of dsRmr1-generating constructs using biolistic co-bombardments of embryogenic callus and subsequent plant regeneration. We will evaluate locus and copy numbers using Southern blot analyses and measure relative reporter GUS expression levels in TI plants and reevaluate these features following outcrossing to our B73 T Pl' stock. We expect, as before, that any functional Rmr1 KD transgenes will result in visual reactivation of Pl' states (darkly colored anthers). Analysis of the outcross progeny will be important to verify locus numbers, transgene linkages, and to assess both the genetic and epigenetic stability of the reporter gene arrays.

The Rmr1 dsRNA construct has been described in above. The reporter constructs will be derivatives of the pKGWFS7 binary vector [68] in which a recombinase mediated insertion of promoter sequences (Gateway technology; [69]) drives the expression of an endoplasmic-retained GFP-GUS fusion protein. To leverage existing resources and provide reagents for future studies, we will make separate constructs using the double CaMV35S promoter, −2.5 kb of pl1-B73 [70], and as much unique 5' sequences we can obtain from rmr1-B73. Based on unpublished sequence comparisons (S. Gross and J. Hollick), the immediate −2.5 kb region of pl1-B73 is unique from the nearly 8 kb of 5' sequences we have of pl1-Rhoades, so do those sequences confer the same tissue-specific patterns of pl1-B73 expression as displayed by pigment patterns, or are some of the sequences shared with pl1-Rhoades important to tissue-specific regulation? The rmr1-B73 reporter fusion will help us understand Rmr1 gene control and will complement subsequent proteomic studies by highlighting tissues of potentially high protein expression and of functionally important significance. More details regarding the Rmr1-B735' sequences can be found in Example 8. All promoter regions will be PCR-amplified, introduced into a Gateway topoisomerase-based cloning vector [71], sequenced, and shuttled into pKGWFS7 for biolistic transformation. Reporter constructs will be co-bombarded with either the Rmr1 RNAi construct or empty pMGC161 vector. We will request TI seeds from 6 events from each biolistic combination for a total of 36 lines.

Example 10

Identify RMR1 Molecular Partners Using Affinity Purification, Mass Spectrometry, and cDNA Sequencing Macromolecular complexes-affinity purified from transgenic plant expressing functional TAP-tagged RMR proteins—will be fractionated and analyzed using mass spectrometry and cDNA sequencing. While our forward genetic screens have been successful at identifying molecular components required to maintain Pl' states, there are undoubtedly other components that can only be identified using biochemical or proteomic approaches. One of the major advantages of studying the mechanics of gene silencing in a physically large organism like maize is the abundant availability of defined tissues for use in biochemical purifications. In theory, one could identify RMR1 interacting proteins using a yeast 2-hybrid (Y2H) assay with a maize cDNA library. To our knowledge, there is currently no cDNA library available in which an Rmr1 sequence has been identified. Further, the biological relevance of interactions detected in the Y2H are often unknown, or questionable when compared to affinity purification of in vivo complexes followed by proteomic analysis [72]. The Y2H assay thus appears better suited to verification studies than as a primary screening method. There is no simple approach; therefore one should maximize the likelihood that any detected interactions are biologically relevant. Tandem-Affinity Purification followed by Mass Spectrometry (TAP-MS) has recently emerged as a powerful methodology for identifying protein-protein interactions in monocots [73]. By complementing a rmr1-3/rmr1-3 defect with a TAP-tagged RMR1 protein expressed from the Rmr1-B73 promoter, we will purify functionally relevant macromolecular complexes for RNA and proteomic analysis. With this approach we will discover novel components of the maize gene silencing machinery and, in turn, provide new reagents, targets, and models for future studies.

Create Monocot Expression Constructs for RMR1-TAP Fusion Molecules

Since expression from a constitutive promoter like ubiquitin might lead to non-biologically relevant protein associations in cell or tissue types in which Rmr1 is not typically expressed, we would like to have the native promoter drive a RMR1-TAP fusion protein. We will therefore modify a pCAMBIA1300-based Gateway vector [74] to have a 5' portion of the Rmr1-B73 sequence replace the resident ubiquitin promoter. This sub aim requires some additional vetting of the Rmr1-B73 gene structure to identify the transcription start site and non-repetitive 5' putative promoter sequences. We will also need to generate a near full length Rmr1 cDNA to create the in-frame translational fusions with the TAP tag. We will begin with a N-terminal TAP addition (NTAP) and will modify the construct as needed to create a CTAP version.

According to a multiple species alignment, of almost exclusively bioinformatics-based annotations, the RMR1 protein should begin at the presumed translational start site (FIG. 19). We are currently using 5' rapid amplification of cDNA ends (5' RACE) to identify whether any additional protein coding sequence is present in Rmr1 mRNAs. We will also use a combination of primer extension and RNase protection assays to verify and assign the transcription start site. We will subclone and sequence 5' flanking sequence from the in-house B73 BAC and use BLAST to survey up to ~4 kb of 5' sequence for transposons and gene fragments that might help delimit intergenic regulatory sequences. We will use restriction-enzyme based strategies to swap the ubiquitin promoter in the binary vector with as large a piece of the Rmr1-B735' sequence as possible. Based on the 5' RACE results, we will design appropriate primer sets to amplify the protein-coding portion of a RT-derived cDNA molecule and introduce these amplicons into Gateway topoisomerase-based cloning vectors [71]. These clones will be sequenced and shuttled into our pCAMBIA1300-Rmr1 promoter derivatives for subsequent *A. tumefaciens* mediated maize transformation.

RMR1-TAP Functional Complementation

To maximize the likelihood that an affinity purification strategy will identify functionally relevant RMR1 protein partners, it is preferred that the tagged RMR1 protein is functional and not in competition with native RMR1 protein. Therefore, we will test transgenic complementation of the rmr1-3 putative null mutation using the C and N-terminal tagged constructs (described in the section above). Transgenic plants exhibiting rmr1-3 complementation will be used for tandem affinity purification of RMR1-TAP complexes (see section below). With APHIS permits, *A. tumefaciens* strain EHA10-transformed with the binary vectors detailed in SA2a—will be forwarded to PTF, and we will request seeds from 10 independent transformation events for each construct. Rapidly dividing tissues of glufosinate-resistant Ti plants will be assayed by western blots for expression of the proteinA component of the TAP tag, and positive plants will be crossed by our B73 homozygous T Pl'rmr1-3 line. Glufosinate-resistant, protein A-positive progeny will be crossed by a B73 T Pl'rmr1-31T Pl'Rmr1-B73 heterozygote to ensure that all progeny receive a pl1-Rhoades allele of P1' state. If the RMR1-TAP constructs genetically complement the rmr1-3 defect, then glufosinate-resistant plants with fully fertile pollen (T/7) and a rmr1-3/rmr1-3 SNP-genotype should have a distincT Pl' anther phenotype (FIG. 18). These same genotypes will have Pl-like anthers if there is non-complementation. If the large (181 aa) N- or C-terminal TAP addition does not allow proper folding or protein function, this strategy may not work. Even so, we expect these lines will be useful for assessing intracellular localizations via TAP-based immunocytochemistry.

Identify RNA and Protein Partners Using Tap-Based Purification, Biochemical Fractionation, Nucleic Acid Sequencing, Mass Spectrometry and Proteomics Guided by the expression profiles revealed by the promoter-reporter constructs (described in Example 7), or indicated by proteinA-based western blotting, TAP-based purifications [73], total protein quantifications, and SDS-PAGE will be used to assess purification, yields, and numbers of complex members. We will perform the same purification steps on untransformed plants as a purification-specificity control. Based on these estimates, we can appropriately scale subsequent production purifications. We do not expect plant material to be limiting for these purifications. Depending on the number of complex members, we will repeat purifications and provide desalted trypsinized 500 ng of protein for nanoscale reverse-phase (RP) HPLC (1-10 proteins), or 100 μg for ion exchange and RP HPLC (>10 proteins), separations followed by electrospray ionization with tandem MS/MS detection. The Cancer Research Laboratory at the University of California at Berkeley will provide both the mass spectrometry and Seaquest-based protein identification on a recharge basis. The facility runs a Thermo Finnigan LCQ Decca XP Plus ion trap mass spectrometer with a NanoLC/ESI ion source for identification of peptides in complex mixtures. Data analysis will be performed by an IBM 16 node computational cluster.

Given DRD1 may interface directly with siRNAs or indirectly via complex association with AGO4 [28], it would not be unexpected to find RMR1 complexed with small RNA molecules [75]. If small RNAs co-purify with TAP-tagged RMR1, we will fractionate these on polyacryamide gels, excise and prepare for amplification and small-scale sequencing. Should there be significant RNA sequence heterogeneity within these samples, we will perform deep sequencing of these RNA populations using 454 or Solexa platforms.

Example 11

Measure Trait Variances Associated with RMR1 Function in Heterotic Crosses

Near-isogenic inbred lines will be tested for heritable effects of RMR1 function on traits of commercial importance. While well documented that rmr1 mutations lead to heritable changes of Pl1-Rhoades function and hence pigment traits [10], effects on alleles affecting other traits remains speculative. Given preliminary data showing inbred genomes conditioned in the absence of RMR1 function increase progeny dry ear weights nearly 10% in crosses to the B73 inbred (Table 5), a more rigorous test of the epigenetic complementation concept will be conducted. As an overview of the proposed experimental design, relative grain yield, days-to-flowering, and plant height will be compared among progeny of A619 5 A632 and B73 5 Mol7 reciprocal crosses in which one or both parents is deficient for RMR1 function. Both rmr1-1 and rmr1-3 alleles, introgressed (A) to ~97% into the above-mentioned inbred lines, will be tested initially.

Germplasm Development

The A619, A632, B73, and Mol7 elite inbred lines were originally obtained directly from the North Central Plant Introduction Station (Ames, Iowa). Prior to molecular identification, rmr1 mutant alleles had been committed to an inbred backcross program requiring concomitant introgression of a reporter Pl1-Rhoades allele linked to the T6-9 (043-1) breakpoint. Molecular SNP-based genotyping will rapidly advance these introgressions in the absence of the translocation chromosome so that the A619/A632 materials can be combined. A comparison of the helicase-domain (rmrl-1), and predicted null (rmrl-3) mutations will be important to assess possible loss-of-function strategies for commercial application. These efforts will provide highly introgressed rmr1 mutant lines that will be deposited to the Maize Genetics Cooperative Stock Center for curation and dissemination to the broader research community.

Heterotic Crosses

Respective combinations of inbred lines B73 or A632 (representative of Reid Yellow Dent) and Mol7 or A619 (representative of Lancaster Sure Crop) represent one of the most highly utilized heterotic patterns in the commercial hybrid industry. As Pl' reversion tests suggest a parent of origin effect [10], it is desirable to sample rmr1-conditioned genomes through both pistil and pollen transmission. For each BC4F2 progeny, plants homozygous for either inbred Rmr1 or rmr1 mutant alleles will be identified by SNP-typing and reciprocally crossed with plants from the inbred heterotic parent (i.e. rmr1-1 A619 5 A632; A632 5 rmr1-1 ^ A619; A619 5 rmr1-1 ^ A632; rmr1-1 ^ A632 5 A619).

Sampling and Measurement

Five ear-to-row plots will be evaluated from each heterotic cross for days-to-flowering, plant height at anthesis, and dry kernel weights. For each plot, three 20-kernel rows will be planted side by side and, in an attempt to simulate large field conditions, only plants of the interior rows will be sampled. Each of the 5 genotypic complements (complete set of crossing combinations) of test plots will be assigned field placements in a randomized design to effectively neutralize environmental variations and will all be planted on the same day. Plots will be open pollinated and individual ears will be hand-harvested, dried in a 100° F. room briefly to minimize kernel damage and shelled for weight measurements. Kernels will be further dried to 12-15% moisture content and the kernels per plant will be directly weighed on a Federal Grain Inspection Service-approved balance. Test weights (lbs/bushel) per plot will be approximated using a hand-held balance. Grain yield estimates of Mg per hectare will be calculated per plot and per genotype. Mean values+/−s.e.m. for each set of 5 test plots will be compared using a two-tailed z-test. Since it is quite likely that not all sampled plots will contain 20 plants, an appropriate scaling factor will be applied to obtain mean yield estimates.

Should these initial studies with A619 and A632 reveal biomass and/or grain yield increases, this experimental design will be repeated with rmr1 mutations introgressed to ~99%, and we will forge collaborations for field-based yield trials. If no differences are indicated, we will still replicate the experimental design with B73 and Mol7 combinations. As it is possible that epigenome conditioning is progressive and cumulative, the experimental design will be repeated using appropriate BC4F2S3 A619 and A632 lines. Given the pedigree of these materials, it is expected that provenance tests, measurements of these or additional traits, and statistical treatments can be used to make estimates of epigenetic variation contributions to broad-sense heritability. Recombinant inbred lines will also be derived from these materials to measure the effects of RMR1 defects on inbreeding depression in future projects.

Example 12

Monitor In Vivo RMR1-Based Silencing Behaviors

A RMR1 RNAi-based knock-down construct will be evaluated for mitigation of transgene silencing and the cell autonomy and resilencing properties of RMR1 action will be measured at the boundaries of irradiation-induced segmental monoploid sectors. Given that the rmr1-1 mutation is able to release repression of silenced 35S-B1 [43], pWRWR, and 35S-H2B-YFP transgene arrays, it is quite likely that RNAi-based knockdown (KD) lines of Rmr1 RNA could be broadly employed to mitigate, or control, transgene silencing for commercial application. The fact that RMR1 defects themselves appear not to affect plant development [10] suggests that such KD strategies can complement existing breeding programs without compromising yields. The experiments will generate data regarding efficacy, cell autonomy, and kinetics of RMR action on transgene silencing. These efforts will generate materials immediately translatable to crop improvement efforts.

Create and Validate Rmr1 Knockdown Lines

The pMGC161 vector and cloning technology developed in the NSF-sponsored maize chromatin consortium ([43]; NSF DBI-0421679; www.chromdb.org) will be used to create a dsRNA expression construct specific for Rmr1 (double CaMV35S promoter driving an inverted repeat of ~1 kb of Rmr1 exon2 separated by a *O. sativa* waxy1 intron stuffer). Recombinant DNA manipulations will be carried out in *E. coli* and the sequence-validated construct will be electroporated into *A. tumefacians* strain EHA101. With appropriate APHIS permit, the transformed strain will be shipped to the Iowa State Plant Transformation Facility (PTF) for maize (HiII line) transgenesis. We will request PTF provide seeds from 10 separate glufosinate-resistant transformation events. Transgene-based effects on endogenous Rmr1 RNA levels will be assayed using RT-PCR and Southern blotting will be employed to characterize insert structures for those plants demonstrating a molecular KD phenotype. Agro-mediated transformation is chosen to establish these lines as there is a greater chance for single inserts of low transgene complexity that, in general, tend to escape gene silencing. If Rmr1 knock-downs help mitigate this type of general repeat-induced silencing, then transgenesis methods and insert complexity may be inconsequential. Molecularly-vetted lines will be advanced to specific transgene silencing tests (see Example 7) and will be crossed to a B73 T Pl line [a T6-9 (043-1) interchange with the Pl1-Rh allele of Pl state ~1.5cM from the breakpoint [11] introgressed (^) to ~97% B73] to test effects on maintaining Pl paramutant states. We fully expect that any functional KD lines will phenocopy the existing rmr1 mutations with this assay. Using the same B73 T Pl line as recurrent female, 2 functional Rmr1 RNAi transgene inserts will be backcrossed for subsequent deposit to the Maize Genetics Cooperation Stock Center (Urbana, Ill.).

Test Effects of Rmr1 RNAi on Silenced Transgene Arrays

Although rmr and mop mutations alone can suffice to mitigate transgene silencing (U.S. Pat. No. 7,264,970), commercial lines are now so far removed from academic inbreds used by most maize geneticists that an introgression-based plant improvement strategy is unattractive. Data regarding de novo mitigation of transgene silencing with RMR1 RNAi KD technology is expected to motivate this approach for agronomic applications. Based on preexisting mutant analyses we expect that production of dsRNA specific to Rmr1 will similarly lead to the reactivation of both silenced pWRWR and 35S-H2B-GFP arrays. The partially silenced 35S-H2B-GFP line has been made available from our collaborator for these studies. Although the tests are genetically simple, both Rmr1 RNAi and silenced transgene loci are linked to a glufosinate-resistance marker. Fortunately, we have introgressed the silenced pWRWR transgene into a 4Co63 T Pl line (null for pericarp color1 function) so that a dark anther phenotype is a proxy for Rmr1 knockdown and pericarp coloring of any kind reflects pWRWR transgene expression. Marker-assisted selection will be used to synthesize 35S-H2B-GFP/RMR1 RNAi KD lines. With the visual phenotypes afforded by the various transgenes, we can evaluate large numbers of individuals with each transgene combination to determine whether or not the RNAi constructs are effective at releasing silencing of the repeated arrays. A molecularly vetted Rmr1 KD plant will be crossed with plants hemizygous for the silenced pWRWR or 35S-H2B-GFP inserts and ~300 progeny of each will grown to maturity. For the pWRWR lines, progeny individuals will be visually scored for anther phenotypes and each plant will be pollinated with the 4Co63 T Pl line so that follow-up evaluations of meiotically-heritable reactivations can be documented in the next generation. Hand-harvested ears will be tagged and visually inspected for pericarp color. For ears showing pWRWR reactivation, progeny sets will be grown out and similarly assayed. For the 35S-H2B-GFP lines, progeny will be PCR-genotyped and then tissues of selected individuals will be evaluated by epi-fluorescence microscopy using standard dissecting scope equipment available in the Hollick/Amacher lab. Follow up trans-generational studies will be used to measure transmission properties of these reactivated transgenes.

Use Mosaic Analysis to Test Cell Autonomy and Kinetics of Rmr1 Function

Given the structural and molecular genetic similarities of RMR1 to CLSY1, it is possible that some RMR1-mediated silencing may be non-cell autonomous. This possibility can be addressed using genetic mosaics. We have used mosaic analyses to show that Pl changes to a Pl state progressively in Pl/Pl heterozygotes. From these sector boundaries, visual inspection of anthocyanin pigment levels indicate that paramutagenic action is cell autonomous. Similar boundary analyses are proposed to test the cell autonomy, silencing, and reactivation properties of RMR1 on the partially silenced 35S-H2B-YFP transgene array (FIG. 20). The following cross will be used to create progeny genotypes that will be subjected to mosaic analysis; 1) 35S-H2B-YFP; Rmr1/Rmr1 w15 rmr1-1/+rmr1-1. This progeny can be generated immediately using the partially silenced 35S-H2B-YFP line and a w15 Pl rmr1-1/+Pl Rmr1 line we have already synthesized. Using the same irradiation protocol as detailed in Hake and Sinha (1994) and as used previously, in situ YFP-fluorescence will be documented at boundaries marked by segmental monoploid albino tissue (35S-H2B-YFP; w15 rmr1-1/ - - - ). Evaluating reactivated YFP fluorescence coincidence with sector boundaries will indicate whether or not the silencing function of RMR1 is cell autonomous. As dry seed-induced sectors occur during a developmental window, there will be an opportunity to observe these clonal reactivation events in a broad range of sector sizes and developmental timings. In addition to testing the CLSY1-like properties of facilitating intercellular silencing, we expect these studies will provide basic information needed to evaluate future transgenic approaches in which RMR1 functions are manipulated for tissue-specific control of silencing.

Example 13

Characterize RMR1 Biochemical Functions

To functionally classify the type of biochemistry carried out by this novel Snf2 protein, recombinant RMR1 will be characterized with in vitro assays of ATPase, nucleic acid translocation, and nucleosome sliding activities. It is unknown how RMR1 affects the stability of pl1 RNA and small RNA abundance, two phenotypes not observed in any biochemically characterized Snf2 protein. Although RMR1 contains structural motifs for ATP binding and hydrolysis, it is also unknown if RMR1, or related proteins CLSY1 and DRD1, is a functional ATPase. We will purify recombinant RMR1 and derivatives from a heterologous protein expression system and assay these for characteristic Snf2 protein functions: nucleic acid-stimulated ATPase activity, ATP-dependent dsDNA translocation, and nucleosome sliding. These kinetic measurements of RMR1 action are essential to understanding the molecular role of RMR1 in co-transcriptional repression, small RNA biogenesis, and RdDM. These efforts will provide recombinant RMR1 proteins with which to develop additional immunoreagents, protein interaction assays, and crystals for future studies.

Prepare Recombinant Proteins

DNA clones containing SsoRAD54 and the E563Q mutant [22] will be obtained and used to construct controls in all assays. We will express and test both full-length protein (RMR1fl; 161 kDa) and a truncated form (RMR1cd; ~70 kDa) containing the most highly conserved Snf2 region. Full length and truncated Snf2 proteins have been successfully expressed and purified from both prokaryotic and baculovirus systems [*E. coli:* 76, 22, 77; baculovirus: 39, Gaillard et al.

2003, 78], and truncated proteins containing only the conserved domains exhibit full function in vitro assays [76,22]. These assays will also be used to characterize the biochemical defects of RMR1-1, RMR1-2, and RMR1-4 derivatives that contain amino acid substitutions predicted to disrupt nucleic acid binding and ATP hydrolysis. Coding sequence for RMR1fl and RMR1cd will be amplified (using maize flcDNA) and ligated into pET302 and pET303 vectors (Invitrogen) containing a T7lac promoter and either N or C-terminal hexahistidine (His) tags respectively. Recombinant expression vectors will be transformed into BL21-CodonPlus RIL competent cells (Stratagene) that contain extra copies of *E. coli* argU, ileY, and leuW tRNA genes to reduce the negative effects of codon bias on heterologous protein expression. His-tagged proteins will be purified on Ni-resin columns under native conditions and prepared for individual assays.

Perform Biochemical Assays

ATPase Assays:

ATPase assays measuring radioisotope release from $-^{32}$P ATP will be performed with double and single stranded DNA substrates [22,79]. Given the role RMR1 plays in RdDM, it will be important to measure dsRNA, ssRNA and RNA:DNA duplex stimulation. Tests of the RMR1 mutants are expected to verify predicted effects of the mutations on ATP hydrolysis and they will serve as a negative control to show specificity of the assay for RMR1. The controls used in this assay either have dsDNA dependent ATPase activity (SsoRAD54cd) or are inactive (DExx box disrupting E563Q; 22). Titrating reaction component concentrations (such as ATP, protein, and nucleic acids) will allow detailed measurement of wild type and mutant RMR1 kinetics to compare with those measured for SsoRAD54cd and other Snf2 proteins representing the major functional classifications [80, 81, 77, 22, 76, 79].

Translocation:

Snf2 proteins are predicted to use ATP hydrolysis to translocate along dsDNA, and this translocation activity is routinely assayed by efficient removal of triplex forming oligonucleotides (TFO). TFOs tightly bind the major groove of DNA double helices to promote alterations in gene expression [82]. TFO removal assays will be performed as described [22,83] using triplex DNA formed by binding of a $^{32}$P-labeled TFO to the corresponding binding site on duplex DNA [83]. Free TFO is detected by gel separation and quantified by phosphorimage capture and image processing.

Nucleosome sliding: In vitro mobilization of mononucleosomes is thought to reflect a chromatin remodeling function in vivo [84]. This assay is preferred over nuclease sensitivity assays because it produces cleaner results by using small, well-defined chromatin templates. Radiolabeled mononucleosomes are generated by serial dilution transfer from chicken oligonucleosomes onto $^{32}$P body-labeled DNA templates and verified by native PAGE [85]. Purified mononucleosomes will be incubated with RMR1, and at specific time points (1-60 min), aliquots are removed and the reaction quenched. Nucleosome boundaries are then assayed by ExoIII mapping. Nucleosome mobility is determined by the presence of a ladder of partially degraded DNA products [39,86]. SsoRad54cd will be included as a positive control, and the RMR1 mutants will also be assayed for nucleosome mobilization ability.

Example 14

Define RMR1 Subcellular Localizations and Epistatic Relationships

To define both the intracellular and epistatic positions of RMR1 within the nucleus and RdDM/CTGS pathway, materials will be synthesized for immunofluorescence detection of functional RMR1 in normal and rmr/mop mutant backgrounds. These materials will also be important for basic RMR1 protein characterizations and for future biochemical purifications and interaction studies of RMR1 protein partners. Aside from our initial characterizations [65], nuclear actions of the plant-specific RMR1 subfamily remain unknown. Reagents and materials will be synthesized for immunofluorescence detection of functional RMR1 in normal and rmr/mop mutant backgrounds to define both the intracellular and epistatic positions of RMR1 within the nucleus and RdDM/CTGS pathway. These reagents and materials will also be important for basic RMR1 protein characterizations and provide a platform for future biochemical purifications and interaction studies of RMR1 protein partners.

Generate RMR1 Custom Peptide Antibodies

With assistance of peptide chemists at New England Peptides (Gardner, Mass.), four 10-15 amino acid peptides have been identified to optimize high antigenicity, low cross reactivity, and functional relevance. Two peptides flank the conserved C terminal region, and two others flank the RMR1-3 truncation placement in the N-terminal region. We have detected rmr1 mRNA by RT PCR in rmr1-3 homozygotes suggesting that the premature rmr1-3 nonsense codon does not flag the RNA for nonsense-mediated decay. Peptide synthesis, conjugation to keyhole limpet heamocyanin and antisera production will be outsourced to Covance Research Products (AALAC accredited, OLAW #A3850-01, USDA #23-R-0007). Rabbits will be prescreened for general cross reactivity to maize proteins by ELISA, and each conjugated peptide will be injected into two rabbits with low background. Serum will be analyzed by western blot for RMR1 specificity, and antibodies will be purified by either IgG or peptide affinity columns as necessary to reduce non-specific background. Protein extracts from rmr1-3 homozygotes will aid our evaluation and enhancement of RMR1 specificity. These reagents will be useful for both western blot analyses and tissue based in situ hybridizations in addition to their intended use in immunolocalization studies. Similar peptide-based antiseras have been successfully used by Pontes et al. (2006) in these types of studies for PolIVa, PolIVb, DCL3, RDR2, and DRD1.

Generate Functional FLAG-Tagged RMR1 Transgenic Maize

Stable lines expressing a functional 6×FLAG-tagged version of RMR1 will be generated as a backup strategy for immunolocalization studies and to provide an experimental platform for future studies related to RMR1 biochemistry and nuclear actions. Since expression from a constitutive promoter like ubiquitin might lead to non-biologically relevant artifacts in cell or tissue types in which Rmr1 is not typically expressed, we will have the native promoter drive a RMR1-FLAG fusion protein. We will therefore modify a pCAMBIA1300-based Gateway vector [74] to have a 5' portion of the Rmr1-B73 sequence replace the resident ubiquitin promoter. Non-repetitive 5' putative promoter sequences will be identified from the recently sequenced BAC CH201-7N19 (AC212361) that we have shown contains the rmr1 locus [65]. We will use PCR and restriction-enzyme based strategies to swap the ubiquitin promoter with as much unique Rmr1-B73 5 sequence as possible. We will design appropriate oligonucleotide primer sets to amplify the protein-coding portion of an rmr1 flcDNA molecule (also see Example 8), introduce these amplicons into a Gateway topoisomerase-based cloning vector [71], and derive both N- and C-terminal FLAG versions with additional modification. These clones will be sequenced and shuttled into our pCAMBIA1300-Rmr1 promoter derivatives for subsequent *A. tumefaciens*-mediated maize transformation as detailed above in SA1. We will evaluate these 10 lines by genetic segregation tests (locus copy number) and both southern (locus arrangements) and northern (RNA expression) blot hybridizations. To ensure that immunolocalizations represent biologically relevant action, it is essential that the epitope-tagged RMR1 protein is functional. Rapidly dividing tissues of glufosinate-resistant Ti plants will be assayed by western blots for expression of FLAG-RMR1 and positive plants will be crossed by our B73 homozygous T Pl rmr1-1 line. Glufosinate-resistant, FLAG-positive progeny will be crossed by a B73 T Pl rmr1-1/+Pl Rmr1-B73 heterozygote to ensure that all progeny receive a Pl1-Rhoades allele of Pl state. If the RMR1-FLAG constructs genetically complement the rmr1-1 defect, then glufosinate-resistant plants with fully fertile pollen (T/T) and a rmr1-1/rmr1-1 SNP-genotype should have a distinct Pl anther phenotype (FIG. 18). Lines derived from transgenic plants showing rmr1-1 complementation will be used for immunolocalization and epistasis analysis.

Perform Immunolocalization and Epistasis Analyses

Peptide antibodies and/or anti-FLAG antibodies against epitope-tagged RMR1 will be used for in situ detection in maize root-tip cells using epi-fluorescence microscopy. We will also track RMR1 cellular localizations in different mutant backgrounds. For example, RMR1 and MOP1 (Zm-RDR2) are both required for the accumulation of siRNAs and likely function together in the RdDM pathway [65]. If RMR1 is mislocalized in mop1 mutants it would suggest that mop1 is epistatic to RMR1. As additional rmr mutants or maize mutants in the RdDM pathway are identified, they will be submitted to similar analyses. This approach, which was successfully employed in *Arabidopsis* to characterize the RdDM pathway [28], promises to define similar relationships for a novel Snf2 component as well as provide a robust cytological platform for understanding the nuclear dynamics mediating small RNA metabolism and allelic interactions in large grain cereals.

Example 15

Evaluate Effects of RMR1 on Epigenomic Conditioning and Heterosis

To profile the genome-wide effects of RMR1 action and heterosis on small RNA biogenesis, small RNA libraries from inbred rmr1 mutants, wildtype, and $F_1$ progeny will be characterized using Solexa-based sequencing. Near-isogenic inbred lines will also be tested for heterotic effects of RMR1 function on traits of commercial importance. Based on 1) published data regarding RMR1 effects on Pl1-Rh, 2) the loss of ~70% of ~24 nt small RNAs in rmr1 mutants, and 3) our observations related to the breeding behaviors of rmr1 mutants, we hypothesize that different constellations of genomic heterochromatin are conditioned by the presence or absence of RMR function. This differential conditioning of the genome should be reflected in unique small RNA sequence profiles. Given that preconditioning the genome (+/−RMR1 action) appears to give rise to differential developmental responses upon outcrossing (Table 5), unique small RNA sequence profiles are also expected in $F_1$ epihybrids. To evaluate the dynamics of the RMR1-modulated epigenome, we will compare Solexa-based deep sequencing profiles of small RNAs from rmr1-1/rmr1-1 inbreds (B73), rmr1-1/Rmr1-B73 from marker assisted introgression into B73, and reciprocal rmr1-1/Rmr-B73 and Rmr1-B73/rmr1-1 $F_1$s. Given preliminary data showing inbred genomes conditioned in the absence of RMR1 function increase progeny dry ear weights nearly 10% in crosses to the B73 inbred (Table 5), a more rigorous test of the epigenetic complementation concept is also highly motivated. These experiments will address a hypothesis regarding the role of epigenetic complementation in heterosis and provide defining information regarding RMR1 action in the maize genome.

Develop Germplasm Resources

The A619, A632, B73, and Mo17 inbred lines were obtained directly from the North Central Plant Introduction Station (Ames, Iowa). Prior to molecular identification, rmr1 mutant alleles had been committed to backcross programs requiring concomitant introgression of a reporter Pl1-Rhoades allele linked to the T6-9 (043-1) breakpoint. Molecular SNP-based genotyping will rapidly advance these introgressions in the absence of the translocation chromosome so that the A619/A632 materials can be combined. Regardless of the experimental outcomes, these efforts will provide introgressed rmr1 mutant lines that will be deposited to the Maize Genetics Cooperative Stock Center for curation and public dissemination.

Perform Epihybrid Crosses and Prepare Small RNA Libraries

Using B73 as recurrent pistillate parent, rmr1-1 has been introgressed and subsequently recovered in homozygous condition. The rmr1-1 ^ B73 line (~97% B73) will be advanced to the S2 generation prior to analysis. As Pl reversion tests in rmr1 mutants suggest a parent of origin effect [10], it is desirable to sample $rmr1^-$ conditioned genomes through both pistil and pollen transmission. Reciprocal crosses will be made between rmr1-1/rmr1-1 and Rmr1-B73/rmr1-1 parents. Next, congenic parents will be grown alongside reciprocal $F_1$ epihybrids and developing ears (5 cm) will be collected for RNA isolations. The >50 g of enriched small RNA we routinely isolate from individual ears will provide more than enough material to assemble independent small RNA libraries. We will use the reagent package from illumina to clone libraries for Solexa sequencing using fractionated and PAGE purified small RNAs according to Illumina protocols. We will make 8 individual libraries (2 biological replicates) for a single Solexa flow-cell sequencing run.

Conduct Small RNA Profiling and Downstream Bioinformatics

The University of California at Berkeley operates a Functional Genomics Laboratory (FGL) for full support of Solexa sequencing projects. We will provide FGL with the prepared libraries, a 1 Tb data storage device and the most up-to-date B73 maize genome sequence to obtain alignment data for export and evaluation. Downstream analysis of the reads and alignments will be guided by prior 454 sequencing analyses carried out on rdr2 mutants [87,60] It is expected that, as was seen in the rdr2 analyses, there will be clear trends in the quantity and types of RMR1-dependent RNA sequences in addition to the identification of all the maize microRNAs and trans-acting siRNAs. Although full analytical power of these profiles awaits the final maize genome assembly we will use sliding-window alignment profiles [60] in available assemblies of high confidence to evaluate position-dependent representations. Thus both in the short and long-term, this data set promises to highlight specific dynamic changes to the maize epigenome represented by RMR1-dependent conditioning.

Evaluate Heterotic Traits in Conditioned Epigenotypes

Respective combinations of inbred lines B73 or A632 (Reid Yellow Dent) and Mo17 or A619 (Lancaster Sure Crop) represent one of the most highly utilized heterotic patterns in the commercial hybrid industry. For each BC4F2 progeny, plants homozygous for either inbred Rmr1 or rmr1 mutant alleles will be identified by SNP-typing and reciprocally crossed with plants from the inbred heterotic parent (i.e. rmr1-1 ^ A619 A632; A632 rmr1-1 ^ A619; A619 rmr1-1 ^ A632; rmr1-1 ^ A632 A619). Five plots will be evaluated from each heterotic cross for days-to-flowering, plant height at anthesis, and dry kernel weights. For each plot, three 20-kernel rows will be planted side by side and only plants of the interior rows will be sampled. Each of the test plots will be assigned randomized field placements to effectively neutralize environmental variations and will all be planted on the same day. Plants will be open pollinated and individual ears will be hand-harvested, dried in a 100 F room briefly to minimize kernel damage and shelled for weight measurements. Kernels will be further dried to 12-15% moisture content and the kernels per plant will be directly weighed. Test weights (lbs/bushel) per plot will be approximated using a hand-held balance. Grain yield estimates of Mg per hectare will be calculated per plot and per genotype. Mean values+/− s.e.m. for each set of 5 test plots will be compared using a two-tailed z-test. Should these initial studies with A619 and A632 reveal biomass and/or grain yield increases, this experimental design will be repeated with rmr1 mutations introgressed to ~99%, and we will forge collaborations for field-based yield trials. If no differences are indicated, we will still replicate the experimental design with B73 and Mol7 combinations. As it is possible that epigenome conditioning is progressive and cumulative, the experimental design will be repeated using appropriate BC4F2S3 A619 and A632 lines. Given the pedigree of these materials, it is expected that provenance tests, measurements of these or additional traits, and statistical treatments can be used to make estimates of epigenetic variation contributions to broad-sense heritability.

TABLE 1

Testcross results measuring establishment of Pl' in T Pl-Rh rmr1-2/+ Pl' rmr1-1 plants

| Parental cross | Pl-Rh tester | Progeny structural genotype | No. of individual progeny with specific anther color scores 1 | 2 | 3 | 4 | 5 | 6 | 7 |
|---|---|---|---|---|---|---|---|---|---|
| 05-542-6 5 05-103-1 | A632 | +/+ | 0 | 3 | 0 | 0 | 0 | 0 | 0 |
| 05-103-1 5 05-542-6 | A632 | +/+ | 1 | 6 | 0 | 2 | 0 | 0 | 0 |
| 06-530 X 06-316-10 | A632 | +/+ | 0 | 2 | 3 | 0 | 0 | 0 | 0 |

TABLE 1-continued

Testcross results measuring establishment of Pl' in T Pl-Rh rmr1-2/+ Pl' rmr1-1 plants

| Parental cross | Pl-Rh tester | Progeny structural genotype | No. of individual progeny with specific anther color scores 1 | 2 | 3 | 4 | 5 | 6 | 7 |
|---|---|---|---|---|---|---|---|---|---|
| 05-539-1 5 05-542-6 | A619 | +/+ | 1 | 2 | 0 | 1 | 0 | 0 | 5 |
| 05-539-2 5 05-541-6 | A619 | +/+ | 0 | 0 | 1 | 0 | 1 | 3 | 8 |
| 05-541-6 5 05-539-2 | A619 | +/+ | 0 | 3 | 2 | 4 | 1 | 1 | 0 |
| 06-528 X 06-316-12 | A619 | +/+ | 0 | 0 | 0 | 3 | 2 | 5 | 4 |
| 05-528 X 06-316-10 | A619 | +/+ | 0 | 0 | 0 | 0 | 0 | 0 | 11 |
| 05-528 X 06-316-10 | A619 | +/+ | 0 | 0 | 0 | 0 | 0 | 1 | 7 |
| 05-542-6 5 05-103-1 | A632 | T/+ | 0 | 4 | 5 | 3 | 0 | 0 | 0 |
| 05-103-1 5 05-542-6 | A632 | +/T | 0 | 5 | 0 | 2 | 0 | 0 | 1 |
| 06-530 X 06-316-10 | A632 | +/T | 1 | 11 | 1 | 0 | 0 | 0 | 0 |
| 05-539-1 5 05-542-6 | A619 | +/T | 0 | 0 | 1 | 0 | 1 | 0 | 5 |
| 05-539-2 5 05-541-6 | A619 | +/T | 0 | 0 | 0 | 1 | 0 | 0 | 2 |
| 05-541-6 5 05-539-2 | A619 | T/+ | 0 | 1 | 2 | 1 | 2 | 0 | 0 |
| 06-528 X 06-316-12 | A619 | +/T | 0 | 4 | 2 | 1 | 0 | 0 | 0 |
| 05-528 X 06-316-10 | A619 | +/T | 0 | 0 | 0 | 0 | 0 | 0 | 4 |
| 05-528 X 06-316-10 | A619 | +/T | 0 | 0 | 0 | 0 | 0 | 0 | 5 |
| Totals: | | +/+ | 2 | 16 | 6 | 10 | 4 | 10 | 35 |
| | | T/+ | 0 | 5 | 7 | 4 | 2 | 0 | 0 |
| | | +/T | 1 | 20 | 4 | 4 | 1 | 0 | 17 |

TABLE 2

Evaluation of b1 paramutation in rmr1/rmr1; B-I/B' plants through crosses to Rmr1 b1 testers

| Staminate parent | Parental plant phenotype | Allele tested | No. of progeny with specific plant phenotypes B-I | B' |
|---|---|---|---|---|
| 02-508-22 | Dark B-I | rmr1-1 | 0 | 60 |
| 02-508-60 | B-I | rmr1-1 | 4 | 30 |
| 02-514-8 | Dark B' | rmr1-3 | 0 | 53 |
| 02-514-73 | B-I | rmr1-3 | 0 | 59 |
| Totals | | | 4 | 202 |

TABLE 3

Complementation tests

| Parents Pistillate | Staminate | Progeny No. of ears | No. of individuals with specific anther color scores 1 | 2 | 3 | 4 | 5 | 6 | 7 |
|---|---|---|---|---|---|---|---|---|---|
| mop1-3 (ems98262) | | | | | | | | | |
| +/mop1-1 | ems98262/ems98262 | 1 | 2 | 8 | 2 | 0 | 0 | 0 | 3 |
| ems98262/ems98262 | +/mop1-1 | 1 | 6 | 0 | 3 | 0 | 0 | 0 | 5 |
| +/ems98262 | rmr1-1/rmr1-1 | 2 | 4 | 19 | 17 | 0 | 0 | 0 | 0 |
| +/ems98262 | rmr2-1/rmr2-1 | 1 | 2 | 14 | 10 | 0 | 0 | 0 | 0 |
| +/ems98262 | rmr6-1/rmr6-1 | 1 | 0 | 6 | 17 | 2 | 0 | 0 | 0 |
| +/rmr6-1 | ems98262/ems98262 | 1 | 6 | 10 | 7 | 1 | 0 | 0 | 0 |

TABLE 3-continued

| Complementation tests | | | | | | | | | |
|---|---|---|---|---|---|---|---|---|---|
| Parents | | Progeny No. of | No. of individuals with specific anther color scores | | | | | | |
| Pistillate | Staminate | ears | 1 | 2 | 3 | 4 | 5 | 6 | 7 |
| mop1-4 (ems98941) | | | | | | | | | |
| +/mop1-1 | ems98941/ems98941 | 2 | 5 | 1 | 1 | 0 | 0 | 0 | 12 |
| +/mop1-3 | ems98941/ems98941 | 2 | 1 | 14 | 1 | 2 | 0 | 0 | 8 |
| rmr1-1/rmr1-1 | ems98941/ems98941 | 2 | 1 | 12 | 1 | 1 | 0 | 0 | 0 |
| rmr2-1/rmr2-1 | ems98941/ems98941 | 2 | 10 | 11 | 2 | 4 | 0 | 0 | 0 |
| +/rmr6-1 | ems98941/ems98941 | 2 | 7 | 15 | 2 | 1 | 0 | 0 | 0 |
| rmr1-3 (ems98287) | | | | | | | | | |
| +/mop1-3 | ems98287/ems98287 | 1 | 10 | 7 | 4 | 0 | 0 | 0 | 0 |
| ems98287/ems98287 | +/rmr1-1 | 2 | 11 | 16 | 2 | 0 | 0 | 0 | 20 |
| +/ems98287 | rmr2-1/rmr2-1 | 1 | 13 | 13 | 0 | 0 | 0 | 0 | 0 |
| ems98287/ems98287 | rmr6-1/rmr6-1 | 1 | 18 | 3 | 0 | 0 | 0 | 0 | 0 |
| rmr1-4 (ems051069) | | | | | | | | | |
| +/mop1-4 | ems051069/ems051069 | 1 | 7 | 13 | 2 | 3 | 0 | 0 | 0 |
| +/rmr1-1 | ems051069/ems051069 | 1 | 0 | 7 | 6 | 1 | 0 | 0 | 13 |
| +/rmr1-3 | ems051069/ems051069 | 1 | 3 | 6 | 2 | 0 | 0 | 0 | 15 |
| +/rmr2-1 | ems051069/ems051069 | 1 | 8 | 17 | 4 | 0 | 0 | 0 | 0 |
| +/rmr6-1 | ems051069/ems051069 | 1 | 2 | 13 | 12 | 0 | 0 | 0 | 0 |

TABLE 4

| PCR oligonucleotide primers used | | |
|---|---|---|
| Primer Name | Sequence (5' -> 3') | SEQ ID NO |
| Os10F | GAA GAG TTG GGT GTG GGA AA | 30 |
| Os10R | AAC ATC TTG CTC TGG CCT GT | 31 |
| ExonF | GTG TCA GTG TTT GCC GAG AA | 32 |
| ExonR | CTA TAG TTA CAA TCA AAT TGC TAC TGA G | 33 |
| mid5'F | GTT GCA GCA ACA GAA TCT AGC | 34 |
| Os11F | AAG CAT ACA TCG CCC AAA TC | 35 |
| Os15R | CAC GCT GAT GCT CAT ACA TA | 36 |
| Os12F | CCC AAT CAT GCA ACT CCT CT | 37 |
| Os13Rb | CCA TAA CTT ATT CCA AGA ATA CC | 38 |
| IntronF | GTC GTT TCC CAG AAT AGA GTA ACT TTG | 39 |
| IntronR | GAT ATG CAG AAT ACT ACA TAT GTT TGA G | 40 |
| CAPS6F | GCA TCT TCG CAA GTT CTT CA | 41 |
| CAPS6R | TCG TGG GAA GTC ATC TCC TC | 42 |
| CAPS10F | ATG AGT AGT GCC CCA TCC AG | 43 |
| CAPS10R | TCA GCC TCT TCT TCC TCT TCC | 44 |
| Intron0 F2 | GAT GAC GCT TCT CAT GAC G | 45 |
| Intron0 R2 | ATC ATC GTA GTC ATC TTC AAA GG | 46 |

TABLE 5

Trait analysis of progeny derived from single pollen sources of different rmri genotypes

| Pistillate inbred | Trait[a] | Staminate inbred genotype[b] Rmr1-A632/Rmr1-A632 | rmr1-1/rmr1-1 | Statistical significance[c] z | P |
|---|---|---|---|---|---|
| A632 | ACS | 1.7 ± 0.1 (14) | 5.2 ± 0.4 (20) | 8.8 | <<0.01 |
| | Height | 223.2 ± 1.2 (14) | 221.1 ± 1.2 (20) | 1.2 | n.s. |
| | DTF | 59.4 ± 0.3 (14) | 57.1 ± 0.1 (20) | 6.3 | <<0.01 |
| | Ear weight | 87.9 ± 3.6 (8) | 85.2 ± 1.6 (13) | 0.7 | n.s. |
| Mo17 | ACS | 1.8 ± 0.3 (19) | 4.9 ± 0.2 (16) | 8.5 | <<0.01 |
| | Height | 246.2 ± 0.8 (19) | 238.8 ± 2.2 (16) | 0.4 | <0.01 |
| | DTF | 57.6 ± 0.2 (19) | 57.2 ± 0.3 (16) | 1.1 | n.s. |
| | Ear weight | 122.2 ± 3.4 (12) | 123.8 ± 3.6 (8) | 0.3 | n.s. |
| B73 | ACS | 1.9 ± 0.1 (18) | 4.8 ± 0.3 (16) | 9.1 | <<0.01 |
| | Height | 239.1 ± 1.9 (18) | 213.4 ± 9.6 (19) | 5.4 | <<0.01 |
| | DTF | 59.8 ± 0.2 (18) | 58.4 ± 0.3 (17) | 3.8 | <<0.01 |
| | Ear weight | 91.8 ± 3.0 (12) | 101.3 ± 1.8 (11) | 2.6 | <0.01 |

$F_2S_1$ plants homozygous for either Rmr1-A632/Rmr1-A632 or rmr1-1/rmr1-1 were identified and used to generate lines through single seed descent.

[a]Anther Color Scores, (ACS; [7]), plant height in cm at anthesis (height), days to flowering or first pollen shed (DTF), and dry ear weight in grams from open pollinations were measured on individual progeny.

[b]Means ± s.e.m. with number of individual progeny measured in parentheses.

[c]A two-sample z-test was applied to the null hypothesis that the difference in mean values between the two progeny sets is due to random chance. n.s. indicates a non-significant P value of >0.05.

1. Brink R A (1958) Paramutation at the R locus in maize. Cold Spring Harb Symp Quant Biol 23: 379-391.
2. Hollick J B, Dorweiler J E, Chandler V L (1997) Paramutation and related allelic interactions. Trends Genet 13: 302-308.
3. Brink R A (1973) Paramutation. Annu Rev Genet 7: 129-152.
4. Chandler V L, Stam M (2004) Chromatin conversations: Mechanisms and implications of paramutation. Nat Rev Genet 5: 532-544.
5. Rassoulzadegan M, Grandjean V, Gounon P, Vincent S, Gillot I, et al. (2006) RNA-mediated non-mendelian inheritance of an epigenetic change in the mouse. Nature 441: 469-474.
6. Cone K C, Cocciolone S M, Burr F A, Burr B (1993) Maize anthocyanin regulatory gene pl is a duplicate of c1 that functions in the plant. Plant Cell 5: 1795-1805.
7. Hollick J B, Patterson G I, Coe E H Jr, Cone K C, Chandler V L (1995) Allelic interactions heritably alter the activity of a metastable maize pl allele. Genetics 141: 709-719.
8. Hollick J B, Patterson G I, Asmundsson I M, Chandler V L (2000) Paramutation alters regulatory control of the maize pl locus. Genetics 154: 1827-1838.
9. Hollick J B, Chandler V L (1998) Epigenetic allelic states of a maize transcriptional regulatory locus exhibit overdominant gene action. Genetics 150: 891-897.
10. Hollick J B, Chandler V L (2001) Genetic factors required to maintain repression of a paramutagenic maize pl1 allele. Genetics 157: 369-378.
11. Hollick J B, Kermicle J L, Parkinson S E (2005) Rmr6 maintains meiotic inheritance of paramutant states in *Zea mays*. Genetics 171: 725-740.
12. Gross S M, Hollick J B (2007) Multiple trans-sensing interactions affect meiotically heritable epigenetic states at the maize pl1 locus. Genetics 176: 829-839.
13. Dorweiler J E, Carey C C, Kubo K M, Hollick J B, Kermicle J L, et al. (2000) Mediator of paramutation1 is required for establishment and maintenance of paramutation at multiple maize loci. Plant Cell 12: 2101-2118.
14. Alleman M, Sidorenko L, McGinnis K, Seshadri V, Dorweiler J E, et al. (2006) An RNA-dependent RNA polymerase is required for paramutation in maize. Nature 442: 295-298.
15. Woodhouse M R, Freeling M, Lisch D (2006) Initiation, establishment, and maintenance of heritable MuDR transposon silencing in maize are mediated by distinct factors. PLoS Biol 4: e339.
16. Chan S W, Zilberman D, Xie Z, Johansen L K, Carrington J C, et al. (2004) RNA silencing genes control de novo DNA methylation. Science 303: 1336.
17. Buhler M, Verdel A, Moazed D (2006) Tethering RITS to a nascent transcript initiates RNAi- and heterochromatin-dependent gene silencing. Cell 125: 873-886.
18. Buhler M, Haas W, Gygi S P, Moazed D (2007) RNAi-dependent and -independent RNA turnover mechanisms contribute to heterochromatic gene silencing. Cell 129: 707-721.
19. Sainz M B, Grotewold E, Chandler V L (1997) Evidence for direct activation of an anthocyanin promoter by the maize C1 protein and comparison of DNA binding by related Myb domain proteins. Plant Cell 9: 611-625.
20. Lawrence C J, Schaeffer M L, Seigfried T E, Campbell D A, Harper L C (2007) Maize GDB's new data types, resources and activities. Nucleic Acids Res 35: D895-D900.
21. Flaus A, Martin D M, Barton G J, Owen-Hughes T (2006) Identification of multiple distinct Snf2 subfamilies with conserved structural motifs. Nucleic Acids Res 34: 2887-2905.
22. Durr H, Flaus A, Owen-Hughes T, Hopfner K P (2006) Snf2 family ATPases and DExx box helicases: Differences and unifying concepts from high-resolution crystal structures. Nucleic Acids Res 34: 4160-4167.
23. Jones D T (1999) GenTHREADER: An efficient and reliable protein fold recognition method for genomic sequences. J Mol Biol 287: 797-815.
24. Kanno T, Mette M F, Kreil D P, Aufsatz W, Matzke M, et al. (2004) Involvement of putative SNF2 chromatin remodeling protein DRD1 in RNA-directed DNA methylation. Curr Biol 14: 801-805.
25. Kanno T, Aufsatz W, Jaligot E, Mette M F, Matzke M, et al. (2005) A SNF2-like protein facilitates dynamic control of DNA methylation. EMBO Rep 6: 649-655.
26. Chan S W, Henderson I R, Zhang X, Shah G, Chien J S, et al. (2006) RNAi, DRD1, and histone methylation actively target developmentally important non-CG DNA methylation in *Arabidopsis*. PLoS Genet 2: e83.

27. Mathieu O, Bender J (2004) RNA-directed DNA methylation. J Cell Sci 117: 4881-4888.
28. Pontes O, Li C F, Nunes P C, Haag J, Ream T, et al. (2006) The *Arabidopsis* chromatin-modifying nuclear siRNA pathway involves a nucleolar RNA processing center. Cell 126: 79-92.
29. Smith L M, Pontes O, Searle I, Yelina N, Yousafzai F K, et al. (2007) An SNF2 protein associated with nuclear RNA silencing and the spread of a silencing signal between cells in *Arabidopsis*. Plant Cell 19: 1507-1521.
30. Shaked H, Avivi-Ragolsky N, Levy A A (2006) Involvement of the *Arabidopsis* SWI2/SNF2 chromatin remodeling gene family in DNA damage response and recombination. Genetics 173: 985-994.
31. Huettel B, Kanno T, Daxinger L, Aufsatz W, Matzke A J, et al. (2006) Endogenous targets of RNA-directed DNA methylation and Pol IV in *Arabidopsis*. EMBO J 25: 2828-2836.
32. Cone K C, Cocciolone S M, Moehlenkamp C A, Weber T, Drummond B J, et al. (1993) Role of the regulatory gene pl in the photocontrol of maize anthocyanin pigmentation. Plant Cell 5: 1807-1816.
33. Walker E L, Robbins T P, Bureau T E, Kermicle J, Dellaporta S L (1995) Transposon-mediated chromosomal rearrangements and gene duplications in the formation of the maize R-r complex. EMBO J 14: 2350-2363.
34. Cao X, Jacobsen S E (2002) Locus-specific control of asymmetric and CpNpG methylation by the DRM and CMT3 methyltransferase genes. Proc Natl Acad Sci USA 99: 16491-16498.
35. Cao X, Jacobsen S E (2002) Role of the *Arabidopsis* DRM methyltransferases in de novo DNA methylation and gene silencing. Curr Biol 12: 1138-1144.
36. Cao X, Aufsatz W, Zilberman D, Mette M F, Huang M S, et al. (2003) Role of the DRM and CMT3 methyltransferases in RNA-directed DNA methylation. Curr Biol 13: 2212-2217.
37. Patterson G I, Thorpe C J, Chandler V L (1993) Paramutation, an allelic interaction, is associated with a stable and heritable reduction of transcription of the maize b regulatory gene. Genetics 135: 881-894.
38. Jeddeloh J A, Stokes T L, Richards E J (1999) Maintenance of genomic methylation requires a SWI2/SNF2-like protein. Nat Genet 22: 94-97.
39. Brzeski J, Jerzmanowski A (2003) Deficient in DNA methylation 1 (DDM1) defines a novel family of chromatin-remodeling factors. J Biol Chem 278: 823-828.
40. Raabe E H, Abdurrahman L, Behbehani G, Arceci R J (2001) An SNF2 factor involved in mammalian development and cellular proliferation. Dev Dyn 221: 92-105.
41. Dennis K, Fan T, Geiman T, Yan Q, Muegge K (2001) Lsh, a member of the SNF2 family, is required for genome-wide methylation. Genes Dev 15: 2940-2944.
42. Bourc'his D, Bestor T H (2002) Helicase homologues maintain cytosine methylation in plants and mammals. Bioessays 24: 297-299.
43. McGinnis K M, Springer C, Lin Y, Carey C C, Chandler V (2006) Transcriptionally silenced transgenes in maize are activated by three mutations defective in paramutation. Genetics 173: 1637-1647.
44. Lisch D, Carey C C, Dorweiler J E, Chandler V L (2002) A mutation that prevents paramutation in maize also reverses Mutator transposon methylation and silencing. Proc Natl Acad Sci USA 99: 6130-6135.
45. Xie Z, Johansen L K, Gustafson A M, Kasschau K D, Lellis A D, et al. (2004) Genetic and functional diversification of small RNA pathways in plants. PLoS Biol 2: e104.
46. Zilberman D, Cao X, Jacobsen S E (2003) ARGONAUTE4 control of locus-specific siRNA accumulation and DNA and histone methylation. Science 299: 716-719.
47. Zilberman D, Cao X, Johansen L K, Xie Z, Carrington J C, et al. (2004) Role of *Arabidopsis* ARGONAUTE4 in RNA-directed DNA methylation triggered by inverted repeats. Curr Biol 14: 1214-1220.
48. Bercury S D, Panavas T, Irenze K, Walker E L (2001) Molecular analysis of the doppia transposable element of maize. Plant Mol Biol 47: 341-351.
49. Chandler V L (2007) Paramutation: From maize to mice. Cell 128: 641-645.
50. Eissenberg J C, Shilatifard A (2006) Leaving a mark: The many footprints of the elongating RNA polymerase II. Curr Opin Genet Dev 16: 184-190.
51. Farris S D, Rubio E D, Moon J J, Gombert W M, Nelson B H, et al. (2005) Transcription-induced chromatin remodeling at the c-myc gene involves the local exchange of histone H2A.Z. J Biol Chem 280: 25298-25303.
52. Irvine D V, Zaratiegui M, Tolia N H, Goto D B, Chitwood D H, et al. (2006) Argonaute slicing is required for heterochromatic silencing and spreading. Science 313: 1134-1137.
53. McClintock B (1951) Chromosome organization and genic expression. Cold Spring Harb Symp Quant Biol 16: 13-47.
54. Martienssen R, Barkan A, Taylor W C, Freeling M (1990) Somatically heritable switches in the DNA modification of mu transposable elements monitored with a suppressible mutant in maize. Genes Dev 4: 331-343.
55. Fedoroff N V (1999) The Suppressor-mutator element and the evolutionary riddle of transposons. Genes Cells 4: 11-19.
56. Blewitt M E, Vickaryous N K, Paldi A, Koseki H, Whitelaw E (2006) Dynamic reprogramming of DNA methylation at an epigenetically sensitive allele in mice. PLoS Genet 2: e49.
57. Kermicle J L, Eggleston W B, Alleman M (1995) Organization of paramutagenicity in R-stippled maize. Genetics 141: 361-372.
58. Panavas T, Weir J, Walker E L (1999) The structure and paramutagenicity of the R-marbled haplotype of *Zea mays*. Genetics 153: 979-991.
59. Stam M, Belele C, Ramakrishna W, Dorweiler J E, Bennetzen J L, et al. (2002) The regulatory regions required for B' paramutation and expression are located far upstream of the maize b1 transcribed sequences. Genetics 162: 917-930.
60. Kasschau K D, Fahlgren N, Chapman E J, Sullivan C M, Cumbie J S, et al. (2007) Genome-wide profiling and analysis of *Arabidopsis* siRNAs. PLoS Biol 5: e57.
61. Konieczny A, Ausubel F M (1993) A procedure for mapping *Arabidopsis* mutations using co-dominant ecotype-specific PCR-based markers. Plant J 4: 403-410.
62. Edgar R C (2004) MUSCLE: Multiple sequence alignment with high accuracy and high throughput. Nucleic Acids Res 32: 1792-1797.
63. Kinoshita T, Miura A, Choi Y, Kinoshita Y, Cao X, et al. (2004) One-way control of FWA imprinting in *Arabidopsis* endosperm by DNA methylation. Science 303: 521-523.
64. Slotkin R K, Freeling M, Lisch D (2005) Heritable transposon silencing initiated by a naturally occurring transposon inverted duplication. Nat Genet 37: 641-644.

65. Hale C J, Stonaker J L, Gross S M, Hollick J B (2007) A novel Snf2 protein maintains trans-generational regulatory states established by paramutation in maize. PLoS Biol. 5(10):e275.

66. Parkinson S E, Gross S M, Hollick J B (2007) Maize sex determination and abaxial leaf fates are canalized by a factor that maintains repressed epigenetic states. Dev Biol. 308(2):462-73.

67. Cocciolone S M, Chopra S, Flint-Garcia S A, McMullen M D, Peterson T (2001) Tissue-specific patterns of a maize Myb transcription factor are epigenetically regulated. Plant J. 27(5):467-78.

68. Karimi M, Inzé D, Depicker A (2002) GATEWAY vectors for *Agrobacterium*-mediated plant transformation. Trends Plant Sci. 7(5):193-5.

69. Hartley J L, Temple G F, Brasch M A (2000) DNA cloning using in vitro site-specific recombination. Genome Res. 10(11): 1788-95.

70. Swigonova Z, Lai J, Ma J, Ramakrishna W, Llaca V, Bennetzen J L, Messing J. (2004) On the tetraploid origin of the maize genome. Comp Funct Genomics. 5(3):281-4.

71. Shuman S. (1994) Novel approach to molecular cloning and polynucleotide synthesis using vaccinia DNA topoisomerase. J Biol Chem 269(51):32678-84.

72. Shevchenko Y, Bouffard G G, Butterfield Y S, Blakesley R W, Hartley J L, Young A C, Marra M A, Jones S J, Touchman J W, Green E D (2002) Systematic sequencing of cDNA clones using the transposon Tn5. Nucleic Acids Res. 30(11):2469-77.

73. Rohila J S, Chen M, Chen S, Chen J, Cemy R, Dardick C, Canlas P, Xu X, Gribskov M, Kanrar S, Zhu J K, Ronald P, Fromm M E. (2006) Protein-protein interactions of tandem affinity purification-tagged protein kinases in rice. Plant J. 46(1):1-13.

74. Miki D, Shimamoto K. Simple RNAi vectors for stable and transient suppression of gene function in rice. Plant Cell Physiol. 45(4):490-5.

75. Girard A, Sachidanandam R, Hannon G J, Carmell M A. (2006) A germline-specific class of small RNAs binds mammalian Piwi proteins. Nature. 442(7099):199-202.

76. Bakshi R, Mehta A K, Sharma R, Maiti S, Pasha S, Brahmachari V. (2006) Characterization of a human SWI2/SNF2 like protein hINO80: demonstration of catalytic and DNA binding activity. Biochem Biophys Res Commun. 339(1):313-20.

77. Liu M, Xie Z, Price D H. A human RNA polymerase II transcription termination factor is a SWI2/SNF2 family member. J Biol Chem 273(40):25541-4.

78. Thoma N H, Czyzewski B K, Alexeev A A, Mazin A V, Kowalczykowski S C, Pavletich N P. (2005) Structure of the SWI2/SNF2 chromatin-remodeling domain of eukaryotic Rad54. Nat Struct Mol Biol. 12(4):350-6.

79. Domanskyi A, Virtanen K T, Palvimo J J, Jänne O A. (2006) Biochemical characterization of androgen receptor-interacting protein 4. Biochem J. 393(Pt 3):789-95.

80. Laurent B C, Treich I, Carlson M. (1993) The yeast SNF2/SWI2 protein has DNA-stimulated ATPase activity required for transcriptional activation. Genes Dev. 1993 April; 7(4):583-91.

81. Auble D T, Hansen K E, Mueller C G, Lane W S, Thomer J, Hahn S. (1994) Mot1, a global repressor of RNA polymerase II transcription, inhibits TBP binding to DNA by an ATP-dependent mechanism. Genes Dev. 8(16):1920-34.

82. Knauert M P, Glazer P M. (2001) Triplex forming oligonucleotides: sequence-specific tools for gene targeting. Hum Mol Genet. 10(20):2243-51.

83. Whitehouse I, Stockdale C, Flaus A, Szczelkun M D, Owen-Hughes T. (2003) Evidence for DNA translocation by the ISWI chromatin-remodeling enzyme. Mol Cell Biol. 23(6):1935-45.

84. Alexeev A, Mazin A, Kowalczykowski S C. (2003) Rad54 protein possesses chromatin-remodeling activity stimulated by the Rad51-ssDNA nucleoprotein filament. Nat Struct Biol. 10(3):182-6.

85. Owen-Hughes T, Utley R T, Steger D J, West J M, John S, Cote J, Havas K M, Workman J L. (1999) Analysis of nucleosome disruption by ATP-driven chromatin remodeling complexes. Methods Mol Biol. 119:319-31.

86. Smith C L, Peterson C L. (2005) ATP-dependent chromatin remodeling. Curr Top Dev Biol. 65:115-48.

87. Lu C, Kulkarni K, Souret F F, MuthuValliappan R, Tej S S, Poethig R S, Henderson I R, Jacobsen S E, Wang W, Green P J, Meyers B C. (2006) MicroRNAs and other small RNAs enriched in the *Arabidopsis* RNA-dependent RNA polymerase-2 mutant. Genome Res. 16(10):1276-88.

What is claimed is:

1. A method for reducing or mitigating gene silencing of a transgene, comprising:

providing a transgenic plant with a transgene; and introducing a recombinant nucleic acid to said plant, wherein said recombinant nucleic acid comprises a nucleic acid in an antisense orientation wherein the sense orientation of said nucleic acid encodes the polypeptide of SEQ ID NO: 1, wherein said antisense nucleic acid reduces expression of the encoded SEQ ID NO: 1 polypeptide, and wherein the level of expression of said transgene is increased relative to the level of expression of said transgene in a transgenic plant that does not contain said recombinant nucleic acid.

2. A method for reducing or mitigating gene silencing of a transgene, comprising:

providing a transgenic plant with a transgene; and introducing a recombinant nucleic acid to said plant, wherein said recombinant nucleic acid comprises an RNA interference (RNAi) construct comprising at least a fragment of 20 contiguous nucleotides of a nucleic acid that encodes the polypeptide of SEQ ID NO: 1, wherein said RNAi construct reduces expression of the encoded SEQ ID NO: 1 polypeptide, and wherein the level of expression of said transgene is increased relative to the level of expression of said transgene in a transgenic plant that does not contain said recombinant nucleic acid.

3. A transgenic plant comprising a recombinant nucleic acid including a nucleic acid in an antisense orientation wherein the sense orientation of said nucleic acid encodes the polypeptide of SEQ ID NO: 1, and wherein said antisense nucleic acid reduces expression of the encoded SEQ ID NO: 1 polypeptide.

4. A transgenic plant comprising a recombinant nucleic acid including an RNA interference (RNAi) construct comprising at least a fragment of 20 contiguous nucleotides of a nucleic acid that encodes the polypeptide of SEQ ID NO: 1, wherein said RNAi construct reduces expression of the encoded SEQ ID NO: 1 polypeptide.

5. Seed from the transgenic plant of claim 3, wherein the seed comprises a recombinant nucleic acid including a nucleic acid in an antisense orientation wherein the sense orientation of said nucleic acid encodes the polypeptide of SEQ ID NO: 1.

6. Seed from the transgenic plant of claim 4, wherein the seed comprises a recombinant nucleic acid including an RNAi construct comprising at least a fragment of 20 contiguous nucleotides of a nucleic acid that encodes the polypeptide of SEQ ID NO: 1.

* * * * *

SEQUENCE LISTING

```
<160> NUMBER OF SEQ ID NOS: 46

<210> SEQ ID NO 1
<211> LENGTH: 485
<212> TYPE: PRT
<213> ORGANISM: Zea mays

<400> SEQUENCE: 1

His Gln Arg Glu Ala Phe Glu Phe Met Trp Thr Asn Leu Val Gly Asp
 1               5                   10                  15

Ile Arg Leu Asp Glu Ile Lys His Gly Ala Lys Pro Asp Val Val Gly
            20                  25                  30

Gly Cys Val Ile Cys His Ala Pro Gly Thr Gly Lys Thr Arg Leu Ala
        35                  40                  45

Ile Val Phe Ile Gln Thr Tyr Met Lys Val Phe Pro Asp Cys Arg Pro
    50                  55                  60

Val Ile Ile Ala Pro Arg Gly Met Leu Phe Ala Trp Asp Glu Glu Phe
65                  70                  75                  80
```

```
Lys Lys Trp Asn Val Asp Val Pro Phe His Ile Leu Asn Thr Thr Asp
                85                  90                  95

Tyr Thr Gly Lys Glu Asp Arg Glu Ile Cys Lys Leu Ile Lys Lys Glu
            100                 105                 110

His Arg Thr Glu Lys Leu Thr Arg Leu Val Lys Leu Leu Ser Trp Asn
        115                 120                 125

Lys Gly His Gly Ile Leu Gly Ile Ser Tyr Gly Leu Tyr Thr Lys Leu
    130                 135                 140

Thr Ser Glu Lys Pro Gly Cys Thr Glu Glu Asn Lys Val Arg Ser Ile
145                 150                 155                 160

Leu Leu Asp Asn Pro Gly Leu Leu Val Leu Asp Glu Gly His Thr Pro
                165                 170                 175

Arg Asn Glu Arg Ser Val Met Trp Lys Thr Leu Gly Asn Val Lys Thr
            180                 185                 190

Glu Lys Arg Ile Ile Leu Ser Gly Thr Pro Phe Gln Asn Asn Phe Leu
        195                 200                 205

Glu Leu Tyr Asn Ile Leu Cys Leu Val Arg Pro Arg Phe Gly Glu Met
    210                 215                 220

Phe Leu Thr Lys Ser Arg Val Gly Arg Arg His Tyr Val Ser Lys Lys
225                 230                 235                 240

Gln Lys Asp Lys Phe Ser Asp Lys Tyr Glu Lys Gly Val Trp Ala Ser
                245                 250                 255

Leu Thr Ser Asn Val Thr Asp Asp Asn Ala Glu Lys Val Arg Ser Ile
            260                 265                 270

Leu Lys Pro Phe Val His Ile His Asn Gly Asn Ile Leu Arg Thr Leu
        275                 280                 285

Pro Gly Leu Arg Glu Ser Val Ile Ile Leu Lys Pro Leu Pro Leu Gln
    290                 295                 300

Lys Ser Ile Ile Lys Lys Val Glu Asn Ile Gly Ser Gly Asn Asn Phe
305                 310                 315                 320

Glu His Glu Tyr Val Ile Ser Leu Ala Ser Thr His Pro Ser Leu Val
                325                 330                 335

Thr Ala Ile Asn Met Ser Glu Glu Glu Ala Ser Leu Ile Asp Lys Pro
            340                 345                 350

Met Leu Ala Lys Val Arg Ser Asn Pro Tyr Glu Gly Val Lys Thr Arg
        355                 360                 365

Phe Val Ile Glu Val Val Arg Leu Ser Glu Ala Leu Arg Glu Lys Val
    370                 375                 380

Leu Ile Phe Ser Gln Phe Ile Gln Pro Leu Glu Leu Ile Lys Glu His
385                 390                 395                 400

Leu Arg Lys Phe Phe Lys Trp Arg Glu Gly Lys Glu Ile Leu Gln Met
                405                 410                 415

Asp Gly Lys Ile Leu Pro Arg Tyr Arg Gln Ala Ser Ile Glu Ala Phe
            420                 425                 430

Asn Asn Pro Asn Asn Asp Ser Arg Val Leu Leu Ala Ser Thr Arg Ala
        435                 440                 445

Cys Cys Glu Gly Ile Ser Leu Thr Gly Ala Ser Arg Ile Val Leu Leu
    450                 455                 460

Asp Val Val Trp Asn Pro Ala Val Gly Arg Gln Ala Ile Ser Arg Ala
465                 470                 475                 480

Phe Arg Ile Gly Gln
                485
```

<210> SEQ ID NO 2
<211> LENGTH: 494
<212> TYPE: PRT
<213> ORGANISM: Arabidopsis thaliana

<400> SEQUENCE: 2

```
His Gln Gln Glu Gly Phe Glu Phe Ile Trp Lys Asn Leu Ala Gly Thr
 1               5                  10                  15

Ile Met Leu Asn Glu Leu Lys Asp Phe Glu Asn Ser Asp Glu Thr Gly
            20                  25                  30

Gly Cys Ile Met Ser His Ala Pro Gly Thr Gly Lys Thr Arg Leu Thr
        35                  40                  45

Ile Ile Phe Leu Gln Ala Tyr Leu Gln Cys Phe Pro Asp Cys Lys Pro
    50                  55                  60

Val Ile Ile Ala Pro Ala Ser Leu Leu Leu Thr Trp Ala Glu Glu Phe
65                  70                  75                  80

Lys Lys Trp Asn Ile Ser Ile Pro Phe His Asn Leu Ser Ser Leu Asp
                85                  90                  95

Phe Thr Gly Lys Glu Asn Ser Ala Ala Leu Gly Leu Leu Met Gln Lys
            100                 105                 110

Asn Ala Thr Ala Arg Ser Asn Asn Glu Ile Arg Met Val Lys Ile Tyr
        115                 120                 125

Ser Trp Ile Lys Ser Lys Ser Ile Leu Gly Ile Ser Tyr Asn Leu Tyr
    130                 135                 140

Glu Lys Leu Ala Gly Val Lys Asp Glu Asp Lys Lys Thr Lys Met Val
145                 150                 155                 160

Arg Glu Val Lys Pro Asp Lys Glu Leu Asp Asp Ile Arg Glu Ile Leu
                165                 170                 175

Met Gly Arg Pro Gly Leu Leu Val Leu Asp Glu Ala His Thr Pro Arg
            180                 185                 190

Asn Gln Arg Ser Cys Ile Trp Lys Thr Leu Ser Lys Val Glu Thr Gln
        195                 200                 205

Lys Arg Ile Leu Leu Ser Gly Thr Pro Phe Gln Asn Asn Phe Leu Glu
    210                 215                 220

Leu Cys Asn Val Leu Gly Leu Ala Arg Pro Lys Tyr Leu Glu Arg Leu
225                 230                 235                 240

Thr Ser Thr Leu Lys Lys Ser Gly Met Thr Val Thr Lys Arg Gly Lys
                245                 250                 255

Lys Asn Leu Gly Asn Glu Ile Asn Asn Arg Gly Ile Glu Glu Leu Lys
            260                 265                 270

Ala Val Met Leu Pro Phe Val His Val His Lys Gly Ser Ile Leu Gln
        275                 280                 285

Ser Ser Leu Pro Gly Leu Arg Glu Cys Val Val Val Leu Asn Pro Pro
    290                 295                 300

Glu Leu Gln Arg Arg Val Leu Glu Ser Ile Glu Val Thr His Asn Arg
305                 310                 315                 320

Lys Thr Lys Asn Val Phe Glu Thr Glu His Lys Leu Ser Leu Val Ser
                325                 330                 335

Val His Pro Ser Leu Val Ser Arg Cys Lys Ile Ser Glu Lys Glu Arg
            340                 345                 350

Leu Ser Ile Asp Glu Ala Leu Leu Ala Gln Leu Lys Lys Val Arg Leu
        355                 360                 365

Asp Pro Asn Gln Ser Val Lys Thr Arg Phe Leu Met Glu Phe Val Glu
    370                 375                 380

Leu Cys Glu Val Ile Lys Glu Lys Val Leu Val Phe Ser Gln Tyr Ile
```

```
385                 390                 395                 400

Asp Pro Leu Lys Leu Ile Met Lys His Leu Val Ser Arg Phe Lys Trp
                405                 410                 415

Asn Pro Gly Glu Glu Val Leu Tyr Met His Gly Lys Leu Glu Gln Lys
            420                 425                 430

Gln Arg Gln Thr Leu Ile Asn Glu Phe Asn Asp Pro Lys Ser Lys Ala
        435                 440                 445

Lys Val Phe Leu Ala Ser Thr Lys Ala Cys Ser Glu Gly Ile Ser Leu
    450                 455                 460

Val Gly Ala Ser Arg Val Ile Leu Leu Asp Val Val Trp Asn Pro Ala
465                 470                 475                 480

Val Glu Arg Gln Ala Ile Ser Arg Ala Tyr Arg Ile Gly Gln
                485                 490


<210> SEQ ID NO 3
<211> LENGTH: 468
<212> TYPE: PRT
<213> ORGANISM: Arabidopsis thaliana

<400> SEQUENCE: 3

His Gln Gln Glu Gly Phe Glu Phe Ile Trp Lys Asn Leu Ala Gly Thr
 1               5                  10                  15

Thr Lys Ile Asn Glu Leu Asn Ser Val Gly Val Lys Gly Ser Gly Gly
            20                  25                  30

Cys Ile Ile Ser His Lys Ala Gly Thr Gly Lys Thr Arg Leu Thr Val
        35                  40                  45

Val Phe Leu Gln Ser Tyr Leu Lys Arg Phe Pro Asn Ser His Pro Met
    50                  55                  60

Val Ile Ala Pro Ala Thr Leu Met Arg Thr Trp Glu Asp Glu Val Arg
65                  70                  75                  80

Lys Trp Asn Val Asn Ile Pro Phe Tyr Asn Met Asn Ser Leu Gln Leu
                85                  90                  95

Ser Gly Tyr Glu Asp Ala Glu Ala Val Ser Arg Leu Glu Gly Asn Arg
            100                 105                 110

His His Asn Ser Ile Arg Met Val Lys Leu Val Ser Trp Trp Lys Gln
        115                 120                 125

Lys Ser Ile Leu Gly Ile Ser Tyr Pro Leu Tyr Glu Lys Leu Ala Ala
    130                 135                 140

Asn Lys Asn Thr Glu Gly Met Gln Val Phe Arg Arg Met Leu Val Glu
145                 150                 155                 160

Leu Pro Gly Leu Leu Val Leu Asp Glu Gly His Thr Pro Arg Asn Gln
                165                 170                 175

Ser Ser Leu Ile Trp Lys Val Leu Thr Glu Val Arg Thr Glu Lys Arg
            180                 185                 190

Ile Phe Leu Ser Gly Thr Leu Phe Gln Asn Asn Phe Lys Glu Leu Ser
        195                 200                 205

Asn Val Leu Cys Leu Ala Arg Pro Ala Asp Lys Asp Thr Ile Ser Ser
    210                 215                 220

Arg Ile His Glu Leu Ser Lys Cys Ser Gln Glu Gly Glu His Gly Arg
225                 230                 235                 240

Val Asn Glu Glu Asn Arg Ile Val Asp Leu Lys Ala Met Ile Ala His
                245                 250                 255

Phe Val His Val His Glu Gly Thr Ile Leu Gln Glu Ser Leu Pro Gly
            260                 265                 270

Leu Arg Asp Cys Val Val Val Leu Asn Pro Pro Phe Gln Gln Lys Lys
```

```
        275                 280                 285

Ile Leu Asp Arg Ile Asp Thr Ser Gln Asn Thr Phe Glu Phe Glu His
    290                 295                 300

Lys Leu Ser Ala Val Ser Val His Pro Ser Leu Tyr Leu Cys Cys Asn
305                 310                 315                 320

Pro Thr Lys Lys Glu Asp Leu Val Ile Gly Pro Ala Thr Leu Gly Thr
                325                 330                 335

Leu Lys Arg Leu Arg Leu Lys Tyr Glu Glu Gly Val Lys Thr Lys Phe
            340                 345                 350

Leu Ile Asp Phe Ile Arg Ile Ser Gly Thr Val Lys Glu Lys Val Leu
        355                 360                 365

Val Tyr Ser Gln Tyr Ile Asp Thr Leu Lys Leu Ile Met Glu Gln Leu
    370                 375                 380

Ile Ala Glu Cys Asp Trp Thr Glu Gly Glu Gln Ile Leu Leu Met His
385                 390                 395                 400

Gly Lys Val Glu Gln Arg Asp Arg Gln His Met Ile Asp Asn Phe Asn
                405                 410                 415

Lys Pro Asp Ser Gly Ser Lys Val Leu Leu Ala Ser Thr Lys Ala Cys
            420                 425                 430

Ser Glu Gly Ile Ser Leu Val Gly Ala Ser Arg Val Val Ile Leu Asp
        435                 440                 445

Val Val Trp Asn Pro Ser Val Glu Ser Gln Ala Ile Ser Arg Ala Phe
    450                 455                 460

Arg Ile Gly Gln
465


<210> SEQ ID NO 4
<211> LENGTH: 485
<212> TYPE: PRT
<213> ORGANISM: Oryza sativa

<400> SEQUENCE: 4

His Gln Arg Glu Ala Phe Glu Phe Met Trp Thr Asn Leu Val Gly Asp
 1               5                  10                  15

Ile Arg Leu Asn Glu Ile Lys His Gly Ala Lys Pro Asp Val Val Gly
            20                  25                  30

Gly Cys Val Ile Cys His Ala Pro Gly Thr Gly Lys Thr Arg Leu Ala
        35                  40                  45

Ile Val Phe Ile Gln Thr Tyr Met Lys Val Phe Pro Asp Cys Arg Pro
    50                  55                  60

Val Ile Ile Ala Pro Arg Gly Met Leu Phe Ala Trp Glu Gln Glu Phe
65                  70                  75                  80

Lys Lys Trp Asn Val Asn Val Pro Phe His Ile Met Asn Thr Thr Asp
                85                  90                  95

Tyr Ser Gly Lys Glu Asp Arg Asp Ile Cys Arg Leu Ile Lys Lys Glu
            100                 105                 110

His Arg Thr Glu Lys Leu Thr Arg Leu Val Lys Leu Phe Ser Trp Asn
        115                 120                 125

Arg Gly His Gly Val Leu Gly Ile Ser Tyr Gly Leu Tyr Met Lys Leu
    130                 135                 140

Thr Ser Glu Lys Val Gly Cys Thr Gly Glu Asn Lys Val Arg Thr Ile
145                 150                 155                 160

Leu Leu Glu Asn Pro Gly Leu Leu Val Leu Asp Glu Gly His Thr Pro
                165                 170                 175

Arg Asn Glu Arg Ser Val Ile Trp Lys Thr Leu Gly Lys Val Lys Thr
```

```
            180                 185                 190

Glu Lys Arg Ile Ile Leu Ser Gly Thr Pro Phe Gln Asn Asn Phe Leu
        195                 200                 205

Glu Leu Tyr Asn Ile Leu Cys Leu Val Arg Pro Arg Phe Gly Glu Met
    210                 215                 220

Phe Leu Thr Lys Thr Arg Val Gly Arg Arg His Cys Val Ser Lys Lys
225                 230                 235                 240

Gln Arg Asp Lys Phe Ser Asp Lys Tyr Glu Lys Gly Val Trp Ala Ser
                245                 250                 255

Leu Thr Ser Asn Val Thr Asp Asp Asn Ala Glu Lys Val Arg Ser Ile
            260                 265                 270

Leu Lys Pro Phe Val His Ile His Asn Gly Thr Ile Leu Arg Thr Leu
        275                 280                 285

Pro Gly Leu Arg Glu Cys Val Ile Val Leu Lys Pro Leu Pro Leu Gln
    290                 295                 300

Lys Ser Ile Ile Arg Lys Val Glu Asn Val Gly Ser Gly Asn Asn Phe
305                 310                 315                 320

Glu His Glu Tyr Val Ile Ser Leu Ala Ser Thr His Pro Ser Leu Val
                325                 330                 335

Asn Ala Ile Asn Met Thr Glu Glu Glu Ala Ser Leu Ile Asp Lys Pro
            340                 345                 350

Met Leu Glu Arg Leu Arg Ser Asn Pro Tyr Glu Gly Val Lys Thr Arg
        355                 360                 365

Phe Val Met Glu Val Val Arg Leu Cys Glu Ala Leu Lys Glu Lys Val
    370                 375                 380

Leu Ile Phe Ser Gln Phe Ile Gln Pro Leu Glu Leu Ile Lys Glu His
385                 390                 395                 400

Leu Arg Lys Ile Phe Lys Trp Arg Glu Gly Lys Glu Ile Leu Gln Met
                405                 410                 415

Asp Gly Lys Ile Leu Pro Arg Tyr Arg Gln Asn Ser Ile Glu Val Phe
            420                 425                 430

Asn Asn Pro Asp Ser Asp Ala Arg Val Leu Leu Ala Ser Thr Arg Ala
        435                 440                 445

Cys Cys Glu Gly Ile Ser Leu Thr Gly Ala Ser Arg Val Val Leu Leu
    450                 455                 460

Asp Val Val Trp Asn Pro Ala Val Gly Arg Gln Ala Ile Ser Arg Ala
465                 470                 475                 480

Phe Arg Ile Gly Gln
                485


<210> SEQ ID NO 5
<211> LENGTH: 500
<212> TYPE: PRT
<213> ORGANISM: Arabidopsis thaliana

<400> SEQUENCE: 5

His Gln Lys Lys Ala Phe Glu Phe Leu Trp Lys Asn Leu Ala Gly Ser
 1               5                  10                  15

Val Val Pro Ala Met Met Asp Pro Ser Ser Asp Lys Ile Gly Gly Cys
            20                  25                  30

Val Val Ser His Thr Pro Gly Ala Gly Lys Thr Phe Leu Ile Ile Ala
        35                  40                  45

Phe Leu Ala Ser Tyr Leu Lys Ile Phe Pro Gly Lys Arg Pro Leu Val
    50                  55                  60

Leu Ala Pro Lys Thr Thr Leu Tyr Thr Trp Tyr Lys Glu Phe Ile Lys
```

```
65                  70                  75                  80

Trp Glu Ile Pro Val Pro Val His Leu Leu His Gly Arg Arg Thr Tyr
                85                  90                  95

Cys Met Ser Lys Glu Lys Thr Ile Gln Phe Glu Gly Ile Pro Lys Pro
            100                 105                 110

Ser Gln Asp Val Met His Val Leu Asp Cys Leu Asp Lys Ile Gln Lys
        115                 120                 125

Trp His Ala Gln Pro Ser Val Leu Val Met Gly Tyr Thr Ser Phe Leu
    130                 135                 140

Thr Leu Met Arg Glu Asp Ser Lys Phe Ala His Arg Lys Tyr Met Ala
145                 150                 155                 160

Lys Val Leu Arg Glu Ser Pro Gly Leu Leu Val Leu Asp Glu Gly His
                165                 170                 175

Asn Pro Arg Ser Thr Lys Ser Arg Leu Arg Lys Ala Leu Met Lys Val
            180                 185                 190

Asp Thr Asp Leu Arg Ile Leu Leu Ser Gly Thr Leu Phe Gln Asn Asn
        195                 200                 205

Phe Cys Glu Tyr Phe Asn Thr Leu Cys Leu Ala Arg Pro Lys Phe Val
    210                 215                 220

His Glu Val Leu Val Glu Leu Asp Lys Lys Phe Gln Thr Asn Gln Ala
225                 230                 235                 240

Glu Gln Lys Ala Pro His Leu Leu Glu Asn Arg Ala Arg Lys Phe Phe
                245                 250                 255

Leu Asp Ile Ile Ala Lys Lys Ile Asp Thr Lys Val Gly Asp Glu Arg
            260                 265                 270

Leu Gln Gly Leu Asn Met Leu Arg Asn Met Thr Ser Gly Phe Ile Asp
        275                 280                 285

Asn Tyr Glu Gly Ser Gly Ser Gly Ser Gly Asp Val Leu Pro Gly Leu
    290                 295                 300

Gln Ile Tyr Thr Leu Leu Met Asn Ser Thr Asp Val Gln His Lys Ser
305                 310                 315                 320

Leu Thr Lys Leu Gln Asn Ile Met Ser Thr Tyr His Gly Tyr Pro Leu
                325                 330                 335

Glu Leu Glu Leu Leu Ile Thr Leu Ala Ala Ile His Pro Trp Leu Val
            340                 345                 350

Lys Thr Thr Thr Cys Cys Ala Lys Phe Phe Asn Pro Gln Glu Leu Leu
        355                 360                 365

Glu Ile Glu Lys Leu Lys His Asp Ala Lys Lys Gly Ser Lys Val Met
    370                 375                 380

Phe Val Leu Asn Leu Val Phe Arg Val Val Lys Arg Glu Lys Ile Leu
385                 390                 395                 400

Ile Phe Cys His Asn Ile Ala Pro Ile Arg Leu Phe Leu Glu Leu Phe
                405                 410                 415

Glu Asn Val Phe Arg Trp Lys Arg Gly Arg Glu Leu Leu Thr Leu Thr
            420                 425                 430

Gly Asp Leu Glu Leu Phe Glu Arg Gly Arg Val Ile Asp Lys Phe Glu
        435                 440                 445

Glu Pro Gly Gly Gln Ser Arg Val Leu Leu Ala Ser Ile Thr Ala Cys
    450                 455                 460

Ala Glu Gly Ile Ser Leu Thr Ala Ala Ser Arg Val Ile Met Leu Asp
465                 470                 475                 480

Ser Glu Trp Asn Pro Ser Lys Thr Lys Gln Ala Ile Ala Arg Ala Phe
                485                 490                 495
```

```
Arg Pro Gly Gln
            500


<210> SEQ ID NO 6
<211> LENGTH: 501
<212> TYPE: PRT
<213> ORGANISM: Arabidopsis thaliana

<400> SEQUENCE: 6

His Gln Arg Arg Ala Phe Glu Phe Leu Trp Arg Asn Val Ala Gly Ser
 1               5                  10                  15

Val Glu Pro Ser Leu Met Asp Pro Thr Ser Gly Asn Ile Gly Gly Cys
            20                  25                  30

Val Ile Ser His Ser Pro Gly Ala Gly Lys Thr Phe Leu Ile Ile Ala
        35                  40                  45

Phe Leu Thr Ser Tyr Leu Lys Leu Phe Pro Gly Lys Arg Pro Leu Val
    50                  55                  60

Leu Ala Pro Lys Thr Thr Leu Tyr Thr Trp Tyr Lys Glu Phe Ile Lys
65                  70                  75                  80

Trp Glu Ile Pro Val Pro Val His Leu Ile His Gly Arg Arg Thr Tyr
                85                  90                  95

Cys Thr Phe Lys Gln Asn Lys Thr Val Gln Phe Asn Gly Val Pro Lys
            100                 105                 110

Pro Ser Arg Asp Val Met His Val Leu Asp Cys Leu Glu Lys Ile Gln
        115                 120                 125

Lys Trp His Ala His Pro Ser Val Leu Val Met Gly Tyr Thr Ser Phe
    130                 135                 140

Thr Thr Leu Met Arg Glu Asp Ser Lys Phe Ala His Arg Lys Tyr Met
145                 150                 155                 160

Ala Lys Val Leu Arg Glu Ser Pro Gly Leu Leu Val Leu Asp Glu Gly
                165                 170                 175

His Asn Pro Arg Ser Thr Lys Ser Arg Leu Arg Lys Ala Leu Met Lys
            180                 185                 190

Val Gly Thr Asp Leu Arg Ile Leu Leu Ser Gly Thr Leu Phe Gln Asn
        195                 200                 205

Asn Phe Cys Glu Tyr Phe Asn Thr Leu Cys Leu Ala Arg Pro Lys Phe
    210                 215                 220

Ile His Glu Val Leu Met Glu Leu Asp Gln Lys Phe Lys Thr Asn His
225                 230                 235                 240

Gly Val Asn Lys Ala Pro His Leu Leu Glu Asn Arg Ala Arg Lys Leu
                245                 250                 255

Phe Leu Asp Ile Ile Ala Lys Lys Ile Asp Ala Ser Val Gly Asp Glu
            260                 265                 270

Arg Leu Gln Gly Leu Asn Met Leu Lys Asn Met Thr Asn Gly Phe Ile
        275                 280                 285

Asp Asn Tyr Glu Gly Ser Gly Ser Gly Ser Gly Asp Ala Leu Pro Gly
    290                 295                 300

Leu Gln Ile Tyr Thr Leu Val Met Asn Ser Thr Asp Ile Gln His Lys
305                 310                 315                 320

Ile Leu Thr Lys Leu Gln Asp Val Ile Lys Thr Tyr Phe Gly Tyr Pro
                325                 330                 335

Leu Glu Val Glu Leu Gln Ile Thr Leu Ala Ala Ile His Pro Trp Leu
            340                 345                 350

Val Thr Ser Ser Asn Cys Cys Thr Lys Phe Phe Asn Pro Gln Glu Leu
        355                 360                 365
```

```
Ser Glu Ile Gly Lys Leu Lys His Asp Ala Lys Lys Gly Ser Lys Val
    370                 375                 380

Met Phe Val Leu Asn Leu Ile Phe Arg Val Val Lys Arg Glu Lys Ile
385                 390                 395                 400

Leu Ile Phe Cys His Asn Ile Ala Pro Ile Arg Met Phe Thr Glu Leu
                405                 410                 415

Phe Glu Asn Ile Phe Arg Trp Gln Arg Gly Arg Glu Ile Leu Thr Leu
            420                 425                 430

Thr Gly Asp Leu Glu Leu Phe Glu Arg Gly Arg Val Ile Asp Lys Phe
        435                 440                 445

Glu Glu Pro Gly Asn Pro Ser Arg Val Leu Leu Ala Ser Ile Thr Ala
    450                 455                 460

Cys Ala Glu Gly Ile Ser Leu Thr Ala Ala Ser Arg Val Ile Met Leu
465                 470                 475                 480

Asp Ser Glu Trp Asn Pro Ser Lys Thr Lys Gln Ala Ile Ala Arg Ala
                485                 490                 495

Phe Arg Pro Gly Gln
            500


<210> SEQ ID NO 7
<211> LENGTH: 505
<212> TYPE: PRT
<213> ORGANISM: Oryza sativa

<400> SEQUENCE: 7

His Gln Arg Lys Ala Leu Asp Phe Leu Trp Lys Asn Leu Ala Gly Ser
 1               5                  10                  15

Ile Gln Val Glu Gly Met Asp Asn Ser Asn Val Ser Thr Gly Gly Cys
            20                  25                  30

Val Ile Ala His Thr Pro Gly Ser Gly Lys Thr Leu Leu Leu Ile Ser
        35                  40                  45

Phe Leu Val Ser Tyr Met Lys Ala His Pro Arg Ser Arg Pro Leu Val
    50                  55                  60

Leu Thr Pro Lys Ala Ala Ile His Thr Trp Lys Arg Glu Phe Glu Lys
65                  70                  75                  80

Trp Gly Ile Ser Leu Pro Leu His Val Phe His His Ala Asn Arg Ser
                85                  90                  95

Gly Lys Pro Leu Gly Ala Met Asp Ser Lys Leu Arg Ser Leu Leu Asn
            100                 105                 110

Asn Phe His Arg Pro Thr Trp Thr Asn Met Arg Leu Met Asp Ser Leu
        115                 120                 125

Asp Lys Leu Phe Lys Trp His Ala His Pro Ser Val Leu Leu Met Thr
    130                 135                 140

Tyr Ser Ser Phe Leu Gly Met Thr Lys Gln Asp Ser Lys Val Arg Asn
145                 150                 155                 160

Arg Tyr Arg Glu Phe Ile Ala Glu Val Leu Met Asn Asn Pro Gly Leu
                165                 170                 175

Leu Ile Leu Asp Glu Gly His Asn Pro Arg Ser Asn Lys Ser Lys Leu
            180                 185                 190

Arg Lys Leu Leu Met Lys Val Lys Thr Glu Phe Arg Ile Leu Leu Ser
        195                 200                 205

Gly Thr Ala Phe Gln Asn Asn Phe Glu Glu Tyr Phe Asn Thr Leu Cys
    210                 215                 220

Leu Ala Arg Pro Arg Phe Ile Gly Asp Ile Met Ser Glu Leu Val Pro
225                 230                 235                 240
```

```
Glu Arg Lys Arg Glu Thr Val Gly Arg Arg Ala Lys His Gln Glu Ala
                245                 250                 255

Val Ala Arg Arg Ala Phe Val Glu Lys Val Gly Gln Lys Ile Glu Ser
            260                 265                 270

Asp Asn Lys His Ile Arg Ser Asp Gly Ile Ser Leu Leu Asn Lys Leu
        275                 280                 285

Thr Arg Gly Phe Ile Asp Ser Phe Glu Gly Ala Lys Leu Ile Asn Leu
    290                 295                 300

Pro Gly Ile His Val Tyr Thr Val Phe Met Lys Pro Thr Asp Ile Gln
305                 310                 315                 320

Glu Glu Met Leu Ala Lys Val Thr Met Pro Lys Leu Gly Ser Ser Arg
                325                 330                 335

Phe Pro Leu Glu Val Glu Leu Leu Ile Thr Ile Gly Ser Ile His Pro
            340                 345                 350

Trp Leu Ile Lys Thr Thr Lys Ala Val Ser Thr Phe Phe Ser Pro Ala
        355                 360                 365

Glu Val Lys Lys Val Glu Arg Tyr Lys Arg Asp Phe Ala Ala Gly Cys
    370                 375                 380

Lys Ala Lys Phe Val Ile Asp Leu Leu His Lys Ser Ser Phe Arg Gly
385                 390                 395                 400

Glu Arg Val Leu Ile Phe Cys His Asn Val Ser Pro Ile Thr Phe Leu
                405                 410                 415

Val Lys Leu Ile Glu Met Val Phe Gly Trp Arg Leu Gly Glu Glu Val
            420                 425                 430

Leu Val Leu Gln Gly Asp Gln Glu Leu Pro Val Arg Ser Asp Val Met
        435                 440                 445

Asp Lys Phe Asn Gly Asp Ser Ala Gly Lys Arg Lys Val Leu Ile Ala
    450                 455                 460

Ser Thr Thr Ala Cys Ala Glu Gly Ile Ser Leu Thr Gly Ala Ser Arg
465                 470                 475                 480

Leu Val Met Leu Asp Ser Glu Trp Asn His Ser Lys Thr Arg Gln Ala
                485                 490                 495

Ile Ala Arg Ala Phe Arg Arg Gly Gln
            500                 505


<210> SEQ ID NO 8
<211> LENGTH: 464
<212> TYPE: PRT
<213> ORGANISM: Oryza sativa

<400> SEQUENCE: 8

His Gln Leu Glu Gly Phe Ser Phe Leu Val Lys Asn Leu Val Gly Asp
 1               5                  10                  15

Lys Pro Gly Gly Cys Ile Leu Ala His Ala Pro Gly Ser Gly Lys Thr
            20                  25                  30

Phe Met Leu Ile Ser Phe Ile Gln Ser Phe Leu Ala Lys Tyr Pro Ser
        35                  40                  45

Ala Arg Pro Leu Val Val Leu Pro Lys Gly Ile Leu Gly Thr Trp Lys
    50                  55                  60

Arg Glu Phe Gln Arg Trp Gln Val Glu Asp Ile Pro Leu Tyr Asp Phe
65                  70                  75                  80

Tyr Ser Val Lys Ala Asp Lys Arg Thr Glu Gln Leu Glu Val Leu Lys
                85                  90                  95

Ser Trp Glu Ala Arg Met Ser Ile Leu Phe Leu Gly Tyr Lys Gln Phe
            100                 105                 110
```

```
Ser Arg Ile Ile Cys Gly Asp Gly Asp Gly Asn Ile Ala Ala Ala Cys
        115                 120                 125

Arg Asp Arg Leu Leu Met Val Pro Asn Leu Leu Ile Leu Asp Glu Gly
    130                 135                 140

His Thr Pro Arg Asn Arg Glu Thr Asp Val Leu Ala Ser Leu Lys Arg
145                 150                 155                 160

Val Gln Thr Pro Arg Lys Val Val Leu Ser Gly Thr Leu Phe Gln Asn
                165                 170                 175

His Val Ser Glu Val Phe Asn Ile Leu Asp Leu Val Arg Pro Lys Phe
            180                 185                 190

Leu Lys Met Glu Ser Ser Arg Pro Ile Ala Arg Arg Ile Met Ser Gln
        195                 200                 205

Val Ala Ile Ser Gly Ile Arg Ser Leu Lys Gly Val His Asp Ser Ala
    210                 215                 220

Phe Thr Glu Ser Val Glu Asp Thr Leu Leu Asn Asp Asp Asn Phe Thr
225                 230                 235                 240

Arg Lys Ser His Val Ile Arg Ser Leu Arg Glu Leu Thr Lys Asp Val
                245                 250                 255

Leu His Tyr Tyr Lys Gly Asp Ile Leu Asp Glu Leu Pro Gly Leu Val
            260                 265                 270

Asp Phe Ser Val Phe Leu Lys Leu Ser Thr Lys Gln Lys Glu Ile Val
        275                 280                 285

His Lys Ile Glu Ala Tyr Glu Lys Phe Lys Arg Ser Ala Val Gly Thr
    290                 295                 300

Ala Leu Tyr Ile His Pro Cys Leu Ser Glu Ile Ser Glu Gly Asp Ala
305                 310                 315                 320

Ala Asp Arg Ala Thr Asn Leu Thr Asp Ala Thr Val Asp Ser Leu Ile
                325                 330                 335

Glu Ser Ile Ile Ile Lys Asp Gly Val Lys Ala Lys Phe Phe Phe Asn
            340                 345                 350

Ile Leu Ser Leu Ala Asn Ser Ala Gly Glu Lys Leu Leu Ala Phe Ser
        355                 360                 365

Gln Tyr Ile Leu Pro Met Lys Phe Leu Glu Arg Leu Leu Val Lys Arg
    370                 375                 380

Leu Gly Trp His Val Gly Lys Glu Ile Phe Met Ile Ser Gly Asp Thr
385                 390                 395                 400

Ser Ala Asp Asp Arg Glu Val Ala Met Asp Gln Phe Asn Asn Ser Ala
                405                 410                 415

Asp Ala Lys Val Leu Phe Gly Ser Ile Lys Ala Cys Gly Glu Gly Ile
            420                 425                 430

Ser Leu Val Gly Ala Ser Arg Val Ile Ile Leu Asp Val His Leu Asn
        435                 440                 445

Pro Ser Val Thr Arg Gln Ala Ile Gly Arg Ala Phe Arg Pro Gly Gln
    450                 455                 460
```

<210> SEQ ID NO 9
<211> LENGTH: 453
<212> TYPE: PRT
<213> ORGANISM: Zea mays

<400> SEQUENCE: 9

```
His Gln Val Glu Gly Phe Asn Phe Leu Val Lys Asn Leu Ile Gly Asp
 1               5                  10                  15

Lys Pro Gly Gly Lys Thr Phe Leu Leu Ile Ser Phe Ile Gln Ser Phe
            20                  25                  30
```

```
Met Ala Arg Tyr Pro Ser Ala Arg Pro Leu Val Val Leu Pro Lys Gly
        35                  40                  45

Ile Leu Val Ile Trp Lys Lys Glu Ile Gln Arg Trp Gln Val Gln Asp
    50                  55                  60

Ile Pro Val Tyr Asp Phe Tyr Ser Val Lys Val Glu Lys Arg Val Glu
65                  70                  75                  80

Gln Leu Gln Ile Leu Lys Ser Trp Glu Asp Lys Met Gly Ile Leu Phe
                85                  90                  95

Leu Gly Tyr Lys Gln Phe Ser Thr Ile Val Thr Asp Asp Gly Gly Ser
            100                 105                 110

Lys Val Thr Ala Ala Cys Arg Asp Arg Leu Leu Lys Val Pro Asn Leu
        115                 120                 125

Leu Ile Leu Asp Glu Gly His Thr Pro Arg Asn Lys Glu Thr Asp Val
    130                 135                 140

Leu Glu Ser Leu Ser Arg Val Glu Thr Pro Arg Lys Val Val Leu Ser
145                 150                 155                 160

Gly Thr Leu Phe Gln Asn His Val Glu Glu Val Phe Asn Ile Leu Asn
                165                 170                 175

Leu Val Arg Pro Lys Phe Leu Arg Met Glu Ser Ser Arg Pro Ile Ala
            180                 185                 190

Arg Arg Ile Met Ser Gln Val Glu Ile Phe Gly Arg Ser Ser Lys Gly
        195                 200                 205

Leu Ala Asp Gly Ala Phe Thr Glu Ala Val Glu Gly Thr Leu Leu Asn
    210                 215                 220

Asp Glu Asn Phe Lys Arg Lys Val His Val Ile Arg Gly Leu Arg Glu
225                 230                 235                 240

Leu Thr Arg Asp Val Leu His Tyr Tyr Lys Gly Ala Ile Leu Asp Glu
                245                 250                 255

Leu Pro Gly Leu Val Asp Phe Ser Val Phe Leu Lys Leu Thr Pro Lys
            260                 265                 270

Gln Lys Asp Ile Val His Lys Leu Glu Met His Asp Arg Phe Lys Arg
        275                 280                 285

Ser Ala Val Gly Ser Ala Leu Tyr Ile His Pro Cys Leu Ser Gly Leu
    290                 295                 300

Ser Glu Val Asn Ala Glu Asn Arg Ala His Thr Leu Arg Asp Asp Ser
305                 310                 315                 320

Val Asp Ser Leu Met Asp Ser Ile Asn Val Arg Asp Gly Val Lys Ala
                325                 330                 335

Asn Phe Phe Met Asn Ile Leu Ser Leu Ala Asn Ser Ala Gly Glu Lys
            340                 345                 350

Val Leu Ala Phe Ser Gln Tyr Ile Leu Pro Met Thr Phe Phe Glu Arg
        355                 360                 365

Leu Leu Val Lys Lys Lys Gly Trp His Val Gly Arg Glu Ile Phe Met
    370                 375                 380

Ile Ser Gly Asp Thr Ser Gln Glu Asp Arg Glu Ala Ala Val Asp Arg
385                 390                 395                 400

Phe Asn Ser Ser Ala Asp Ala Lys Val Leu Phe Gly Ser Ile Arg Ala
                405                 410                 415

Cys Gly Glu Gly Ile Ser Ile Val Gly Ala Ser Arg Val Val Ile Leu
            420                 425                 430

Asp Val His Leu Asn Pro Ser Val Thr Arg Gln Ala Ile Gly Arg Ala
        435                 440                 445

Phe Arg Pro Gly Gln
    450
```

<210> SEQ ID NO 10
<211> LENGTH: 472
<212> TYPE: PRT
<213> ORGANISM: Arabidopsis thaliana

<400> SEQUENCE: 10

```
His Gln Thr Glu Gly Phe Arg Phe Leu Cys Asn Asn Leu Ala Ala Asp
 1               5                  10                  15

Glu Pro Gly Gly Cys Ile Leu Ala His Ala Pro Gly Ser Gly Lys Thr
            20                  25                  30

Phe Leu Leu Ile Ser Phe Leu Gln Ser Phe Met Ala Met Asp Pro Gln
        35                  40                  45

Ala Arg Pro Leu Val Val Leu Pro Lys Gly Ile Ile Glu Ser Trp Lys
    50                  55                  60

Arg Glu Phe Thr Leu Trp Glu Val Glu Lys Ile Pro Leu Leu Asp Phe
65                  70                  75                  80

Tyr Ser Val Lys Ala Glu Ser Arg Lys Gln Gln Leu Lys Val Leu Gly
                85                  90                  95

Gln Trp Ile Lys Glu Arg Ser Ile Leu Phe Leu Gly Tyr Gln Gln Phe
            100                 105                 110

Thr Arg Ile Ile Cys Asp Asp Asn Phe Glu Ala Ala Ser Glu Asp Cys
        115                 120                 125

Lys Leu Ile Leu Leu Glu Lys Pro Thr Leu Leu Ile Leu Asp Glu Gly
    130                 135                 140

His Thr Ser Arg Asn Lys Glu Thr Tyr Met Leu Ser Ser Leu Ala Arg
145                 150                 155                 160

Val Lys Thr Arg Arg Lys Val Val Leu Thr Gly Thr Leu Phe Gln Asn
                165                 170                 175

Asn Val Glu Glu Val Phe Asn Ile Leu Asp Leu Val Arg Pro Lys Phe
            180                 185                 190

Leu Lys Arg Pro Gly Thr Arg Glu Ile Val Ser Arg Ile Met Ser Lys
        195                 200                 205

Ala Glu Ile Pro Arg Gly Lys Gln Val Asn Gln Ser Ser Ser Ser Ile
    210                 215                 220

Glu Gly Thr Phe Phe Ala Ala Val Glu Leu Thr Leu Gln Arg Ser Thr
225                 230                 235                 240

Asn Phe Ser Ala Lys Ala Ser Leu Ile Lys Asp Leu Arg Glu Met Thr
                245                 250                 255

Arg Asn Ile Leu His Tyr His Lys Ala Asp Phe Ser Gly Leu Leu Pro
            260                 265                 270

Gly Leu Ser Glu Phe Thr Val Met Leu Asn Leu Ser Ser Ile Gln Arg
        275                 280                 285

Asp Glu Val Lys Gly Leu Arg Lys Met Glu Leu Phe Lys Gln Ile Ser
    290                 295                 300

Leu Gly Ala Ala Leu Tyr Ile His Pro Lys Leu Lys Ser Phe Leu Glu
305                 310                 315                 320

Glu Asn Pro Ser Asn Gly Glu Lys Gly Phe Ser Asp Asn Asn Thr Thr
                325                 330                 335

Val Met Lys Leu Asp Lys Met Leu Lys Lys Ile Asn Val Arg Asp Gly
            340                 345                 350

Val Lys Met Lys Phe Phe Leu Asn Leu Leu Ala Leu Cys Glu Ser Thr
        355                 360                 365

Gly Glu Lys Leu Leu Val Phe Ser Gln Tyr Ile Val Pro Ile Lys Thr
    370                 375                 380
```

```
Leu Glu Arg Leu Met Ser Ser Met Lys Gly Trp Arg Leu Gly Lys Glu
385                 390                 395                 400

Met Phe Thr Ile Thr Gly Asp Ser Ser Asn Glu Gln Arg Glu Trp Ser
                405                 410                 415

Met Glu Arg Phe Asn Asn Ser Leu Glu Ala Lys Val Phe Phe Gly Ser
            420                 425                 430

Ile Lys Ala Cys Gly Glu Gly Ile Ser Leu Val Gly Ala Ser Arg Val
        435                 440                 445

Leu Ile Leu Asp Val His Leu Asn Pro Ser Val Thr Gln Gln Ala Val
    450                 455                 460

Ala Arg Ala Tyr Arg Pro Gly Gln
465                 470


<210> SEQ ID NO 11
<211> LENGTH: 461
<212> TYPE: PRT
<213> ORGANISM: Arabidopsis thaliana

<400> SEQUENCE: 11

His Gln Ile Glu Gly Phe Gln Phe Leu Cys Ser Asn Leu Val Ala Asp
 1               5                  10                  15

Asp Pro Gly Gly Cys Ile Met Ala His Ala Pro Gly Ser Gly Lys Thr
            20                  25                  30

Phe Met Ile Ile Ser Phe Met Gln Ser Phe Leu Ala Lys Tyr Pro Gln
        35                  40                  45

Ala Lys Pro Leu Val Val Leu Pro Lys Gly Ile Leu Pro Thr Trp Lys
    50                  55                  60

Lys Glu Phe Val Arg Trp Gln Val Glu Asp Ile Pro Leu Leu Asp Phe
65                  70                  75                  80

Tyr Ser Ala Lys Ala Glu Asn Arg Ala Gln Gln Leu Ser Ile Leu Lys
                85                  90                  95

Gln Trp Met Glu Lys Lys Ser Ile Leu Phe Leu Gly Tyr Gln Gln Phe
            100                 105                 110

Ser Thr Ile Val Cys Asp Asp Thr Thr Asp Ser Leu Ser Cys Gln Glu
        115                 120                 125

Ile Leu Leu Lys Val Pro Ser Ile Leu Ile Leu Asp Glu Gly His Thr
    130                 135                 140

Pro Arg Asn Glu Asp Thr Asn Leu Leu Gln Ser Leu Ala Gln Val Gln
145                 150                 155                 160

Thr Pro Arg Lys Val Val Leu Ser Gly Thr Leu Tyr Gln Asn His Val
                165                 170                 175

Lys Glu Val Phe Asn Ile Leu Asn Leu Val Arg Pro Lys Phe Leu Lys
            180                 185                 190

Leu Asp Thr Ser Lys Ser Ala Val Lys Arg Ile Leu Ala Tyr Thr Pro
        195                 200                 205

Cys Asp Val Arg Gly Arg Leu Thr Gly Ser Asn Ser Asp Met Ala Ser
    210                 215                 220

Met Phe Asn Glu Thr Val Glu His Thr Leu Gln Lys Ser Glu Asp Phe
225                 230                 235                 240

Thr Val Lys Ile Lys Val Ile Gln Asp Leu Arg Glu Met Thr Lys Lys
                245                 250                 255

Val Leu His Tyr Tyr Lys Gly Asp Phe Leu Asp Glu Leu Pro Gly Leu
            260                 265                 270

Ala Asp Phe Thr Val Val Leu Asn Leu Ser Pro Lys Gln Leu Asn Glu
        275                 280                 285
```

```
Val Lys Lys Leu Arg Arg Glu Lys Arg Lys Phe Lys Val Ser Ala Val
    290                 295                 300

Gly Ser Ala Ile Tyr Leu His Pro Lys Leu Lys Val Phe Ser Asp Lys
305                 310                 315                 320

Ser Asp Asp Val Ser Asp Thr Thr Met Asp Glu Met Val Glu Lys Leu
                325                 330                 335

Asp Leu Asn Glu Gly Val Lys Ala Lys Phe Phe Leu Asn Leu Ile Asn
            340                 345                 350

Leu Cys Asp Ser Ala Gly Glu Lys Leu Leu Val Phe Ser Gln Tyr Leu
        355                 360                 365

Ile Pro Leu Lys Phe Leu Glu Arg Leu Ala Ala Leu Ala Lys Gly Trp
    370                 375                 380

Lys Leu Gly Lys Glu Val Phe Val Leu Thr Gly Asn Thr Ser Ser Glu
385                 390                 395                 400

Gln Arg Glu Trp Ser Met Glu Thr Phe Asn Ser Ser Pro Asp Ala Lys
                405                 410                 415

Ile Phe Phe Gly Ser Ile Lys Ala Cys Gly Glu Gly Ile Ser Leu Val
            420                 425                 430

Gly Ala Ser Arg Ile Leu Ile Leu Asp Val Pro Leu Asn Pro Ser Val
        435                 440                 445

Thr Arg Gln Ala Ile Gly Arg Ala Phe Arg Pro Gly Gln
    450                 455                 460


<210> SEQ ID NO 12
<211> LENGTH: 208
<212> TYPE: PRT
<213> ORGANISM: Zea mays

<400> SEQUENCE: 12

Leu His Tyr Tyr Lys Gly Asp Ile Leu Asp Glu Leu Pro Gly Leu Val
 1               5                  10                  15

Asp Phe Ser Val Phe Leu Lys Leu Thr Pro Lys Gln Lys Asp Ile Ile
            20                  25                  30

Tyr Lys Leu Glu Ala His Asp Arg Gly Gly Gly Phe Phe Phe Gly Ser
        35                  40                  45

Ala Leu Tyr Ile His Pro Cys Val Ser Glu Leu Ser Glu Val Asn Ala
    50                  55                  60

Glu His Arg Ala Asn Thr Phe Arg Asp Asp Leu Val Asp Ser Leu Val
65                  70                  75                  80

Asp Ser Ile Thr Val Arg Asp Gly Val Lys Ala Asn Phe Phe Met Asn
                85                  90                  95

Ile Leu Ser Leu Ala Asn Ser Ala Gly Glu Lys Val Leu Ala Phe Ser
            100                 105                 110

Gln Tyr Ile Ser Pro Met Ile Phe Phe Glu Arg Leu Leu Val Lys Lys
        115                 120                 125

Lys Gly Trp His Val Gly Lys Glu Ile Phe Met Ile Ser Gly Asp Thr
    130                 135                 140

Ser Gln Glu Asp Arg Glu Leu Ala Thr Asp His Phe Asn Asn Ser Ala
145                 150                 155                 160

Asp Ala Lys Val Met Phe Gly Ser Ile Lys Ala Cys Gly Glu Gly Ile
                165                 170                 175

Ser Leu Val Gly Ala Ser Arg Ala Val Ile Leu Asp Val His Leu Asn
            180                 185                 190

Pro Ser Val Thr Arg Gln Ala Ile Gly Arg Ala Phe Arg Pro Gly Gln
        195                 200                 205
```

```
<210> SEQ ID NO 13
<211> LENGTH: 498
<212> TYPE: PRT
<213> ORGANISM: Saccharomyces cerevisiae

<400> SEQUENCE: 13

His Gln Val Glu Gly Val Arg Phe Leu Tyr Arg Cys Val Thr Gly Leu
 1               5                  10                  15

Val Met Lys Asp Tyr Leu Glu Ala Glu Ala Phe Asn Thr Ser Ser Glu
            20                  25                  30

Asp Pro Leu Lys Ser Asp Glu Lys Ala Leu Thr Glu Ser Gln Lys Thr
        35                  40                  45

Glu Gln Asn Asn Arg Gly Ala Tyr Gly Cys Ile Met Ala Asp Glu Met
    50                  55                  60

Gly Leu Gly Lys Thr Leu Gln Cys Ile Ala Leu Met Trp Thr Leu Leu
65                  70                  75                  80

Arg Gln Gly Pro Gln Gly Lys Arg Leu Ile Asp Lys Cys Ile Ile Val
                85                  90                  95

Cys Pro Ser Ser Leu Val Asn Asn Trp Ala Asn Glu Leu Ile Lys Trp
            100                 105                 110

Leu Gly Pro Asn Thr Leu Thr Pro Leu Ala Val Asp Gly Lys Lys Ser
        115                 120                 125

Ser Met Gly Gly Gly Asn Thr Thr Val Ser Gln Ala Ile His Ala Trp
    130                 135                 140

Ala Gln Ala Gln Gly Arg Asn Ile Val Lys Pro Val Leu Ile Ile Ser
145                 150                 155                 160

Tyr Glu Thr Leu Arg Arg Asn Val Asp Gln Leu Lys Asn Cys Asn Val
                165                 170                 175

Gly Leu Met Leu Ala Asp Glu Gly His Arg Leu Lys Asn Gly Asp Ser
            180                 185                 190

Leu Thr Phe Thr Ala Leu Asp Ser Ile Ser Cys Pro Arg Arg Val Ile
        195                 200                 205

Leu Ser Gly Thr Pro Ile Gln Asn Asp Leu Ser Glu Tyr Phe Ala Leu
    210                 215                 220

Leu Ser Phe Ser Asn Pro Gly Leu Leu Gly Ser Arg Ala Glu Phe Arg
225                 230                 235                 240

Lys Asn Phe Glu Asn Pro Ile Leu Arg Gly Arg Asp Ala Asp Ala Thr
                245                 250                 255

Asp Lys Glu Ile Thr Lys Gly Glu Ala Gln Leu Gln Lys Leu Ser Thr
            260                 265                 270

Ile Val Ser Lys Phe Ile Ile Arg Arg Thr Asn Asp Ile Leu Ala Lys
        275                 280                 285

Tyr Leu Pro Cys Lys Tyr Glu His Val Ile Phe Val Asn Leu Lys Pro
    290                 295                 300

Leu Gln Asn Glu Leu Tyr Asn Lys Leu Ile Lys Ser Arg Glu Val Lys
305                 310                 315                 320

Lys Val Val Lys Gly Val Gly Gly Ser Gln Pro Leu Arg Ala Ile Gly
                325                 330                 335

Ile Leu Lys Lys Leu Cys Asn His Pro Asn Leu Leu Asn Phe Glu Asp
            340                 345                 350

Glu Phe Asp Asp Glu Asp Asp Leu Glu Leu Pro Asp Asp Tyr Asn Met
        355                 360                 365

Pro Gly Ser Lys Ala Arg Asp Val Gln Thr Lys Tyr Ser Ala Lys Phe
    370                 375                 380
```

Ser Ile Leu Glu Arg Phe Leu His Lys Ile Lys Thr Glu Ser Asp Asp
385 390 395 400

Lys Ile Val Leu Ile Ser Asn Tyr Thr Gln Thr Leu Asp Leu Ile Glu
405 410 415

Lys Met Cys Arg Tyr Lys His Tyr Ser Ala Val Arg Leu Asp Gly Thr
420 425 430

Met Ser Ile Asn Lys Arg Gln Lys Leu Val Asp Arg Phe Asn Asp Pro
435 440 445

Glu Gly Gln Glu Phe Ile Phe Leu Leu Ser Ser Lys Ala Gly Gly Cys
450 455 460

Gly Ile Asn Leu Ile Gly Ala Asn Arg Leu Ile Leu Met Asp Pro Asp
465 470 475 480

Trp Asn Pro Ala Ala Asp Gln Gln Ala Leu Ala Arg Val Trp Arg Asp
485 490 495

Gly Gln

<210> SEQ ID NO 14
<211> LENGTH: 435
<212> TYPE: PRT
<213> ORGANISM: Arabidopsis thaliana

<400> SEQUENCE: 14

Tyr Gln Leu Lys Gly Val Lys Trp Leu Ile Ser Leu Trp Gln Asn Gly
1 5 10 15

Leu Asn Gly Ile Leu Ala Asp Gln Met Gly Leu Gly Lys Thr Ile Gln
20 25 30

Thr Ile Gly Phe Leu Ser His Leu Lys Gly Asn Gly Leu Asp Gly Pro
35 40 45

Tyr Leu Val Ile Ala Pro Leu Ser Thr Leu Ser Asn Trp Phe Asn Glu
50 55 60

Ile Ala Arg Phe Thr Pro Ser Ile Asn Ala Ile Ile Tyr His Gly Asp
65 70 75 80

Lys Asn Gln Arg Asp Glu Leu Arg Arg Lys His Met Pro Lys Thr Val
85 90 95

Gly Pro Lys Phe Pro Ile Val Ile Thr Ser Tyr Glu Val Ala Met Asn
100 105 110

Asp Ala Lys Arg Ile Leu Arg His Tyr Pro Trp Lys Tyr Val Val Ile
115 120 125

Asp Glu Gly His Arg Leu Lys Asn His Lys Cys Lys Leu Leu Arg Glu
130 135 140

Leu Lys His Leu Lys Met Asp Asn Lys Leu Leu Leu Thr Gly Thr Pro
145 150 155 160

Leu Gln Asn Asn Leu Ser Glu Leu Trp Ser Leu Leu Asn Phe Ile Leu
165 170 175

Pro Asp Ile Phe Thr Ser His Asp Glu Phe Glu Ser Trp Phe Asp Phe
180 185 190

Ser Glu Lys Asn Lys Asn Glu Ala Thr Lys Glu Glu Glu Glu Lys Arg
195 200 205

Arg Ala Gln Val Val Ser Lys Leu His Gly Ile Leu Arg Pro Phe Ile
210 215 220

Leu Arg Arg Met Lys Cys Asp Val Glu Leu Ser Leu Pro Arg Lys Lys
225 230 235 240

Glu Ile Ile Met Tyr Ala Thr Met Thr Asp His Gln Lys Lys Phe Gln
245 250 255

```
Glu His Leu Val Asn Asn Thr Leu Glu Ala His Leu Gly Glu Asn Ala
            260                 265                 270

Ile Arg Gly Gln Gly Trp Lys Gly Lys Leu Asn Asn Leu Val Ile Gln
        275                 280                 285

Leu Arg Lys Asn Cys Asn His Pro Asp Leu Leu Gln Gly Gln Ile Asp
    290                 295                 300

Gly Ser Tyr Leu Tyr Pro Pro Val Glu Glu Ile Val Gly Gln Cys Gly
305                 310                 315                 320

Lys Phe Arg Leu Leu Glu Arg Leu Leu Val Arg Leu Phe Ala Asn Asn
                325                 330                 335

His Lys Val Leu Ile Phe Ser Gln Trp Thr Lys Leu Leu Asp Ile Met
            340                 345                 350

Asp Tyr Tyr Phe Ser Glu Lys Gly Phe Glu Val Cys Arg Ile Asp Gly
        355                 360                 365

Ser Val Lys Leu Asp Glu Arg Arg Arg Gln Ile Lys Asp Phe Ser Asp
    370                 375                 380

Glu Lys Ser Ser Cys Ser Ile Phe Leu Leu Ser Thr Arg Ala Gly Gly
385                 390                 395                 400

Leu Gly Ile Asn Leu Thr Ala Ala Asp Thr Cys Ile Leu Tyr Asp Ser
                405                 410                 415

Asp Trp Asn Pro Gln Met Asp Leu Gln Ala Met Asp Arg Cys His Arg
            420                 425                 430

Ile Gly Gln
        435


<210> SEQ ID NO 15
<211> LENGTH: 433
<212> TYPE: PRT
<213> ORGANISM: Saccharomyces cerevisiae

<400> SEQUENCE: 15

Tyr Gln Ile Lys Gly Leu Gln Trp Met Val Ser Leu Phe Asn Asn His
 1               5                  10                  15

Leu Asn Gly Ile Leu Ala Asp Glu Met Gly Leu Gly Lys Thr Ile Gln
            20                  25                  30

Thr Ile Ser Leu Leu Thr Tyr Leu Tyr Glu Met Lys Asn Ile Arg Gly
        35                  40                  45

Pro Tyr Leu Val Ile Val Pro Leu Ser Thr Leu Ser Asn Trp Ser Ser
    50                  55                  60

Glu Phe Ala Lys Trp Ala Pro Thr Leu Arg Thr Ile Ser Phe Lys Gly
65                  70                  75                  80

Ser Pro Asn Glu Arg Lys Ala Lys Gln Ala Lys Ile Arg Ala Gly Glu
                85                  90                  95

Phe Asp Val Val Leu Thr Thr Phe Glu Tyr Ile Ile Lys Glu Arg Ala
            100                 105                 110

Leu Leu Ser Lys Val Lys Trp Val His Met Ile Ile Asp Glu Gly His
        115                 120                 125

Arg Met Lys Asn Ala Gln Ser Lys Leu Ser Leu Thr Leu Asn Thr His
    130                 135                 140

Tyr His Ala Asp Tyr Arg Leu Ile Leu Thr Gly Thr Pro Leu Gln Asn
145                 150                 155                 160

Asn Leu Pro Glu Leu Trp Ala Leu Leu Asn Phe Val Leu Pro Lys Ile
                165                 170                 175

Phe Asn Ser Val Lys Ser Phe Asp Glu Trp Phe Asn Thr Pro Phe Ala
            180                 185                 190
```

```
Asn Thr Gly Gly Gln Asp Lys Ile Glu Leu Ser Glu Glu Glu Thr Leu
        195                 200                 205

Leu Val Ile Arg Arg Leu His Lys Val Leu Arg Pro Phe Leu Leu Arg
    210                 215                 220

Arg Leu Lys Lys Asp Val Glu Lys Glu Leu Pro Asp Lys Val Glu Lys
225                 230                 235                 240

Val Val Lys Cys Lys Met Ser Ala Leu Gln Gln Ile Met Tyr Gln Gln
                245                 250                 255

Met Leu Lys Tyr Arg Arg Leu Phe Ile Gly Asp Gln Asn Asn Lys Lys
            260                 265                 270

Met Val Gly Leu Arg Gly Phe Asn Asn Gln Ile Met Gln Leu Lys Lys
        275                 280                 285

Ile Cys Asn His Pro Phe Val Phe Glu Glu Val Glu Asp Gln Ile Asn
    290                 295                 300

Pro Thr Arg Glu Thr Asn Asp Asp Ile Trp Arg Val Ala Gly Lys Phe
305                 310                 315                 320

Glu Leu Leu Asp Arg Ile Leu Pro Lys Leu Lys Ala Thr Gly His Arg
                325                 330                 335

Val Leu Ile Phe Phe Gln Met Thr Gln Ile Met Asp Ile Met Glu Asp
            340                 345                 350

Phe Leu Arg Tyr Ile Asn Ile Lys Tyr Leu Arg Leu Asp Gly His Thr
        355                 360                 365

Lys Ser Asp Glu Arg Ser Glu Leu Leu Arg Leu Phe Asn Ala Pro Asp
    370                 375                 380

Ser Glu Tyr Leu Cys Phe Ile Leu Ser Thr Arg Ala Gly Gly Leu Gly
385                 390                 395                 400

Leu Asn Leu Gln Thr Ala Asp Thr Val Ile Ile Phe Asp Thr Asp Trp
                405                 410                 415

Asn Pro His Gln Asp Leu Gln Ala Gln Asp Arg Ala His Arg Ile Gly
            420                 425                 430

Gln
```

<210> SEQ ID NO 16
<211> LENGTH: 6625
<212> TYPE: DNA
<213> ORGANISM: Zea mays

<400> SEQUENCE: 16

```
gcccccaccg cacgcatgga tcgcgccacg ccgcgcgttt gcggccgccg cggcgtatcc      60

caagcggcgg tggaagctgc gccgtcctcc tcccgcgcgc gccgccgcga taaggcgccg     120

gccgttgtca tggaccttgg cgacgacgac tgcggcggtg gcggggccag gaagacggtt     180

ggtggcgctg caggtaggtg cgagggatcc acgaaggctc cttcgcctat gctgccgccg     240

atgatggtgc cggcgggagc ggtggcgctg cggacacgat cgaggaggcg ggcgatgctg     300

gcggcggcag tggtggaaga ggcgccaacg aagaagaaga agaaggaagg agcgatccca     360

gatgccgcgg aggcaacccg tggccacggg agcaaggccg ctgcgacctc gatggcgacg     420

tcgagccata agcggcgcgc tgggacctcg aggtcgacgt cgagagataa gcggcgcgcg     480

cgctcgggac gtgcctcgga gccagctcgc gtgggccgcg cgcgcaagcg caaaaggaac     540

gagttggagg cccccgctcg gagagaacgt gtgaaggcgc catgtgtcag tgaaagtgat     600

gacaacagcg ggcgaggcga tgacgcttct catgacgggg atgcggagcc tcgcggtggg     660

gtcgccattg gcactgatct ggttaacggg gaccatccgg cagctaaagg tgaggatcat     720

attaagagaa gagtgctgtg aatttgaatg atgacttggt ctcatgtaat gcagaggtag     780
```

```
tggaaggtgc tggtgacgag gacacagggg acggagggaa cagtggcctg gcatcgactg     840
ctgatgtggt tgctgaggag atggcaccct ttgaagatga ctacgatgat gagatgttgg     900
aggagcagct tgttggagat gtgattcgtg cttacagtaa tggcagaaac ttagattcag     960
atggagtgga ttgggaggca gaggatgaga tggagttcaa tgacgatgct gacaatagtg    1020
attttatgga tgatgctgac gatagtgatt ttatggatga tgcttatgaa ggtggcaatt    1080
ccaaaccaat tcaaaatcat gctaagttgg aaatacaaga ctgggtgaac cagaaagttg    1140
ttttgagtgg agggaggtgt gaggtgaggg gcgaggggga tctggaggaa gaattgggtg    1200
tgggaaagga agcagatgag gaggacgtgg aaccaaagag tgaagcagct ccaggttctg    1260
ataaaagggt cttgcagtta gaaatcctag gttccgatga ggaaatcaag gtgcttgaaa    1320
atatgagtag tgccccatcc aggaaggcgt cagttcaatc gaagttacca actattccat    1380
cttgtgttgc atggagaacc cgatcatcat ggggggtaaa tcaagataga ctatcgtacg    1440
atacatattt tgaggaatta tctgatgagc caaaagagga tgatgatgat acagaggtgg    1500
aacttgatga agttgaggat gacaacaatg acgatgacag tagtgatgct tatgataaag    1560
atgacgaaga gaaggaggaa gaggaagaag aggctgaaag aagaaaactt aataacagga    1620
tttgcacatc cgatgaagac atgatcaata ttactgttcc tacatcaaga tatgatatgt    1680
ttaagaaaaa aaattcctca agatatgata ttgagtgggt ggaggatgaa gatgcaagtg    1740
ttgatatgtt acagccagtt tcctttaaga aagatagcag ctggaagcct gtggctgttg    1800
gcaacgacac atttactgag caacaaaagc gatcacgatt tacttgggag cttgagagga    1860
ggaaaaagct taagcttgag atgaagacaa atcctttgca tgagcgggat ttggactcag    1920
atccgaactc atcaggttct gaccagatca gaaagtatgg tttcaaaagt gatgggagtc    1980
ataaagttga taggaaaaag aagcatacat cgcccaaatc gggcaagaaa cccagcagcg    2040
caatcatact aaagcggcag tctcttttga agcttttggt agataaaatg agtggtgata    2100
aaagtttagc atcttttcca tttgatcaga atcctcagct tcagtttatt ttcaaagaaa    2160
tgcatccatt ggtattttca tttggagatg aagatctagt agcagctgac aggccagagc    2220
aagatgttgg attggatatg ttatgggctg actttgactt tgctttagag tctgagaata    2280
tcggtactta ttatgatgat gaggtacatt cagtactggt tttcatttta tttttatcta    2340
tcaaaacaca tgcaggtata aatatgtgtg gtttatttat ttgaacactg actctacaac    2400
tagaactatg gtaaaattaa caatgtccaa ctggagatgc actaccatgt tattctcagc    2460
aaaaagtttg tcaatggcga caaacgcaaa aagtttgatg aaacaatctc gatcaaacca    2520
aaaaaactct cattattcac catctggcac aagggcaaag atgcaggaga tgcccctcta    2580
gggagcagaa ctccagctat ttttggagat gcaccatcaa acacatatca gctttgtcat    2640
ttccaaattg cccatgctcc aagggtgatg atcgaattaa gcccattttg ttcctcacca    2700
ttttttttcaa cggaccttgt gaaacctaac catcaaccct tgcttctccc cttgccgatc    2760
attcatcaaa ggaaacatca tctatctgtg gaggacctgc aggctgcagc agtctaaacc    2820
agaattctca tgcaaaaaca cacaatgtga gcaggtgatt gatcatctca gcttgatcac    2880
aaagagcaca gcaggtaggg tgcagaagac tcatcatgca tgctgatcgg cagtccatta    2940
cctattttga gtaagtaacc acaaaagaac caacacttcc tgggccccaa gattttcaaa    3000
ttctttccca agacccaaga ggacagaacc atgaaataaa cccttatcaa cagacttgcc    3060
tcaatcatct acatctatcg ttaacataac taacaagaga agaaataaac catttgagct    3120
cactttgata gtgcaacact tctgtgaaca atatgtgcat gtgaaatgta gcctcctttt    3180
```

```
ctcagaatgc atatatctgt ggtgtttgtc aagggcctca cactgctgtc gtgtccataa   3240
agaaagcaca ggaatcaaca atccttcttc gggaacacta ttgaagctag aacccagaaa   3300
tgtacagaaa aaactattag ggcgtggaaa ttctttctgc attttcttca gtttgatctg   3360
gctctattgt ttctcagatc atgtctacgt catggtagtt ttttttatc gaatgcgcag    3420
gagagatgcg catcattata ttaagagatg aaaaggtcca aaatagacca gcacaagata   3480
gtagaaaagg ccctttatgg tggccaaaaa gtaagataca gaaaatgatc cattaaatca   3540
atcatactat aaatccgacc gaagagggtc ggcaaggtag tttgcagcta atgtgcagga   3600
aacgtcgttt cccagaatag agtaactttg taaacattag aaatgttttt tttcaggtca   3660
agaaatctag ttcacttaaa ggagttacta tagaatagtt tataaccatt atattaagaa   3720
gagatgaaaa ggtccaaaat agaccagcac aagatagtac aaaaggccct ttatggcgga   3780
gtaagataca gaaaatgatc cattaaatca atcctactat aaatccgacc gaagaggggc   3840
agcaaggtag tttgcagcta atgtgcagga aacgtcgttt cccagaatag agtaactttg   3900
taaacattag aaatgttttt ttaggtcaag aactctagtt cacttaaagg agttactata   3960
gaatagttta taaccattaa ggggcaattc agatagcctc agaaggtcaa gaaaacttta   4020
tcatagcctg tgtgaatgtt tagacaaaaa ggaagcagaa atgtttgttc tttgtcaaaa   4080
gtttcatcat cagtgtgttt catttaatga tttccttttg tcccaacatt aatgactcag   4140
ttacatgttg tttttgcgaa tggaattttc taacttggca atgttactca aacatatgta   4200
gtattctgca tatctgatac cacaggttga ttcctactct taattcggca atcaacataa   4260
atagtttcat cttttagaaa ctagacaccc cctactgctt tcatgtaaaa gttatatagc   4320
atttcaaggt cgtgcgtcca tgatatacta ctcgattttt aatgtttatt ttcttgaatg   4380
caagagtttg taccattgca gatactttga tttgccactg tgagaatgac taaatgaact   4440
tattagctta tgttgtattg tagtgtcaag aaggcaatca actagatttt tctcttgcct   4500
cagtaacacc ctgttctcgt gggaagcatg aatttgttat tgatgatcaa atagggatca   4560
gatgcaaata ctgttcgttg gtaaacctgg agatcaaatt catgtttcca tcactggtaa   4620
gctttattat ggtcataaat catgacatct attctacata aatttggtca tttaagtcat   4680
cattttcttt taggtgtcag tgtttggcga gaaatcagca tggccaaatg acaaaggcgt   4740
gaagaataca ctgatgtttc atgatcttta tgaacaagga gtcaatgaca ctgaacaatc   4800
tcaagatatt catcaatatg gaacggtgtg gaatcttatt ccaggggtca tcagtactat   4860
gtatgagcat cagcgtgaag catttgaatt tatgtggaca aatttagttg gtgatattag   4920
acttgatgag ataaagcatg gagcaaaacc tgatgttgtt ggtggatgtg ttatctgtca   4980
tgctcctgga acaggaaaga cacgattagc tattgtattt atccagacat acatgaaagt   5040
gtttccagac tgtcggccag tgattattgc accacgtggt atgctctttg cttgggatga   5100
ggaatttaag aaatggaatg ttgatgttcc ttttcatata ctaaacacaa ctgattacac   5160
tggaaaagag gaccgggaca tatgcaagtt aataaagaaa gaacatagga cagaaaagtt   5220
gacaagacta gtcaaactgc tttcatggaa caaaggccat ggtattcttg gaataagtta   5280
tggtctgtac acaaaaactga cctctgaaaa acctggctgc acagaagaaa acaaagtaag   5340
aagcattctt cttgataacc ctggcttact tgttcttgat gaaggacata cacctaggaa   5400
tgagcgcagt gttatgtgga aactctagg aaatgtgaaa actgagaagc gtataatttt    5460
atctggaact ccttttcaga acaattttct tgagctttac aacattcttt gtctggtaag   5520
gcctagattt ggtgaaatgt tttgacgaa gtcaagagta ggtcgaagac attatgtctc    5580
```

```
aaaaaagcaa aaggataagt tttctgataa atatgaaaag ggtgtttggg catcactgac   5640

tagcaatgta actgatgata atgcggagaa agtaagatca atattgaaac catttgttca   5700

tatacataat ggcaatattc ttcgaactct tccaggactc agggagagtg taattatttt   5760

gaagcctctt ccccttcaaa agagtatcat taaaaaggtg gaaaacattg gttctggtaa   5820

caacttcgaa catgaatatg tcatttcttt agcttctaca caccctttccc ttgtaaccgc   5880

cattaacatg tctgaggagg aagcttcact tattgataaa cctatgcttg ctaaagtgag   5940

atcaaatcca tatgaagggg taaaaacaag atttgtgatc gaagttgttc gtttgtctga   6000

agcattaaga gagaaggttt tgatttttag ccaatttatt cagcctctag agttgattaa   6060

agagcatctt cgcaagttct tcaaatggag agaagggaaa gaaattcttc aaatggatgg   6120

aaagatcctt ccaagatatc gccaggcttc cattgaagcc ttcaataatc caaataatga   6180

ttccagggtg ttacttgcat ctacaagagc atgctgtgaa gggattagct tgacaggtgc   6240

ttcaagaatt gtgcttctag atgttgtttg gaacccagct gttggaaggc aagccatcag   6300

cagagcattt aggataggtc agaagaaatt tgtatataca tataatttga taacttatgg   6360

aacaggtgaa ggtgacaaat atgataggca agcagaaaag gatcacttat ccaagttggt   6420

cttctctaca gaagacgagt tcaataatgt taggaacatg ttatctaaag ctgaaatgga   6480

gcactgttct aagtttatct cagaagataa agttttggag gagatgactt cccacgatca   6540

acttaaagga atgtttttga agatccatta tccaccaact gagtcaaaca ttgtctatag   6600

ttacaatcaa attgctactg agtga                                          6625
```

```
<210> SEQ ID NO 17
<211> LENGTH: 1435
<212> TYPE: PRT
<213> ORGANISM: Zea mays

<400> SEQUENCE: 17

Met Asp Arg Ala Thr Pro Arg Val Cys Gly Arg Arg Gly Val Ser Gln
 1               5                  10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190
```

```
Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590

Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
```

```
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750

Ala Ser Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Gly Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845

Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910

Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Asp Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020

Thr Pro Arg Asn Glu Arg Ser Val Met Trp Lys Thr Leu Gly Asn Val
1025                1030                1035                1040
```

```
Lys Thr Glu Lys Arg Ile Ile Leu Ser Gly Thr Pro Phe Gln Asn Asn
                1045                1050                1055

Phe Leu Glu Leu Tyr Asn Ile Leu Cys Leu Val Arg Pro Arg Phe Gly
            1060                1065                1070

Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180

Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280

Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Ala Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340

Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435
```

<210> SEQ ID NO 18
<211> LENGTH: 6518
<212> TYPE: DNA
<213> ORGANISM: Zea mays

<400> SEQUENCE: 18

```
ctagcgcccc caccgcacgc atggatcgcg ccacgccgcg cgtttgcggc cgccgcggcg     60
tatcccaagc ggcggtggaa gctgcgccgt cctcctcccg cgcgcgccgc cgcgataagg    120
cgccggccgt tgtcatggac cttggcgacg acgactgcgg cggtggcggg gccaggaaga    180
cggttggtgg cgctgcaggt aggtgcgagg gatccacgaa ggctcctttg cctctgctgc    240
cgccgatgat ggtgccggcg ggagcggtgg cgctgcggac acgatcgagg aggcgggcga    300
tgctggcggc ggcagtggtg gaagaggcgc caacgaagaa gaagaagaag gaaggagcga    360
tcccagatgc cgcggaggcg ccccgtggcc acgggagcaa ggccgctgct acctcgatgg    420
cgacgtcgag ccataagcgg cgcgctggga cctcgaggtc gacgtcgaga gataagcggc    480
gcgcgcgctc gggacgtgcc tcggagccag ctcgcgtggg ccgcgcgcgc aagcgcaaaa    540
ggaacgagtt ggaggccccc gctcggagag aacgtgtgaa ggcgccatgt gtcagtgaaa    600
gtgatgacaa cagcgggcga ggcgatgacg cttctcatga cggggatgcg gagcctcgcg    660
tcggggtcgc cattggcact gatctggtta acggggatca tccggcagct aaaggtgagg    720
atcatattaa gagaagagtg ctgtgaattt gaatgatgac ttggtctcat gtaatgcaga    780
ggtagtggaa ggtgctggtg acgaggacac aggggacgga gggaacagtg gcctggcatc    840
gactgctgat gtgtttgctg aggagatggc accctttgaa gatgactacg atgatgagat    900
gttggaggag cagcttgttg gagatgtgat tcgtgcttac agtaatggca gaaacttcga    960
ttcagatgga gtggattggg aggcagagga tgagatggag ttcaatgacg atgctgacaa   1020
tagtgatttt atggatgatg ctgacgatag tgattttatg gatgatgctt atgaaggtgg   1080
caattccaaa ccaattcaaa atcatgctaa gttggaaata caagactggg tgaaccagaa   1140
agttgttttg agtggaggga ggtgtgaggc gaggggcgag gggatctgg aggaagaatt   1200
ggatgtggga aaggaagcag atgaggagga cgtggaacca aagagtgaag cggctccagg   1260
ttctgataaa agggtcttgc agttagaaat cctaggttcc gatgaggaaa tcaaggtgct   1320
tgaaaatatg agtagtgccc catccaggaa ggcgtcagtt caatcgaagt taccaactat   1380
tccatcttgt gttgcatgga gaacccgatc atcatggggg gtaaatcaag atagactatc   1440
gtacgataca tattttgagg aattatctga tgagccaaaa gaggatgatg atgatacaga   1500
ggtggaactt gatgaagttg aggatgacaa caatgacgat gacagtagtg atgcttatga   1560
taaagatgac gaagagaagg aggaagagga agaagaggct gaaagaagaa aacttaataa   1620
caggatttgc acatccgatg aagacatgat caatattact gttcctacat caagatatga   1680
tatgtttaag aaaaaaaatt cctcaagata tgatattgag tgggtggagg atgaagatgc   1740
aagtgttgat atgttacagc cagtttcctt taagaaagat agcagctgga agcctgtggc   1800
tgttggcaac gacacattta ctgagcaaca aaagcgatca cgatttactt gggagcttga   1860
gaggaggaaa aagcttaagc ttgagatgaa gacaaatcct ttgcatgagc gggatttgga   1920
ctcagatccg aactcatcag gttctgacca gatcagaaag tatggtttca aaagtgatgg   1980
gagtcataaa gttgatagga aaaagaagca tacatcgccc aaatcgggca agaaacccag   2040
cagcgcaatc atactaaagc ggcagtctct tttgaagctt ttggtagata aaatgagtgg   2100
tgataaaagt ttagcatctt ttccatttga tcagaatcct cagcttcagt ttattttcaa   2160
agaaatgcat ccattggtat tttcatttgg agatgaagat ctagtagcag ctgacaggcc   2220
agagcaagat gttggattgg atatgttatg ggctgacttt gactttgctt tagagtctga   2280
gaatatcggt acttattatg atgatgaggt acattcagta ctggttttca ttttattttt   2340
```

```
atctatcaaa acacatgcag gtataaatat gtgtggttta tttatttgaa cacttactct   2400

acaactagaa ctatggtaaa attaacaatg tccaactgga gatgcactac catgttattc   2460

tcagcaaaaa gtttgtcaat ggcgacaaac gcaaaaagtt tgatgaaaca atctcgatca   2520

aaccaaaaaa ctctcattat tcaccatctg gcacaagggc aaagatgcag gagatgcccc   2580

ttgctctggc caaaccccaa tcatgcaact cctctctagg gagcagaact ccagctattt   2640

ttggagatgc accatcaaac acatatcagc tttgtcattt ccaaattgcc catgctccaa   2700

gggtgatgat cgaattaagc ccattttgtt cctcaccatt tttttcaatg gaccttgtga   2760

aacctaacca tcaacccttg cttctcccct tgccgatcat tcatcaaagg aaacatcatc   2820

tatatttgga ggacctgcag gctgcagcag tctaaaccag aattctaatg caaaaacaca   2880

caatgtgagc aggtgattga tcatctcagc ttgatcacaa agagcacagc aggtagggtg   2940

cagaagactc atcatgcatg ctgatcggca gtccattatc tattatgagt aagtaaccac   3000

aaaagaacca acacttcctg gggcccaaga ttttcaaatt ctttcccaag gcccaagagg   3060

acagaaccat gaaataaacc cttatcaaca gacttgcctc aatcatctac atctatcgtt   3120

aacataacta acaagagaag aaataaacca tttgagctca ctttgatagt acaacacttc   3180

tgtgaacaat atgtgcatgt gaaatgtagc ctcgttttct cataatgcat atatctgtgg   3240

tgtttgtcaa gggcctcaca ctgctgtagt gtccataaag aaagcacagg aatcaacaat   3300

ccttcttcgg gaacactatt gaagctagaa cccagaaatg tacagaaaaa actattaggg   3360

catggaaagc attctttctg cattttcttc agtttgatct ggctctattg tttctcagat   3420

catgtctacg tcatggtagt ttttttctc gaatgcgcag gagagatgcg catcattata   3480

ttaagaagag atgaaaaggt ccaaaataga ccagcacaag atagtacaaa aggcccttta   3540

tggcggccaa aaagtaagat acagaaaatg atccattaaa tcaatcctac tataaatccg   3600

accgaagagg ggcagcaagg tagtttgcag ctaatgtgca ggaaacgtcg tttcccagaa   3660

tagagtaact ttgtaaacat tagaaatgtt tttttaggtc aagaaatcta gttcacttaa   3720

aggagttact atagaatagt ttataaccat aactttaagg ggcaattcag atagcctcag   3780

aaggtcaaga aaactttatt atagcctgtg tgaatgttta gacaaaaagg aagcagaaat   3840

gattgttctt tgtcaaaagt ttcatcatca gtgtgtttca tttaatgatt tccttttgtc   3900

ccaacattaa tgacttagtt acatgttgtt tttgcgaatt aaattttcta acttgacgac   3960

gttactcaaa catatgtagt attctgcata tctgatacca caggttggtt cctactctta   4020

attcggcaat caacataaat agtttcatct tttagaaact agacaccctt actgctttca   4080

tgtaaaagtt atatagcatt tcaaggtcgt gcgtccatga tatactactc gatttttaat   4140

gtttattttc ttaaatgcaa gagtttgtac cattgtagat actttgattt gccactgtga   4200

gaatgactaa atgaacttat tagcttatgt tgtattgtag tgtcaagaag gcaatcaact   4260

agatttttct cttgccccag taacaccctg ttctcgtggg aagcatgaat ttgttattga   4320

tgatcaaata gggatcagat gcaaatactg ttccttggta aacctggaga tcaaattcat   4380

gtttccatca ctggtaagct ttattatggt cataaatcat gacatctatt ctacagtata   4440

agcttttaaa tttggtcatt taagtcatca ttttctttta ggtgtcagtg tttgccgaga   4500

aatcagcatg gccaaatgac aaaggcgtga aaaatacact gatgtttcat gatctttatg   4560

aacaaggagt caatgacact gaacaatctc aagatattca tcaatatgga acggtgtgga   4620

atcttattcc aggggtcatc agtactatgt atgagcatca gcgtgaagca tttgaattta   4680

tgtggacaaa tttagttggt gatattagac ttgatgagat aaagcatgga gcaaaacctg   4740
```

```
atgttgttgg tggatgtgtt atctgtcatg ctcctggaac aggaaagaca cgattagcta   4800

ttgtgtttat ccagacatac atgaaggtgt ttccagactg tcggccagtg attattgcac   4860

cacgtggtat gctctttgct tgggatgagg aatttaagaa atggaatgtt gatgttcctt   4920

ttcatatact aaacacaact gattacactg gaaaagagga tcgggagata tgcaagttaa   4980

taaagaaaga acataggaca gaaaagttga caagactagt caaactgctt tcatggaaca   5040

aaggtcatgg tattcttgga ataagttatg gtctgtacac aaaactgacc tctgaaaaac   5100

ctggctgcac agaagaaaac aaagtaagaa gcattcttct tgataaccct ggcttacttg   5160

ttcttgatga aggacataca cctaggaatg aacgcagtgt tatgtggaaa actctaggaa   5220

atgtgaaaac tgagaagcgt ataattttat ccggaactcc ttttcagaac aattttcttg   5280

agctttacaa cattctttgt ctggtaaggc ctagatttgg tgaaatgttt ttgacgaagt   5340

caagagtagg tcgaagacat tatgtctcaa aaaagcaaaa ggataagttt tctgataaat   5400

atgaaaaggg tgtttgggca tcactgacta gcaatgtaac tgatgataat gcggaaaaag   5460

taagatcaat attgaaacca tttgttcata tacataatgg caatattctt cgaactcttc   5520

caggactcag ggagagtgta attattctga agcctcttcc ccttcaaaag agtatcatta   5580

aaaaggtgga aaacattggt tctggtaaca acttcgaaca tgaatatgtc atttctttag   5640

cttctacaca cccttccctt gtaaccgcca ttaacatgtc tgaggaggaa gcttcactta   5700

ttgataaacc tatgcttgct aaagtgagat caaatccata tgaaggggta aaaacaagat   5760

ttgtgatcga agttgttcgt ttgtctgaag cattaagaga gaaggttttg atttttagcc   5820

aatttattca gcctctagag ttgataaaag agcatcttcg caagttcttc aaatggagag   5880

aagggaaaga aattcttcaa atggatggaa agatccttcc aagatatcgc caggcttcca   5940

ttgaagcctt caataatcca aataatgatt ccagggtgtt acttgcatct acaagagcat   6000

gctgtgaagg gattagcttg acaggtgctt caagaattgt gcttctagat gttgtttgga   6060

acccagctgt tggaaggcaa gccatcagca gagcatttag gataggtcag aagaaatttg   6120

tatatacata taatttgata acttatggaa caggtgaagg tgacaaatat gataggcaag   6180

cagaaaagga tcacttatcc aagttggtct tctctacaga agacgagttc aataatgtta   6240

ggaacatgtt atctaaagct gaaatggagc actgttctaa gtttatctca gaagataaag   6300

ttttggagga gatgacttcc cacgatcaac ttaaaggaat gtttttgaag atccattatc   6360

caccaactga gtcaaacatt gtctatagtt acaatcaaat tgctactgag tgaagtcggt   6420

ggtaatagtc agtaccagat tgtttgtcta tatctatggt atgctcaaaa tttctgactt   6480

cttcgtatag atgctgtagc tttacattag ttctgtta                           6518
```

```
<210> SEQ ID NO 19
<211> LENGTH: 1435
<212> TYPE: PRT
<213> ORGANISM: Zea mays

<400> SEQUENCE: 19

Met Asp Arg Ala Thr Pro Arg Val Cys Gly Arg Arg Gly Val Ser Gln
 1               5                  10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60
```

```
Ser Thr Lys Ala Pro Leu Pro Leu Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Pro Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Val Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Phe Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Phe Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Ala Arg Gly Glu Gly Asp Leu
        355                 360                 365

Glu Glu Glu Leu Asp Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
```

```
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590

Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750

Ala Pro Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Ala Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845

Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910
```

```
Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Glu Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020

Thr Pro Arg Asn Glu Arg Ser Val Met Trp Lys Thr Leu Gly Asn Val
1025                1030                1035                1040

Lys Thr Glu Lys Arg Ile Ile Leu Ser Gly Thr Pro Phe Gln Asn Asn
                1045                1050                1055

Phe Leu Glu Leu Tyr Asn Ile Leu Cys Leu Val Arg Pro Arg Phe Gly
            1060                1065                1070

Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180

Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280

Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Ala Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340
```

```
Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435


<210> SEQ ID NO 20
<211> LENGTH: 6715
<212> TYPE: DNA
<213> ORGANISM: Zea mays

<400> SEQUENCE: 20

atggatcgcg ccacgccgcg cgtttgcggc cgccgcggcg tatcccaagc ggcggtggaa     60

gctgcgccgt cctcctcccg cgcgcgccgc cgcgataagg cgccggccgt tgtcatggac    120

cttggcgacg acgactgcgg cggtggcggg gccaggaaga cggttggtgg cgctgcaggt    180

aggtgcgagg gatccacgaa ggctccttcg cctatgctgc cgccgatgat ggtgccggcg    240

ggagcggtgg cgctgcggac acgatcgagg aggcgggcga tgctggcggc ggcagtggtg    300

gaagaggcgc caacgaagaa gaagaagaag gaaggagcga tcccagatgc cgcggaggca    360

acccgtggcc acgggagcaa ggccgctgcg acctcgatgg cgacgtcgag ccataagcgg    420

cgcgctggga cctcgaggtc gacgtcgaga gataagcggc gcgcgcgctc gggacgtgcc    480

tcggagccag ctcgcgtggg ccgcgcgcgc aagcgcaaaa ggaacgagtt ggaggccccc    540

gctcggagag aacgtgtgaa ggcgccatgt gtcagtgaaa gtgatgacaa cagcgggcga    600

ggcgatgacg cttctcatga cggggatgcg gagcctcgcg gcggggtcgc cattggcact    660

gatctggtta acggggacca tccggcagct aaaggtgagg atcatattaa gagaagagtg    720

ctgtgaattt gaatgatgac ttggtctcat gtaatgcaga ggtagtggaa ggtgctggtg    780

acgaggacac aggggacgga gggaacagtg gcctggcatc gactgctgat gtggttgctg    840

aggagatggc accctttgaa gatgactacg atgatgagat gttggaggag cagcttgttg    900

gagatgtgat tcgtgcttac agtaatggca gaaacttaga ttcagatgga gtggattggg    960

aggcagagga tgagatggag ttcaatgacg atgctgacaa tagtgatttt atggatgatg   1020

ctgacgatag tgattttatg gatgatgctt atgaaggtgg caattccaaa ccaattcaaa   1080

atcatgctaa gttggaaata caagactggg tgaaccagaa agttgttttg agtggaggga   1140

ggtgtgaggt gaggggcgag gggatctgg aggaagaatt gggtgtggga aaggaagcag    1200

atgaggagga cgtggaacca aagagtgaag cagctccagg ttctgataaa agggtcttgc   1260

agttagaaat cctaggttcc gatgaggaaa tcaaggtgct tgaaaatatg agtagtgccc   1320

catccaggaa ggcgtcagtt caatcgaagt taccaactat tccatcttgt gttgcatgga   1380

gaacccgatc atcatggggg gtaaatcaag atagactatc gtacgataca tattttgagg   1440

aattatctga tgagccaaaa gaggatgatg atgatacaga ggtggaactt gatgaagttg   1500

aggatgacaa caatgacgat gacagtagtg atgcttatga taaagatgac gaagagaagg   1560

aggaagagga agaagaggct gaaagaagaa aacttaataa caggatttgc acatccgatg   1620
```

```
aagacatgat caatattact gttcctacat caagatatga tatgtttaag aaaaaaaatt   1680
cctcaagata tgatattgag tgggtggagg atgaagatgc aagtgttgat atgttacagc   1740
cagtttcctt taagaaagat agcagctgga agcctgtggc tgttggcaac gacacattta   1800
ctgagcaaca aaagcgatca cgatttactt gggagcttga gaggaggaaa aagcttaagc   1860
ttgagatgaa gacaaatcct ttgcatgagc gggatttgga ctcagatccg aactcatcag   1920
gttctgacca gatcagaaag tatggtttca aaagtgatgg gagtcataaa gttgatagga   1980
aaaagaagca tacatcgccc aaatcgggca agaaacccag cagcgcaatc atactaaagc   2040
ggcagtctct tttgaagctt ttggtagata aaatgagtgg tgataaaagt ttagcatctt   2100
ttccatttga tcagaatcct cagcttcagt ttattttcaa agaaatgcat ccattggtat   2160
tttcatttgg agatgaagat ctagtagcag ctgacaggcc agagcaagat gttggattgg   2220
atatgttatg ggctgacttt gactttgctt tagagtctga gaatatcggt acttattatg   2280
atgatgaggt acattcagta ctggttttca ttttattttt atctatcaaa acacatgcag   2340
gtataaatat gtgtggttta tttatttgaa cactgactct acaactagaa ctatggtaaa   2400
attaacaatg tccaactgga gatgcactac catgttattc tcagcaaaaa gtttgtcaat   2460
ggcgacaaac gcaaaaagtt tgatgaaaca atctcgatca aaccaaaaaa actctcatta   2520
ttcaccatct ggcacaaggg caaagatgca ggagatgccc ctctagggag cagaactcca   2580
gctatttttg gagatgcacc atcaaacaca tatcagcttt gtcatttcca aattgcccat   2640
gctccaaggg tgatgatcga attaagccca ttttgttcct caccattttt ttcaacggac   2700
cttgtgaaac ctaaccatca acccttgctt ctccccttgc cgatcattca tcaaaggaaa   2760
catcatctat ctgtggagga cctgcaggct gcagcagtct aaaccagaat tctcatgcaa   2820
aaacacacaa tgtgagcagg tgattgatca tctcagcttg atcacaaaga gcacagcagg   2880
tagggtgcag aagactcatc atgcatgctg atcggcagtc cattacctat tttgagtaag   2940
taaccacaaa agaaccaaca cttcctgggc cccaagattt tcaaattctt tcccaagacc   3000
caagaggaca gaaccatgaa ataaaccctt atcaacagac ttgcctcaat catctacatc   3060
tatcgttaac ataactaaca agagaagaaa taaaccattt gagctcactt tgatagtgca   3120
acacttctgt gaacaatatg tgcatgtgaa atgtagcctc cttttctcag aatgcatata   3180
tctgtggtgt ttgtcaaggg cctcacactg ctgtcgtgtc cataaagaaa gcacaggaat   3240
caacaatcct tcttcgggaa cactattgaa gctagaaccc agaaatgtac agaaaaaact   3300
attagggcgt ggaaattctt tctgcatttt cttcagtttg atctggctct attgtttctc   3360
agatcatgtc tacgtcatgg tagttttttt ttatcgaatg cgcaggagag atgcacatca   3420
ttatattaag agatgaaaag gtccaaaata gaccagcaca agatagtaga aaaggccctt   3480
tatggtggcc aaaaagtaag atacagaaaa tgatccatta aatcaatcat actataaatc   3540
cgaccgaaga gggtcggcaa ggtagtttgc agctaatgtg caggaaacgt cgtttcccag   3600
aatagagtaa ctttgtaaac attagaaatg ttttttttca ggtcaagaaa tctagttcac   3660
ttaaaggagt tactatagaa tagtttataa ccattatatt aagaagagat gaaaaggtcc   3720
aaaatagacc agcacaagat agtacaaaag gccctttatg gcggagtaag atacagaaaa   3780
tgatccatta aatcaatcct actataaatc cgaccgaaga ggggcagcaa ggtagtttgc   3840
agctaatgtg caggaaacgt cgtttcccag aatagagtaa ctttgtaaac attagaaatg   3900
tttttttagg tcaagaactc tagttcactt aaaggagtta ctatagaata gtttataacc   3960
attaaggggc aattcagata gcctcagaag gtcaagaaaa ctttatcata gcctgtgtga   4020
```

```
atgtttagac aaaaaggaag cagaaatgtt tgttctttgt caaaagtttc atcatcagtg   4080
tgtttcattt aatgatttcc ttttgtccca acattaatga ctcagttaca tgttgttttt   4140
gcgaatggaa ttttctaact tggcaatgtt actcaaacat atgtagtatt ctgcatatct   4200
gataccacag gttgattcct actcttaatt cggcaatcaa cataaatagt ttcatctttt   4260
agaaactaga cacccctac tgctttcatg taaaagttat atagcatttc aaggtcgtgc   4320
gtccatgata tactactcga tttttaatgt ttattttctt gaatgcaaga gtttgtacca   4380
ttgcagatac tttgatttgc cactgtgaga atgactaaat gaacttatta gcttatgttg   4440
tattgtagtg tcaagaaggc aatcaactag atttttctct tgcctcagta acaccctgtt   4500
ctcgtgggaa gcatgaattt gttattgatg atcaaatagg gatcagatgc aaatactgtt   4560
cgttggtaaa cctggagatc aaattcatgt ttccatcact ggtaagcttt attatggtca   4620
taaatcatga catctattct acataaattt ggtcatttaa gtcatcattt tcttttaggt   4680
gtcagtgttt ggcgagaaat cagcatggcc aaatgacaaa ggcgtgaaga atacactgat   4740
gtttcatgat ctttatgaac aaggagtcaa tgacactgaa caatctcaag atattcatca   4800
atatggaacg gtgtggaatc ttattccagg ggtcatcagt actatgtatg agcatcagcg   4860
tgaagcattt gaatttatgt ggacaaattt agttggtgat attagacttg atgagataaa   4920
gcatggagca aaacctgatg ttgttggtgg atgtgttatc tgtcatgctc ctggaacagg   4980
aaagacacga ttagctattg tatttatcca gacatacatg aaagtgtttc cagactgtcg   5040
gccagtgatt attgcaccac gtggtatgct ctttgcttgg gatgaggaat ttaagaaatg   5100
gaatgttgat gttcctttc atatactaaa cacaactgat tacactggaa aagaggaccg   5160
ggacatatgc aagttaataa agaaagaaca taggacagaa aagttgacaa gactagtcaa   5220
actgctttca tggaacaaag gccatggtat tcttggaata agttatggtc tgtacacaaa   5280
actgacctct gaaaaacctg gctgcacaga agaaaacaaa gtaagaagca ttcttcttga   5340
taaccctggc ttacttgttc ttgatgaagg acatacacct aggaatgagc gcagtgttat   5400
gtggaaaact ctaggaaatg tgaaaactga gaagcgtata attttatctg gaactccttt   5460
tcagaacaat ttcttgagc tttacaacat tctttgtctg gtaaggccta gatttggtga   5520
aatgtttttg acgaagtcaa gagtaggtcg aagacattat gtctcaaaaa agcaaaagga   5580
taagttttct gataaatatg aaaagggtgt ttgggcatca ctgactagca atgtaactga   5640
tgataatgcg gagaaagtaa gatcaatatt gaaaccattt gttcatatac ataatggcaa   5700
tattcttcga actcttccag gactcaggga gagtgtaatt attttgaagc ctcttcccct   5760
tcaaaagagt atcattaaaa aggtggaaaa cattggttct ggtaacaact tcgaacatga   5820
atatgtcatt tctttagctt ctacacaccc ttcccttgta accgccatta acatgtctga   5880
ggaggaagct tcacttattg ataaacctat gcttgctaaa gtgagatcaa atccatatga   5940
aggggtaaaa acaagatttg tgatcgaagt tgttcgtttg tctgaagcat taagagagaa   6000
ggttttgatt tttagccaat ttattcagcc tctagagttg attaaagagc atcttcgcaa   6060
gttcttcaaa tggagagaag ggaaagaaat tcttcaaatg gatggaaaga tccttccaag   6120
atatcgccag gcttccattg aagccttcaa taatccaaat aatgattcca gggtgttact   6180
tgcatctaca agagcatgct gtgaagggat tagcttgaca ggtgcttcaa gaattgtgct   6240
tctagatgtt gtttggaacc cagctgttgg aaggcaagcc atcagcagag catttaggat   6300
aggtcagaag aaatttgtat atacatataa tttgataact tatggaacag gtgaaggtga   6360
caaatatgat aggcaagcag aaaaggatca cttatccaag ttggtcttct ctacagaaga   6420
```

```
cgagttcaat aatgttagga acatgttatc taaagctgaa atggagcact gttctaagtt   6480

tatctcagaa gataaagttt tggaggagat gacttcccac gatcaactta aaggaatgtt   6540

tttgaagatc cattatccac caactgagtc aaacattgtc tatagttaca atcaaattgc   6600

tactgagtga agtcggtggt aatagtcagc accagattgt ttgtctatat ctatggtatg   6660

ctcaaaattt ctgacttctt cgtatagatg ctgtagcttt atattagttc tgtta        6715


<210> SEQ ID NO 21
<211> LENGTH: 1435
<212> TYPE: PRT
<213> ORGANISM: Zea mays

<400> SEQUENCE: 21

Met Asp Arg Ala Thr Pro Arg Val Cys Gly Arg Arg Gly Val Ser Gln
1               5                   10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
```

```
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590

Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750
```

```
Ala Ser Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Gly Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845

Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910

Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Asp Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020

Thr Pro Arg Asn Glu Arg Ser Val Met Trp Lys Thr Leu Gly Asn Val
1025                1030                1035                1040

Lys Thr Glu Lys Arg Ile Ile Leu Ser Gly Thr Pro Phe Gln Asn Asn
                1045                1050                1055

Phe Leu Glu Leu Tyr Asn Ile Leu Cys Leu Val Arg Pro Arg Phe Gly
            1060                1065                1070

Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180
```

```
Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280

Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Ala Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340

Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435

<210> SEQ ID NO 22
<211> LENGTH: 6715
<212> TYPE: DNA
<213> ORGANISM: Zea mays

<400> SEQUENCE: 22

atggatcgcg ccacgccgcg cgtttgcggc cgccgcggcg tatcccaagc ggcggtggaa      60

gctgcgccgt cctcctcccg cgcgcgccgc cgcgataagg cgccggccgt tgtcatggac     120

cttggcgacg acgactgcgg cggtggcggg gccaggaaga cggttggtgg cgctgcaggt     180

aggtgcgagg gatccacgaa ggctccttcg cctatgctgc cgccgatgat ggtgccggcg     240

ggagcggtgg cgctgcggac acgatcgagg aggcgggcga tgctggcggc ggcagtggtg     300

gaagaggcgc caacgaagaa gaagaagaag gaaggagcga tcccagatgc cgcggaggca     360

acccgtggcc acgggagcaa ggccgctgcg acctcgatgg cgacgtcgag ccataagcgg     420

cgcgctggga cctcgaggtc gacgtcgaga gataagcggc gcgcgcgctc gggacgtgcc     480

tcggagccag ctcgcgtggg ccgcgcgcgc aagcgcaaaa ggaacgagtt ggaggccccc     540

gctcggagag aacgtgtgaa ggcgccatgt gtcagtgaaa gtgatgacaa cagcgggcga     600

ggcgatgacg cttctcatga cggggatgcg gagcctcgcg gcggggtcgc cattggcact     660

gatctggtta acggggacca tccggcagct aaaggtgagg atcatattaa gagaagagtg     720
```

```
ctgtgaattt gaatgatgac ttggtctcat gtaatgcaga ggtagtggaa ggtgctggtg    780
acgaggacac aggggacgga gggaacagtg gcctggcatc gactgctgat gtggttgctg    840
aggagatggc accctttgaa gatgactacg atgatgagat gttggaggag cagcttgttg    900
gagatgtgat tcgtgcttac agtaatggca gaaacttaga ttcagatgga gtggattggg    960
aggcagagga tgagatggag ttcaatgacg atgctgacaa tagtgatttt atggatgatg   1020
ctgacgatag tgattttatg gatgatgctt atgaaggtgg caattccaaa ccaattcaaa   1080
atcatgctaa gttggaaata caagactggg tgaaccagaa agttgttttg agtggaggga   1140
ggtgtgaggt gaggggcgag ggggatctgg aggaagaatt gggtgtggga aaggaagcag   1200
atgaggagga cgtggaacca aagagtgaag cagctccagg ttctgataaa agggtcttgc   1260
agttagaaat cctaggttcc gatgaggaaa tcaaggtgct tgaaaatatg agtagtgccc   1320
catccaggaa ggcgtcagtt caatcgaagt taccaactat tccatcttgt gttgcatgga   1380
gaacccgatc atcatggggg gtaaatcaag atagactatc gtacgataca tattttgagg   1440
aattatctga tgagccaaaa gaggatgatg atgatacaga ggtggaactt gatgaagttg   1500
aggatgacaa caatgacgat gacagtagtg atgcttatga taaagatgac gaagagaagg   1560
aggaagagga agaagaggct gaaagaagaa aacttaataa caggatttgc acatccgatg   1620
aagacatgat caatattact gttcctacat caagatatga tatgtttaag aaaaaaaatt   1680
cctcaagata tgatattgag tgggtggagg atgaagatgc aagtgttgat atgttacagc   1740
cagtttcctt taagaaagat agcagctgga agcctgtggc tgttggcaac gacacattta   1800
ctgagcaaca aaagcgatca cgatttactt gggagcttga gaggaggaaa aagcttaagc   1860
ttgagatgaa gacaaatcct ttgcatgagc gggatttgga ctcagatccg aactcatcag   1920
gttctgacca gatcagaaag tatggtttca aaagtgatgg gagtcataaa gttgatagga   1980
aaaagaagca tacatcgccc aaatcgggca agaaacccag cagcgcaatc atactaaagc   2040
ggcagtctct tttgaagctt ttggtagata aaatgagtgg tgataaaagt ttagcatctt   2100
ttccatttga tcagaatcct cagcttcagt ttattttcaa agaaatgcat ccattggtat   2160
tttcatttgg agatgaagat ctagtagcag ctgacaggcc agagcaagat gttggattgg   2220
atatgttatg ggctgacttt gactttgctt tagagtctga gaatatcggt acttattatg   2280
atgatgaggt acattcagta ctggttttca ttttattttt atctatcaaa acacatgcag   2340
gtataaatat gtgtggttta tttatttgaa cactgactct acaactagaa ctatggtaaa   2400
attaacaatg tccaactgga gatgcactac catgttattc tcagcaaaaa gtttgtcaat   2460
ggcgacaaac gcaaaaagtt tgatgaaaca atctcgatca aaccaaaaaa actctcatta   2520
ttcaccatct ggcacaaggg caaagatgca ggagatgccc ctctagggag cagaactcca   2580
gctatttttg gagatgcacc atcaaacaca tatcagcttt gtcatttcca aattgcccat   2640
gctccaaggg tgatgatcga attaagccca ttttgttcct caccattttt ttcaacggac   2700
cttgtgaaac ctaaccatca acccttgctt ctccccttgc cgatcattca tcaaaggaaa   2760
catcatctat ctgtggagga cctgcaggct gcagcagtct aaaccagaat tctcatgcaa   2820
aaacacacaa tgtgagcagg tgattgatca tctcagcttg atcacaaaga gcacagcagg   2880
tagggtgcag aagactcatc atgcatgctg atcggcagtc cattacctat tttgagtaag   2940
taaccacaaa agaaccaaca cttcctgggc cccaagattt tcaaattctt tcccaagacc   3000
caagaggaca gaaccatgaa ataaaccctt atcaacagac ttgcctcaat catctacatc   3060
tatcgttaac ataactaaca agagaagaaa taaaccattt gagctcactt tgatagtgca   3120
```

```
acacttctgt gaacaatatg tgcatgtgaa atgtagcctc cttttctcag aatgcatata   3180
tctgtggtgt ttgtcaaggg cctcacactg ctgtcgtgtc cataaagaaa gcacaggaat   3240
caacaatcct tcttcgggaa cactattgaa gctagaaccc agaaatgtac agaaaaaact   3300
attagggcgt ggaaattctt tctgcatttt cttcagtttg atctggctct attgtttctc   3360
agatcatgtc tacgtcatgg tagttttttt ttatcgaatg cgcaggagag atgcgcatca   3420
ttatattaag agatgaaaag gtccaaaata gaccagcaca agatagtaga aaaggccctt   3480
tatggtggcc aaaaagtaag atacagaaaa tgatccatta aatcaatcat actataaatc   3540
cgaccgaaga gggtcggcaa ggtagtttgc agctaatgtg caggaaacgt cgtttcccag   3600
aatagagtaa ctttgtaaac attagaaatg tttttttca ggtcaagaaa tctagttcac   3660
ttaaaggagt tactatagaa tagtttataa ccattatatt aagaagagat gaaaaggtcc   3720
aaaatagacc agcacaagat agtacaaaag gccctttatg gcggagtaag atacagaaaa   3780
tgatccatta aatcaatcct actataaatc cgaccgaaga ggggcagcaa ggtagtttgc   3840
agctaatgtg caggaaacgt cgtttcccag aatagagtaa ctttgtaaac attagaaatg   3900
tttttttagg tcaagaactc tagttcactt aaaggagtta ctatagaata gtttataacc   3960
attaaggggc aattcagata gcctcagaag gtcaagaaaa ctttatcata gcctgtgtga   4020
atgtttagac aaaaaggaag cagaaatgtt tgttctttgt caaaagtttc atcatcagtg   4080
tgtttcattt aatgatttcc ttttgtccca acattaatga ctcagttaca tgttgttttt   4140
gcgaatggaa ttttctaact tggcaatgtt actcaaacat atgtagtatt ctgcatatct   4200
gataccacag gttgattcct actcttaatt cggcaatcaa cataaatagt ttcatctttt   4260
agaaactaga cacccctac tgctttcatg taaaagttat atagcatttc aaggtcgtgc   4320
gtccatgata tactactcga tttttaatgt ttattttctt gaatgcaaga gtttgtacca   4380
ttgcagatac tttgatttgc cactgtgaga atgactaaat gaacttatta gcttatgttg   4440
tattgtagtg tcaagaaggc aatcaactag atttttctct tgcctcagta acaccctgtt   4500
ctcgtgggaa gcatgaattt gttattgatg atcaaatagg gatcagatgc aaatactgtt   4560
cgttggtaaa cctggagatc aaattcatgt ttccatcact ggtaagcttt attatggtca   4620
taaatcatga catctattct acataaattt ggtcatttaa gtcatcattt tcttttaggt   4680
gtcagtgttt ggcgagaaat cagcatggcc aaatgacaaa ggcgtgaaga atacactgat   4740
gtttcatgat ctttatgaac aaggagtcaa tgacactgaa caatctcaag atattcatca   4800
atatggaacg gtgtggaatc ttattccagg ggtcatcagt actatgtatg agcatcagcg   4860
tgaagcattt gaatttatgt ggacaaattt agttggtgat attagacttg atgagataaa   4920
gcatggagca aaacctgatg ttgttggtgg atgtgttatc tgtcatgctc ctggaacagg   4980
aaagacacga ttagctattg tatttatcca gacatacatg aaagtgtttc cagactgtcg   5040
gccagtgatt attgcaccac gtggtatgct ctttgcttgg gatgaggaat ttaagaaatg   5100
gaatgttgat gttccttttc atatactaaa cacaactgat tacactggaa aagaggaccg   5160
ggacatatgc aagttaataa agaaagaaca taggacagaa aagttgacaa gactagtcaa   5220
actgctttca tggaacaaag gccatggtat tcttggaata agttatggtc tgtacacaaa   5280
actgacctct gaaaaacctg gctgcacaga agaaaacaaa gtaagaagca ttcttcttga   5340
taaccctggc ttacttgttc ttgatgaagg acatacacct aggaatgagc gcagtgttat   5400
gtggaaaact ctaggaaatg tgaaaactga gaagcgtata attttatctg gaactccttt   5460
tcagaacaat tttcttgagc tttacaacat tctttgtctg gtaaggccta gatttggtga   5520
```

```
aatgtttttg acgaagtcaa gagtaggtcg aagacattat gtctcaaaaa agcaaaagga   5580

taagttttct gataaatatg aaaagggtgt ttgggcatca ctgactagca atgtaactga   5640

tgataatgcg gagaaagtaa gatcaatatt gaaaccattt gttcatatac ataatggcaa   5700

tattcttcga actcttccag gactcaggga gagtgtaatt attttgaagc ctcttcccct   5760

tcaaaagagt atcattaaaa aggtggaaaa cattggttct ggtaacaact tcgaacatga   5820

atatgtcatt tctttagctt ctacacaccc ttcccttgta accgccatta acatgtctga   5880

ggaggaagct tcacttattg ataaacctat gcttgctaaa gtgagatcaa atccatatga   5940

aggggtaaaa acaagatttg tgatcgaagt tgttcgtttg tctgaagcat taagagagaa   6000

ggttttgatt tttagccaat ttattcagcc tctagagttg attaaagagc atcttcgcaa   6060

gttcttcaaa tggagagaag ggaaagaaat tcttcaaatg gatggaaaga tccttccaag   6120

atatcgccag gcttccattg aagccttcaa taatccaaat aatgattcca gggtgttact   6180

tgcatctaca agagcatgct gtgaagggat tagcttgaca ggtgcttcaa gaattgtgct   6240

tctagatgtt gtttggaacc cagttgttgg aaggcaagcc atcagcagag catttaggat   6300

aggtcagaag aaatttgtat atacatataa tttgataact tatggaacag gtgaaggtga   6360

caaatatgat aggcaagcag aaaaggatca cttatccaag ttggtcttct ctacagaaga   6420

cgagttcaat aatgttagga acatgttatc taaagctgaa atggagcact gttctaagtt   6480

tatctcagaa gataaagttt tggaggagat gacttcccac gatcaactta aaggaatgtt   6540

tttgaagatc cattatccac caactgagtc aaacattgtc tatagttaca atcaaattgc   6600

tactgagtga agtcggtggt aatagtcagc accagattgt ttgtctatat ctatggtatg   6660

ctcaaaattt ctgacttctt cgtatagatg ctgtagcttt atattagttc tgtta        6715
```

<210> SEQ ID NO 23
<211> LENGTH: 1435
<212> TYPE: PRT
<213> ORGANISM: Zea mays

<400> SEQUENCE: 23

```
Met Asp Arg Ala Thr Pro Arg Val Cys Gly Arg Arg Gly Val Ser Gln
 1               5                  10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
```

```
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590
```

```
Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750

Ala Ser Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Gly Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845

Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910

Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Asp Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020
```

```
Thr Pro Arg Asn Glu Arg Ser Val Met Trp Lys Thr Leu Gly Asn Val
1025                1030                1035                1040

Lys Thr Glu Lys Arg Ile Ile Leu Ser Gly Thr Pro Phe Gln Asn Asn
                1045                1050                1055

Phe Leu Glu Leu Tyr Asn Ile Leu Cys Leu Val Arg Pro Arg Phe Gly
            1060                1065                1070

Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180

Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280

Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Val Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340

Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435
```

<210> SEQ ID NO 24
<211> LENGTH: 6732
<212> TYPE: DNA
<213> ORGANISM: Zea mays

<400> SEQUENCE: 24

```
ccccaccgca cgcatggatc gcgccacgcc gcgcgtttgc ggccgccgcg gcgtatccca      60
agcggcggtg gaagctgcgc cgtcctcctc ccgcgcgcgc cgccgcgata aggcgccggc     120
cgttgtcatg gaccttggcg acgacgactg cggcggtggc ggggccagga agacggttgg     180
tggcgctgca ggtaggtgcg agggatccac gaaggctcct tcgcctatgc tgccgccgat     240
gatggtgccg gcgggagcgg tggcgctgcg gacacgatcg aggaggcggg cgatgctggc     300
ggcggcagtg gtggaagagg cgccaacgaa gaagaagaag aaggaaggag cgatcccaga     360
tgccgcggag gcaacccgtg gccacgggag caaggccgct gcgacctcga tggcgacgtc     420
gagccataag cggcgcgctg ggacctcgag gtcgacgtcg agagataagc ggcgcgcgcg     480
ctcgggacgt gcctcggagc cagctcgcgt gggccgcgcg cgcaagcgca aaaggaacga     540
gttggaggcc cccgctcgga gagaacgtgt gaaggcgcca tgtgtcagtg aaagtgatga     600
caacagcggg cgaggcgatg acgcttctca tgacggggat gcggagcctc gcggcggggt     660
cgccattggc actgatctgg ttaacgggga ccatccggca gctaaaggtg aggatcatat     720
taagagaaga gtgctgtgaa tttgaatgat gacttggtct catgtaatgc agaggtagtg     780
gaaggtgctg gtgacgagga cacaggggac ggagggaaca gtggcctggc atcgactgct     840
gatgtggttg ctgaggagat ggcacccttt gaagatgact acgatgatga gatgttggag     900
gagcagcttg ttggagatgt gattcgtgct tacagtaatg gcagaaactt agattcagat     960
ggagtggatt gggaggcaga ggatgagatg gagttcaatg acgatgctga caatagtgat    1020
tttatggatg atgctgacga tagtgatttt atggatgatg cttatgaagg tggcaattcc    1080
aaaccaattc aaaatcatgc taagttggaa atacaagact gggtgaacca gaaagttgtt    1140
ttgagtggag ggaggtgtga ggtgagggge gagggggatc tggaggaaga attgggtgtg    1200
ggaaaggaag cagatgagga ggacgtggaa ccaaagagtg aagcagctcc aggttctgat    1260
aaaagggtct tgcagttaga aatcctaggt tccgatgagg aaatcaaggt gcttgaaaat    1320
atgagtagtg ccccatccag gaaggcgtca gttcaatcga agttaccaac tattccatct    1380
tgtgttgcat ggagaacccg atcatcatgg ggggtaaatc aagatagact atcgtacgat    1440
acatattttg aggaattatc tgatgagcca aaagaggatg atgatgatac agaggtggaa    1500
cttgatgaag ttgaggatga caacaatgac gatgacagta gtgatgctta tgataaagat    1560
gacgaagaga aggaggaaga ggaagaagag gctgaaagaa gaaaacttaa taacaggatt    1620
tgcacatccg atgaagacat gatcaatatt actgttccta catcaagata tgatatgttt    1680
aagaaaaaaa attcctcaag atatgatatt gagtgggtgg aggatgaaga tgcaagtgtt    1740
gatatgttac agccagtttc ctttaagaaa gatagcagct ggaagcctgt ggctgttggc    1800
aacgacacat ttactgagca acaaaagcga tcacgattta cttgggagct tgagaggagg    1860
aaaaagctta agcttgagat gaagacaaat cctttgcatg agcgggattt ggactcagat    1920
ccgaactcat caggttctga ccagatcaga aagtatggtt tcaaaagtga tgggagtcat    1980
aaagttgata ggaaaaagaa gcatacatcg cccaaatcgg gcaagaaacc cagcagcgca    2040
atcatactaa agcggcagtc tcttttgaag cttttggtag ataaaatgag tggtgataaa    2100
agtttagcat cttttccatt tgatcagaat cctcagcttc agtttatttt caaagaaatg    2160
catccattgg tattttcatt tggagatgaa gatctagtag cagctgacag gccagagcaa    2220
```

```
gatgttggat tggatatgtt atgggctgac tttgactttg ctttagagtc tgagaatatc   2280
ggtacttatt atgatgatga ggtacattca gtactggttt tcattttatt tttatctatc   2340
aaaacacatg caggtataaa tatgtgtggt ttatttattt gaacactgac tctacaacta   2400
gaactatggt aaaattaaca atgtccaact ggagatgcac taccatgtta ttctcagcaa   2460
aaagtttgtc aatggcgaca aacgcaaaaa gtttgatgaa acaatctcga tcaaaccaaa   2520
aaaactctca ttattcacca tctggcacaa gggcaaagat gcaggagatg cccctctagg   2580
gagcagaact ccagctattt ttggagatgc accatcaaac acatatcagc tttgtcattt   2640
ccaaattgcc catgctccaa gggtgatgat cgaattaagc ccattttgtt cctcaccatt   2700
tttttcaacg gaccttgtga aacctaacca tcaacccttg cttctcccct tgccgatcat   2760
tcatcaaagg aaacatcatc tatctgtgga ggacctgcag gctgcagcag tctaaaccag   2820
aattctcatg caaaaacaca caatgtgagc aggtgattga tcatctcagc ttgatcacaa   2880
agagcacagc aggtagggtg cagaagactc atcatgcatg ctgatcggca gtccattacc   2940
tattttgagt aagtaaccac aaaagaacca acacttcctg ggccccaaga ttttcaaatt   3000
ctttcccaag acccaagagg acagaaccat gaaataaacc cttatcaaca gacttgcctc   3060
aatcatctac atctatcgtt aacataacta acaagagaag aaataaacca tttgagctca   3120
ctttgatagt gcaacacttc tgtgaacaat atgtgcatgt gaaatgtagc ctccttttct   3180
cagaatgcat atatctgtgg tgtttgtcaa gggcctcaca ctgctgtcgt gtccataaag   3240
aaagcacagg aatcaacaat ccttcttcgg gaacactatt gaagctagaa cccagaaatg   3300
tacagaaaaa actattaggg cgtggaaatt ctttctgcat tttcttcagt ttgatctggc   3360
tctattgttt ctcagatcat gtctacgtca tggtagtttt tttttatcga atgcgcagga   3420
gagatgcgca tcattatatt aagagatgaa aaggtccaaa atagaccagc acaagatagt   3480
agaaaaggcc ctttatggtg gccaaaaagt aagatacaga aaatgatcca ttaaatcaat   3540
catactataa atccgaccga agagggtcgg caaggtagtt tgcagctaat gtgcaggaaa   3600
cgtcgtttcc cagaatagag taactttgta aacattagaa atgttttttt tcaggtcaag   3660
aaatctagtt cacttaaagg agttactata gaatagttta taaccattat attaagaaga   3720
gatgaaaagg tccaaaatag accagcacaa gatagtacaa aaggcccttt atggcggagt   3780
aagatacaga aaatgatcca ttaaatcaat cctactataa atccgaccga agaggggcag   3840
caaggtagtt tgcagctaat gtgcaggaaa cgtcgtttcc cagaatagag taactttgta   3900
aacattagaa atgttttttt aggtcaagaa ctctagttca cttaaaggag ttactataga   3960
atagtttata accattaagg ggcaattcag atagcctcag aaggtcaaga aaactttatc   4020
atagcctgtg tgaatgttta gacaaaaagg aagcagaaat gtttgttctt tgtcaaaagt   4080
ttcatcatca gtgtgtttca tttaatgatt tccttttgtc ccaacattaa tgactcagtt   4140
acatgttgtt tttgcgaatg gaattttcta acttggcaat gttactcaaa catatgtagt   4200
attctgcata tctgatacca caggttgatt cctactctta attcggcaat caacataaat   4260
agtttcatct tttagaaact agacaccccc tactgctttc atgtaaaagt tatatagcat   4320
ttcaaggtcg tgcgtccatg atatactact cgatttttaa tgtttatttt cttgaatgca   4380
agagtttgta ccattgcaga tactttgatt tgccactgtg agaatgacta aatgaactta   4440
ttagcttatg ttgtattgta gtgtcaagaa ggcaatcaac tagatttttc tcttgcctca   4500
gtaacaccct gttctcgtgg gaagcatgaa tttgttattg atgatcaaat agggatcaga   4560
tgcaaatact gttcgttggt aaacctggag atcaaattca tgtttccatc actggtaagc   4620
```

```
tttattatgg tcataaatca tgacatctat tctacataaa tttggtcatt taagtcatca   4680

ttttctttta ggtgtcagtg tttggcgaga aatcagcatg gccaaatgac aaaggcgtga   4740

agaatacact gatgtttcat gatctttatg aacaaggagt caatgacact gaacaatctc   4800

aagatattca tcaatatgga acggtgtgga atcttattcc aggggtcatc agtactatgt   4860

atgagcatca gcgtgaagca tttgaattta tgtggacaaa tttagttggt gatattagac   4920

ttgatgagat aaagcatgga gcaaaacctg atgttgttgg tggatgtgtt atctgtcatg   4980

ctcctggaac aggaaagaca cgattagcta ttgtatttat ccagacatac atgaaagtgt   5040

ttccagactg tcggccagtg attattgcac cacgtggtat gctctttgct tgggatgagg   5100

aatttaagaa atggaatgtt gatgttcctt ttcatatact aaacacaact gattacactg   5160

gaaaagagga ccgggacata tgcaagttaa taaagaaaga acataggaca gaaaagttga   5220

caagactagt caaactgctt tcatggaaca aaggccatgg tattcttgga ataagttatg   5280

gtctgtacac aaaactgacc tctgaaaaac ctggctgcac agaagaaaac aaagtaagaa   5340

gcattcttct tgataaccct ggcttacttg ttcttgatga aggacataca cctaggaatg   5400

agcgcaatgt tatgtggaaa actctaggaa atgtgaaaac tgagaagcgt ataattttat   5460

ctggaactcc ttttcagaac aattttcttg agctttacaa cattctttgt ctggtaaggc   5520

ctagatttgg tgaaatgttt ttgacgaagt caagagtagg tcgaagacat tatgtctcaa   5580

aaaagcaaaa ggataagttt tctgataaat atgaaaaggg tgtttgggca tcactgacta   5640

gcaatgtaac tgatgataat gcggagaaag taagatcaat attgaaacca tttgttcata   5700

tacataatgg caatattctt cgaactcttc caggactcag ggagagtgta attattttga   5760

agcctcttcc ccttcaaaag agtatcatta aaaaggtgga aaacattggt tctggtaaca   5820

acttcgaaca tgaatatgtc atttctttag cttctacaca cccttccctt gtaaccgcca   5880

ttaacatgtc tgaggaggaa gcttcactta ttgataaacc tatgcttgct aaagtgagat   5940

caaatccata tgaaggggta aaaacaagat ttgtgatcga agttgttcgt ttgtctgaag   6000

cattaagaga gaaggttttg atttttagcc aatttattca gcctctagag ttgattaaag   6060

agcatcttcg caagttcttc aaatggagag aagggaaaga aattcttcaa atggatggaa   6120

agatccttcc aagatatcgc caggcttcca ttgaagcctt caataatcca aataatgatt   6180

ccagggtgtt acttgcatct acaagagcat gctgtgaagg gattagcttg acaggtgctt   6240

caagaattgt gcttctagat gttgtttgga acccagctgt tggaaggcaa gccatcagca   6300

gagcatttag gataggtcag aagaaatttg tatatacata taatttgata acttatggaa   6360

caggtgaagg tgacaaatat gataggcaag cagaaaagga tcacttatcc aagttggtct   6420

tctctacaga agacgagttc aataatgtta ggaacatgtt atctaaagct gaaatggagc   6480

actgttctaa gtttatctca gaagataaag ttttggagga gatgacttcc cacgatcaac   6540

ttaaaggaat gtttttgaag atccattatc caccaactga gtcaaacatt gtctatagtt   6600

acaatcaaat tgctactgag tgaagtcggt ggtaatagtc agcaccagat tgtttgtcta   6660

tatctatggt atgctcaaaa tttctgactt cttcgtatag atgctgtagc tttatattag   6720

ttctgttatg ca                                                       6732
```

<210> SEQ ID NO 25
<211> LENGTH: 1435
<212> TYPE: PRT
<213> ORGANISM: Zea mays

<400> SEQUENCE: 25

```
Met Asp Arg Ala Thr Pro Arg Val Cys Gly Arg Arg Gly Val Ser Gln
1               5                   10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
```

```
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590

Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750

Ala Ser Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Gly Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845
```

```
Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910

Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Asp Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020

Thr Pro Arg Asn Glu Arg Asn Val Met Trp Lys Thr Leu Gly Asn Val
1025                1030                1035                1040

Lys Thr Glu Lys Arg Ile Ile Leu Ser Gly Thr Pro Phe Gln Asn Asn
                1045                1050                1055

Phe Leu Glu Leu Tyr Asn Ile Leu Cys Leu Val Arg Pro Arg Phe Gly
            1060                1065                1070

Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180

Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280
```

```
Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Ala Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340

Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435
```

<210> SEQ ID NO 26
<211> LENGTH: 6731
<212> TYPE: DNA
<213> ORGANISM: Zea mays

<400> SEQUENCE: 26

```
cgcccccacc gcacgcatgg atcgcgccac gccgcgcgtt tgcggccgcc gcggcgtatc     60

ccaagcggcg gtggaagctg cgccgtcctc ctcccgcgcg cgccgccgcg ataaggcgcc    120

ggccgttgtc atggaccttg gcgacgacga ctgcggcggt ggcggggcca ggaagacggt    180

tggtggcgct gcaggtaggt gcgagggatc cacgaaggct ccttcgccta tgctgccgcc    240

gatgatggtg ccggcgggag cggtggcgct gcggacacga tcgaggaggc gggcgatgct    300

ggcggcggca gtggtggaag aggcgccaac gaagaagaag aagaaggaag gagcgatccc    360

agatgccgcg gaggcaaccc gtggccacgg gagcaaggcc gctgcgacct cgatggcgac    420

gtcgagccat aagcggcgcg ctgggacctc gaggtcgacg tcgagagata agcggcgcgc    480

gcgctcggga cgtgcctcgg agccagctcg cgtgggccgc gcgcgcaagc gcaaaaggaa    540

cgagttggag gcccccgctc ggagagaacg tgtgaaggcg ccatgtgtca gtgaaagtga    600

tgacaacagc gggcgaggcg atgacgcttc tcatgacggg gatgcggagc ctcgcggcgg    660

ggtcgccatt ggcactgatc tggttaacgg ggaccatccg gcagctaaag gtgaggatca    720

tattaagaga agagtgctgt gaatttgaat gatgacttgg tctcatgtaa tgcagaggta    780

gtggaaggtg ctggtgacga ggacacaggg gacggaggga acagtggcct ggcatcgact    840

gctgatgtgg ttgctgagga gatggcaccc tttgaagatg actacgatga tgagatgttg    900

gaggagcagc ttgttggaga tgtgattcgt gcttacagta atggcagaaa cttagattca    960

gatggagtgg attgggaggc agaggatgag atggagttca atgacgatgc tgacaatagt   1020

gattttatgg atgatgctga cgatagtgat tttatggatg atgcttatga aggtggcaat   1080

tccaaaccaa ttcaaaatca tgctaagttg gaaatacaag actgggtgaa ccagaaagtt   1140

gttttgagtg gagggaggtg tgaggtgagg ggcgaggggg atctggagga agaattgggt   1200

gtgggaaagg aagcagatga ggaggacgtg gaaccaaaga gtgaagcagc tccaggttct   1260
```

-continued

```
gataaaaggg tcttgcagtt agaaatccta ggttccgatg aggaaatcaa ggtgcttgaa   1320

aatatgagta gtgccccatc caggaaggcg tcagttcaat cgaagttacc aactattcca   1380

tcttgtgttg catggagaac ctgatcatca tggggggtaa atcaagatag actatcgtac   1440

gatacatatt ttgaggaatt atctgatgag ccaaaagagg atgatgatga tacagaggtg   1500

gaacttgatg aagttgagga tgacaacaat gacgatgaca gtagtgatgc ttatgataaa   1560

gatgacgaag agaaggagga agaggaagaa gaggctgaaa gaagaaaact taataacagg   1620

atttgcacat ccgatgaaga catgatcaat attactgttc ctacatcaag atatgatatg   1680

tttaagaaaa aaaattcctc aagatatgat attgagtggg tggaggatga agatgcaagt   1740

gttgatatgt tacagccagt ttcctttaag aaagatagca gctggaagcc tgtggctgtt   1800

ggcaacgaca catttactga gcaacaaaag cgatcacgat ttacttggga gcttgagagg   1860

aggaaaaagc ttaagcttga gatgaagaca aatcctttgc atgagcggga tttggactca   1920

gatccgaact catcaggttc tgaccagatc agaaagtatg gtttcaaaag tgatgggagt   1980

cataaagttg ataggaaaaa gaagcataca tcgcccaaat cgggcaagaa acccagcagc   2040

gcaatcatac taaagcggca gtctcttttg aagcttttgg tagataaaat gagtggtgat   2100

aaaagtttag catcttttcc atttgatcag aatcctcagc ttcagtttat tttcaaagaa   2160

atgcatccat tggtattttc atttggagat gaagatctag tagcagctga caggccagag   2220

caagatgttg gattggatat gttatgggct gactttgact ttgctttaga gtctgagaat   2280

atcggtactt attatgatga tgaggtacat tcagtactgg ttttcatttt atttttatct   2340

atcaaaacac atgcaggtat aaatatgtgt ggtttattta tttgaacact gactctacaa   2400

ctagaactat ggtaaaatta acaatgtcca actggagatg cactaccatg ttattctcag   2460

caaaaagttt gtcaatggcg acaaacgcaa aaagtttgat gaaacaatct cgatcaaacc   2520

aaaaaaactc tcattattca ccatctggca caagggcaaa gatgcaggag atgcccctct   2580

agggagcaga actccagcta tttttggaga tgcaccatca aacacatatc agctttgtca   2640

tttccaaatt gcccatgctc caagggtgat gatcgaatta agcccatttt gttcctcacc   2700

attttttca acggaccttg tgaaacctaa ccatcaaccc ttgcttctcc ccttgccgat   2760

cattcatcaa aggaaacatc atctatctgt ggaggacctg caggctgcag cagtctaaac   2820

cagaattctc atgcaaaaac acacaatgtg agcaggtgat tgatcatctc agcttgatca   2880

caaagagcac agcaggtagg gtgcagaaga ctcatcatgc atgctgatcg gcagtccatt   2940

acctattttg agtaagtaac cacaaaagaa ccaacacttc ctgggcccca agattttcaa   3000

attctttccc aagacccaag aggacagaac catgaaataa acccttatca acagacttgc   3060

ctcaatcatc tacatctatc gttaacataa ctaacaagag aagaaataaa ccatttgagc   3120

tcactttgat agtgcaacac ttctgtgaac aatatgtgca tgtgaaatgt agcctccttt   3180

tctcagaatg catatatctg tggtgtttgt caagggcctc acactgctgt cgtgtccata   3240

aagaaagcac aggaatcaac aatccttctt cgggaacact attgaagcta gaacccagaa   3300

atgtacagaa aaaactatta gggcgtggaa attctttctg cattttcttc agtttgatct   3360

ggctctattg tttctcagat catgtctacg tcatggtagt ttttttttat cgaatgcgca   3420

ggagagatgc gcatcattat attaagagat gaaaaggtcc aaaatagacc agcacaagat   3480

agtagaaaag gccctttatg gtggccaaaa agtaagatac agaaaatgat ccattaaatc   3540

aatcatacta taaatccgac cgaagagggt cggcaaggta gtttgcagct aatgtgcagg   3600

aaacgtcgtt tcccagaata gagtaacttt gtaaacatta gaaatgtttt ttttcaggtc   3660
```

```
aagaaatcta gttcacttaa aggagttact atagaatagt ttataaccat tatattaaga   3720
agagatgaaa aggtccaaaa tagaccagca caagatagta caaaaggccc tttatggcgg   3780
agtaagatac agaaaatgat ccattaaatc aatcctacta taaatccgac cgaagagggg   3840
cagcaaggta gtttgcagct aatgtgcagg aaacgtcgtt tcccagaata gagtaacttt   3900
gtaaacatta gaaatgtttt tttaggtcaa gaactctagt tcacttaaag gagttactat   3960
agaatagttt ataaccatta aggggcaatt cagatagcct cagaaggtca agaaaacttt   4020
atcatagcct gtgtgaatgt ttagacaaaa aggaagcaga aatgtttgtt ctttgtcaaa   4080
agtttcatca tcagtgtgtt tcatttaatg atttcctttt gtcccaacat taatgactca   4140
gttacatgtt gtttttgcga atggaatttt ctaacttggc aatgttactc aaacatatgt   4200
agtattctgc atatctgata ccacaggttg attcctactc ttaattcggc aatcaacata   4260
aatagtttca tcttttagaa actagacacc ccctactgct ttcatgtaaa agttatatag   4320
catttcaagg tcgtgcgtcc atgatatact actcgatttt taatgtttat tttcttgaat   4380
gcaagagttt gtaccattgc agatactttg atttgccact gtgagaatga ctaaatgaac   4440
ttattagctt atgttgtatt gtagtgtcaa gaaggcaatc aactagattt ttctcttgcc   4500
tcagtaacac cctgttctcg tgggaagcat gaatttgtta ttgatgatca aatagggatc   4560
agatgcaaat actgttcgtt ggtaaacctg gagatcaaat tcatgtttcc atcactggta   4620
agctttatta tggtcataaa tcatgacatc tattctacat aaatttggtc atttaagtca   4680
tcattttctt ttaggtgtca gtgtttggcg agaaatcagc atggccaaat gacaaaggcg   4740
tgaagaatac actgatgttt catgatcttt atgaacaagg agtcaatgac actgaacaat   4800
ctcaagatat tcatcaatat ggaacggtgt ggaatcttat tccaggggtc atcagtacta   4860
tgtatgagca tcagcgtgaa gcatttgaat ttatgtggac aaatttagtt ggtgatatta   4920
gacttgatga gataaagcat ggagcaaaac ctgatgttgt tggtggatgt gttatctgtc   4980
atgctcctgg aacaggaaag acacgattag ctattgtatt tatccagaca tacatgaaag   5040
tgtttccaga ctgtcggcca gtgattattg caccacgtgg tatgctcttt gcttgggatg   5100
aggaatttaa gaaatggaat gttgatgttc cttttcatat actaaacaca actgattaca   5160
ctggaaaaga ggaccgggac atatgcaagt taataaagaa agaacatagg acagaaaagt   5220
tgacaagact agtcaaactg ctttcatgga acaaaggcca tggtattctt ggaataagtt   5280
atggtctgta cacaaaactg acctctgaaa aacctggctg cacagaagaa aacaaagtaa   5340
gaagcattct tcttgataac cctggcttac ttgttcttga tgaaggacat acacctagga   5400
atgagcgcag tgttatgtgg aaaactctag gaaatgtgaa aactgagaag cgtataattt   5460
tatctggaac tccttttcag aacaattttc ttgagcttta caacattctt tgtctggtaa   5520
ggcctagatt tggtgaaatg tttttgacga agtcaagagt aggtcgaaga cattatgtct   5580
caaaaaagca aaaggataag ttttctgata aatatgaaaa gggtgtttgg gcatcactga   5640
ctagcaatgt aactgatgat aatgcggaga aagtaagatc aatattgaaa ccatttgttc   5700
atatacataa tggcaatatt cttcgaactc ttccaggact cagggagagt gtaattattt   5760
tgaagcctct tccccttcaa aagagtatca ttaaaaaggt ggaaaacatt ggttctggta   5820
acaacttcga acatgaatat gtcatttctt tagcttctac acacccttcc cttgtaaccg   5880
ccattaacat gtctgaggag gaagcttcac ttattgataa acctatgctt gctaaagtga   5940
gatcaaatcc atatgaaggg gtaaaaacaa gatttgtgat cgaagttgtt cgtttgtctg   6000
aagcattaag agagaaggtt ttgattttta gccaatttat tcagcctcta gagttgatta   6060
```

```
aagagcatct tcgcaagttc ttcaaatgga gagaagggaa agaaattctt caaatggatg   6120

gaaagatcct tccaagatat cgccaggctt ccattgaagc cttcaataat ccaaataatg   6180

attccagggt gttacttgca tctacaagag catgctgtga agggattagc ttgacaggtg   6240

cttcaagaat tgtgcttcta gatgttgttt ggaacccagc tgttggaagg caagccatca   6300

gcagagcatt taggataggt cagaagaaat ttgtatatac atataatttg ataacttatg   6360

gaacaggtga aggtgacaaa tatgataggc aagcagaaaa ggatcactta tccaagttgg   6420

tcttctctac agaagacgag ttcaataatg ttaggaacat gttatctaaa gctgaaatgg   6480

agcactgttc taagtttatc tcagaagata aagttttgga ggagatgact tcccacgatc   6540

aacttaaagg aatgtttttg aagatccatt atccaccaac tgagtcaaac attgtctata   6600

gttacaatca aattgctact gagtgaagtc ggtggtaata gtcagcacca gattgtttgt   6660

ctatatctat ggtatgctca aaatttctga cttcttcgta tagatgctgt agctttatat   6720

tagttctgtt a                                                        6731


<210> SEQ ID NO 27
<211> LENGTH: 440
<212> TYPE: PRT
<213> ORGANISM: Zea mays

<400> SEQUENCE: 27

Met Asp Arg Ala Thr Pro Arg Val Cys Gly Arg Arg Gly Val Ser Gln
 1               5                  10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220

Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255
```

```
Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr
        435                 440
```

<210> SEQ ID NO 28
<211> LENGTH: 6731
<212> TYPE: DNA
<213> ORGANISM: Zea mays

<400> SEQUENCE: 28

```
cgcccccacc gcacgcatgg atcgcgccac gccgcgcgtt tgcggccgcc gcggcgtatc     60

ccaagcggcg gtggaagctg cgccgtcctc ctcccgcgcg cgccgccgcg ataaggcgcc    120

ggccgttgtc atggaccttg gcgacgacga ctgcggcggt ggcggggcca ggaagacggt    180

tggtggcgct gcaggtaggt gcgagggatc cacgaaggct ccttcgccta tgctgccgcc    240

gatgatggtg ccggcgggag cggtggcgct gcggacacga tcgaggaggc gggcgatgct    300

ggcggcggca gtggtggaag aggcgccaac gaagaagaag aagaaggaag gagcgatccc    360

agatgccgcg gaggcaaccc gtggccacgg gagcaaggcc gctgcgacct cgatggcgac    420

gtcgagccat aagcggcgcg ctgggacctc gaggtcgacg tcgagagata agcggcgcgc    480

gcgctcggga cgtgcctcgg agccagctcg cgtgggccgc gcgcgcaagc gcaaaaggaa    540

cgagttggag gcccccgctc ggagagaacg tgtgaaggcg ccatgtgtca gtgaaagtga    600

tgacaacagc gggcgaggcg atgacgcttc tcatgacggg gatgcggagc ctcgcggcgg    660

ggtcgccatt ggcactgatc tggttaacgg ggaccatccg gcagctaaag gtgaggatca    720

tattaagaga agagtgctgt gaatttgaat gatgacttgg tctcatgtaa tgcagaggta    780

gtggaaggtg ctggtgacga ggacacaggg gacggaggga acagtggcct ggcatcgact    840

gctgatgtgg ttgctgagga gatggcaccc tttgaagatg actacgatga tgagatgttg    900

gaggagcagc ttgttggaga tgtgattcgt gcttacagta atggcagaaa cttagattca    960

gatggagtgg attgggaggc agaggatgag atggagttca atgacgatgc tgacaatagt   1020

gattttatgg atgatgctga cgatagtgat tttatggatg atgcttatga aggtggcaat   1080
```

```
tccaaaccaa ttcaaaatca tgctaagttg gaaatacaag actgggtgaa ccagaaagtt   1140
gttttgagtg gagggaggtg tgaggtgagg ggcgaggggg atctggagga agaattgggt   1200
gtgggaaagg aagcagatga ggaggacgtg gaaccaaaga gtgaagcagc tccaggttct   1260
gataaaaggg tcttgcagtt agaaatccta ggttccgatg aggaaatcaa ggtgcttgaa   1320
aatatgagta gtgccccatc caggaaggcg tcagttcaat cgaagttacc aactattcca   1380
tcttgtgttg catggagaac ccgatcatca tggggggtaa atcaagatag actatcgtac   1440
gatacatatt ttgaggaatt atctgatgag ccaaaagagg atgatgatga tacagaggtg   1500
gaacttgatg aagttgagga tgacaacaat gacgatgaca gtagtgatgc ttatgataaa   1560
gatgacgaag agaaggagga agaggaagaa gaggctgaaa gaagaaaact taataacagg   1620
atttgcacat ccgatgaaga catgatcaat attactgttc ctacatcaag atatgatatg   1680
tttaagaaaa aaaattcctc aagatatgat attgagtggg tggaggatga agatgcaagt   1740
gttgatatgt tacagccagt ttcctttaag aaagatagca gctggaagcc tgtggctgtt   1800
ggcaacgaca catttactga gcaacaaaag cgatcacgat ttacttggga gcttgagagg   1860
aggaaaaagc ttaagcttga gatgaagaca aatcctttgc atgagcggga tttggactca   1920
gatccgaact catcaggttc tgaccagatc agaaagtatg gtttcaaaag tgatgggagt   1980
cataaagttg ataggaaaaa gaagcataca tcgcccaaat cgggcaagaa acccagcagc   2040
gcaatcatac taaagcggca gtctcttttg aagcttttgg tagataaaat gagtggtgat   2100
aaaagtttag catcttttcc atttgatcag aatcctcagc ttcagtttat tttcaaagaa   2160
atgcatccat tggtattttc atttggagat gaagatctag tagcagctga caggccagag   2220
caagatgttg gattggatat gttatgggct gactttgact ttgctttaga gtctgagaat   2280
atcggtactt attatgatga tgaggtacat tcagtactgg ttttcatttt atttttatct   2340
atcaaaacac atgcaggtat aaatatgtgt ggtttattta tttgaacact gactctacaa   2400
ctagaactat ggtaaaatta acaatgtcca actggagatg cactaccatg ttattctcag   2460
caaaaagttt gtcaatggcg acaaacgcaa aaagtttgat gaaacaatct cgatcaaacc   2520
aaaaaaactc tcattattca ccatctggca caagggcaaa gatgcaggag atgcccctct   2580
agggagcaga actccagcta tttttggaga tgcaccatca aacacatatc agctttgtca   2640
tttccaaatt gcccatgctc caagggtgat gatcgaatta agcccatttt gttcctcacc   2700
attttttttca acggaccttg tgaaacctaa ccatcaaccc ttgcttctcc ccttgccgat   2760
cattcatcaa aggaaacatc atctatctgt ggaggacctg caggctgcag cagtctaaac   2820
cagaattctc atgcaaaaac acacaatgtg agcaggtgat tgatcatctc agcttgatca   2880
caaagagcac agcaggtagg gtgcagaaga ctcatcatgc atgctgatcg gcagtccatt   2940
acctattttg agtaagtaac cacaaaagaa ccaacacttc ctgggcccca agattttcaa   3000
attctttccc aagacccaag aggacagaac catgaaataa acccttatca acagacttgc   3060
ctcaatcatc tacatctatc gttaacataa ctaacaagag aagaaataaa ccatttgagc   3120
tcactttgat agtgcaacac ttctgtgaac aatatgtgca tgtgaaatgt agcctccttt   3180
tctcagaatg catatatctg tggtgtttgt caagggcctc acactgctgt cgtgtccata   3240
aagaaagcac aggaatcaac aatccttctt cgggaacact attgaagcta gaacccagaa   3300
atgtacagaa aaaactatta gggcgtggaa attctttctg cattttcttc agtttgatct   3360
ggctctattg tttctcagat catgtctacg tcatggtagt ttttttttat cgaatgcgca   3420
ggagagatgc acatcattat attaagagat gaaaaggtcc aaaatagacc agcacaagat   3480
```

```
agtagaaaag gccctttatg gtggccaaaa agtaagatac agaaaatgat ccattaaatc   3540

aatcatacta taaatccgac cgaagagggt cggcaaggta gtttgcagct aatgtgcagg   3600

aaacgtcgtt tcccagaata gagtaacttt gtaaacatta gaaatgtttt ttttcaggtc   3660

aagaaatcta gttcacttaa aggagttact atagaatagt ttataaccat tatattaaga   3720

agagatgaaa aggtccaaaa tagaccagca caagatagta caaaaggccc tttatggcgg   3780

agtaagatac agaaaatgat ccattaaatc aatcctacta taaatccgac cgaagagggg   3840

cagcaaggta gtttgcagct aatgtgcagg aaacgtcgtt tcccagaata gagtaacttt   3900

gtaaacatta gaaatgtttt tttaggtcaa gaactctagt tcacttaaag gagttactat   3960

agaatagttt ataaccatta aggggcaatt cagatagcct cagaaggtca agaaaacttt   4020

atcatagcct gtgtgaatgt ttagacaaaa aggaagcaga aatgtttgtt ctttgtcaaa   4080

agtttcatca tcagtgtgtt tcatttaatg atttcctttt gtcccaacat taatgactca   4140

gttacatgtt gtttttgcga atggaatttt ctaacttggc aatgttactc aaacatatgt   4200

agtattctgc atatctgata ccacaggttg attcctactc ttaattcggc aatcaacata   4260

aatagtttca tcttttagaa actagacacc ccctactgct ttcatgtaaa agttatatag   4320

catttcaagg tcgtgcgtcc atgatatact actcgatttt taatgtttat tttcttgaat   4380

gcaagagttt gtaccattgc agatactttg atttgccact gtgagaatga ctaaatgaac   4440

ttattagctt atgttgtatt gtagtgtcaa gaaggcaatc aactagattt ttctcttgcc   4500

tcagtaacac cctgttctcg tgggaagcat gaatttgtta ttgatgatca aatagggatc   4560

agatgcaaat actgttcgtt ggtaaacctg gagatcaaat tcatgtttcc atcactggta   4620

agctttatta tggtcataaa tcatgacatc tattctacat aaatttggtc atttaagtca   4680

tcattttctt ttaggtgtca gtgtttggcg agaaatcagc atggccaaat gacaaaggcg   4740

tgaagaatac actgatgttt catgatcttt atgaacaagg agtcaatgac actgaacaat   4800

ctcaagatat tcatcaatat ggaacggtgt ggaatcttat tccaggggtc atcagtacta   4860

tgtatgagca tcagcgtgaa gcatttgaat ttatgtggac aaatttagtt ggtgatatta   4920

gacttgatga gataaagcat ggagcaaaac ctgatgttgt tggtggatgt gttatctgtc   4980

atgctcctgg aacaggaaag acacgattag ctattgtatt tatccagaca tacatgaaag   5040

tgtttccaga ctgtcggcca gtgattattg caccacgtgg tatgctcttt gcttgggatg   5100

aggaatttaa gaaatggaat gttgatgttc cttttcatat actaaacaca actgattaca   5160

ctggaaaaga ggaccgggac atatgcaagt taataaagaa agaacatagg acagaaaagt   5220

tgacaagact agtcaaactg ctttcatgga acaaaggcca tggtattctt ggaataagtt   5280

atggtctgta cacaaaactg acctctgaaa aacctggctg cacagaagaa aacaaagtaa   5340

gaagcattct tcttgataac cctggcttac ttgttcttga tgaaggacat acacctagga   5400

atgagcgcag tgttatgtgg aaaactctag gaaatgtgaa aactgagaag cgtataattt   5460

tatctagaac tccttttcag aacaattttc ttgagcttta caacattctt tgtctggtaa   5520

ggcctagatt tggtgaaatg tttttgacga agtcaagagt aggtcgaaga cattatgtct   5580

caaaaaagca aaaggataag ttttctgata aatatgaaaa gggtgtttgg gcatcactga   5640

ctagcaatgt aactgatgat aatgcggaga aagtaagatc aatattgaaa ccatttgttc   5700

atatacataa tggcaatatt cttcgaactc ttccaggact cagggagagt gtaattattt   5760

tgaagcctct tccccttcaa aagagtatca ttaaaaaggt ggaaaacatt ggttctggta   5820

acaacttcga acatgaatat gtcatttctt tagcttctac acacccttcc cttgtaaccg   5880
```

```
ccattaacat gtctgaggag gaagcttcac ttattgataa acctatgctt gctaaagtga   5940

gatcaaatcc atatgaaggg gtaaaaacaa gatttgtgat cgaagttgtt cgtttgtctg   6000

aagcattaag agagaaggtt ttgattttta gccaatttat tcagcctcta gagttgatta   6060

aagagcatct tcgcaagttc ttcaaatgga gagaagggaa agaaattctt caaatggatg   6120

gaaagatcct tccaagatat cgccaggctt ccattgaagc cttcaataat ccaaataatg   6180

attccagggt gttacttgca tctacaagag catgctgtga agggattagc ttgacaggtg   6240

cttcaagaat tgtgcttcta gatgttgttt ggaacccagc tgttggaagg caagccatca   6300

gcagagcatt taggataggt cagaagaaat ttgtatatac atataatttg ataacttatg   6360

gaacaggtga aggtgacaaa tatgataggc aagcagaaaa ggatcactta tccaagttgg   6420

tcttctctac agaagacgag ttcaataatg ttaggaacat gttatctaaa gctgaaatgg   6480

agcactgttc taagtttatc tcagaagata aagttttgga ggagatgact tcccacgatc   6540

aacttaaagg aatgtttttg aagatccatt atccaccaac tgagtcaaac attgtctata   6600

gttacaatca aattgctact gagtgaagtc ggtggtaata gtcagcacca gattgtttgt   6660

ctatatctat ggtatgctca aaatttctga cttcttcgta tagatgctgt agctttatat   6720

tagttctgtt a                                                        6731
```

<210> SEQ ID NO 29
<211> LENGTH: 1435
<212> TYPE: PRT
<213> ORGANISM: Zea mays

<400> SEQUENCE: 29

```
Met Asp Arg Ala Thr Pro Arg Val Cys Gly Arg Arg Gly Val Ser Gln
 1               5                  10                  15

Ala Ala Val Glu Ala Ala Pro Ser Ser Ser Arg Ala Arg Arg Arg Asp
            20                  25                  30

Lys Ala Pro Ala Val Val Met Asp Leu Gly Asp Asp Asp Cys Gly Gly
        35                  40                  45

Gly Gly Ala Arg Lys Thr Val Gly Gly Ala Ala Gly Arg Cys Glu Gly
    50                  55                  60

Ser Thr Lys Ala Pro Ser Pro Met Leu Pro Pro Met Met Val Pro Ala
65                  70                  75                  80

Gly Ala Val Ala Leu Arg Thr Arg Ser Arg Arg Arg Ala Met Leu Ala
                85                  90                  95

Ala Ala Val Val Glu Glu Ala Pro Thr Lys Lys Lys Lys Lys Glu Gly
            100                 105                 110

Ala Ile Pro Asp Ala Ala Glu Ala Thr Arg Gly His Gly Ser Lys Ala
        115                 120                 125

Ala Ala Thr Ser Met Ala Thr Ser Ser His Lys Arg Arg Ala Gly Thr
    130                 135                 140

Ser Arg Ser Thr Ser Arg Asp Lys Arg Arg Ala Arg Ser Gly Arg Ala
145                 150                 155                 160

Ser Glu Pro Ala Arg Val Gly Arg Ala Arg Lys Arg Lys Arg Asn Glu
                165                 170                 175

Leu Glu Ala Pro Ala Arg Arg Glu Arg Val Lys Ala Pro Cys Val Ser
            180                 185                 190

Glu Ser Asp Asp Asn Ser Gly Arg Gly Asp Asp Ala Ser His Asp Gly
        195                 200                 205

Asp Ala Glu Pro Arg Gly Gly Val Ala Ile Gly Thr Asp Leu Val Asn
    210                 215                 220
```

```
Gly Asp His Pro Ala Ala Lys Glu Val Val Glu Gly Ala Gly Asp Glu
225                 230                 235                 240

Asp Thr Gly Asp Gly Gly Asn Ser Gly Leu Ala Ser Thr Ala Asp Val
                245                 250                 255

Val Ala Glu Glu Met Ala Pro Phe Glu Asp Asp Tyr Asp Asp Glu Met
            260                 265                 270

Leu Glu Glu Gln Leu Val Gly Asp Val Ile Arg Ala Tyr Ser Asn Gly
        275                 280                 285

Arg Asn Leu Asp Ser Asp Gly Val Asp Trp Glu Ala Glu Asp Glu Met
    290                 295                 300

Glu Phe Asn Asp Asp Ala Asp Asn Ser Asp Phe Met Asp Asp Ala Asp
305                 310                 315                 320

Asp Ser Asp Phe Met Asp Asp Ala Tyr Glu Gly Gly Asn Ser Lys Pro
                325                 330                 335

Ile Gln Asn His Ala Lys Leu Glu Ile Gln Asp Trp Val Asn Gln Lys
            340                 345                 350

Val Val Leu Ser Gly Gly Arg Cys Glu Val Arg Gly Glu Gly Asp Leu
        355                 360                 365

Glu Glu Glu Leu Gly Val Gly Lys Glu Ala Asp Glu Glu Asp Val Glu
    370                 375                 380

Pro Lys Ser Glu Ala Ala Pro Gly Ser Asp Lys Arg Val Leu Gln Leu
385                 390                 395                 400

Glu Ile Leu Gly Ser Asp Glu Glu Ile Lys Val Leu Glu Asn Met Ser
                405                 410                 415

Ser Ala Pro Ser Arg Lys Ala Ser Val Gln Ser Lys Leu Pro Thr Ile
            420                 425                 430

Pro Ser Cys Val Ala Trp Arg Thr Arg Ser Ser Trp Gly Val Asn Gln
        435                 440                 445

Asp Arg Leu Ser Tyr Asp Thr Tyr Phe Glu Glu Leu Ser Asp Glu Pro
    450                 455                 460

Lys Glu Asp Asp Asp Asp Thr Glu Val Glu Leu Asp Glu Val Glu Asp
465                 470                 475                 480

Asp Asn Asn Asp Asp Asp Ser Ser Asp Ala Tyr Asp Lys Asp Asp Glu
                485                 490                 495

Glu Lys Glu Glu Glu Glu Glu Glu Ala Glu Arg Arg Lys Leu Asn Asn
            500                 505                 510

Arg Ile Cys Thr Ser Asp Glu Asp Met Ile Asn Ile Thr Val Pro Thr
        515                 520                 525

Ser Arg Tyr Asp Met Phe Lys Lys Lys Asn Ser Ser Arg Tyr Asp Ile
    530                 535                 540

Glu Trp Val Glu Asp Glu Asp Ala Ser Val Asp Met Leu Gln Pro Val
545                 550                 555                 560

Ser Phe Lys Lys Asp Ser Ser Trp Lys Pro Val Ala Val Gly Asn Asp
                565                 570                 575

Thr Phe Thr Glu Gln Gln Lys Arg Ser Arg Phe Thr Trp Glu Leu Glu
            580                 585                 590

Arg Arg Lys Lys Leu Lys Leu Glu Met Lys Thr Asn Pro Leu His Glu
        595                 600                 605

Arg Asp Leu Asp Ser Asp Pro Asn Ser Ser Gly Ser Asp Gln Ile Arg
    610                 615                 620

Lys Tyr Gly Phe Lys Ser Asp Gly Ser His Lys Val Asp Arg Lys Lys
625                 630                 635                 640

Lys His Thr Ser Pro Lys Ser Gly Lys Lys Pro Ser Ser Ala Ile Ile
```

```
                645                 650                 655

Leu Lys Arg Gln Ser Leu Leu Lys Leu Leu Val Asp Lys Met Ser Gly
            660                 665                 670

Asp Lys Ser Leu Ala Ser Phe Pro Phe Asp Gln Asn Pro Gln Leu Gln
        675                 680                 685

Phe Ile Phe Lys Glu Met His Pro Leu Val Phe Ser Phe Gly Asp Glu
    690                 695                 700

Asp Leu Val Ala Ala Asp Arg Pro Glu Gln Asp Val Gly Leu Asp Met
705                 710                 715                 720

Leu Trp Ala Asp Phe Asp Phe Ala Leu Glu Ser Glu Asn Ile Gly Thr
                725                 730                 735

Tyr Tyr Asp Asp Glu Cys Gln Glu Gly Asn Gln Leu Asp Phe Ser Leu
            740                 745                 750

Ala Ser Val Thr Pro Cys Ser Arg Gly Lys His Glu Phe Val Ile Asp
        755                 760                 765

Asp Gln Ile Gly Ile Arg Cys Lys Tyr Cys Ser Leu Val Asn Leu Glu
    770                 775                 780

Ile Lys Phe Met Phe Pro Ser Leu Val Ser Val Phe Gly Glu Lys Ser
785                 790                 795                 800

Ala Trp Pro Asn Asp Lys Gly Val Lys Asn Thr Leu Met Phe His Asp
                805                 810                 815

Leu Tyr Glu Gln Gly Val Asn Asp Thr Glu Gln Ser Gln Asp Ile His
            820                 825                 830

Gln Tyr Gly Thr Val Trp Asn Leu Ile Pro Gly Val Ile Ser Thr Met
        835                 840                 845

Tyr Glu His Gln Arg Glu Ala Phe Glu Phe Met Trp Thr Asn Leu Val
    850                 855                 860

Gly Asp Ile Arg Leu Asp Glu Ile Lys His Gly Ala Lys Pro Asp Val
865                 870                 875                 880

Val Gly Gly Cys Val Ile Cys His Ala Pro Gly Thr Gly Lys Thr Arg
                885                 890                 895

Leu Ala Ile Val Phe Ile Gln Thr Tyr Met Lys Val Phe Pro Asp Cys
            900                 905                 910

Arg Pro Val Ile Ile Ala Pro Arg Gly Met Leu Phe Ala Trp Asp Glu
        915                 920                 925

Glu Phe Lys Lys Trp Asn Val Asp Val Pro Phe His Ile Leu Asn Thr
    930                 935                 940

Thr Asp Tyr Thr Gly Lys Glu Asp Arg Asp Ile Cys Lys Leu Ile Lys
945                 950                 955                 960

Lys Glu His Arg Thr Glu Lys Leu Thr Arg Leu Val Lys Leu Leu Ser
                965                 970                 975

Trp Asn Lys Gly His Gly Ile Leu Gly Ile Ser Tyr Gly Leu Tyr Thr
            980                 985                 990

Lys Leu Thr Ser Glu Lys Pro Gly Cys Thr Glu Glu Asn Lys Val Arg
        995                 1000                1005

Ser Ile Leu Leu Asp Asn Pro Gly Leu Leu Val Leu Asp Glu Gly His
    1010                1015                1020

Thr Pro Arg Asn Glu Arg Ser Val Met Trp Lys Thr Leu Gly Asn Val
1025                1030                1035                1040

Lys Thr Glu Lys Arg Ile Ile Leu Ser Arg Thr Pro Phe Gln Asn Asn
                1045                1050                1055

Phe Leu Glu Leu Tyr Asn Ile Leu Cys Leu Val Arg Pro Arg Phe Gly
            1060                1065                1070
```

```
Glu Met Phe Leu Thr Lys Ser Arg Val Gly Arg Arg His Tyr Val Ser
        1075                1080                1085

Lys Lys Gln Lys Asp Lys Phe Ser Asp Lys Tyr Glu Lys Gly Val Trp
    1090                1095                1100

Ala Ser Leu Thr Ser Asn Val Thr Asp Asp Asn Ala Glu Lys Val Arg
1105                1110                1115                1120

Ser Ile Leu Lys Pro Phe Val His Ile His Asn Gly Asn Ile Leu Arg
                1125                1130                1135

Thr Leu Pro Gly Leu Arg Glu Ser Val Ile Ile Leu Lys Pro Leu Pro
            1140                1145                1150

Leu Gln Lys Ser Ile Ile Lys Lys Val Glu Asn Ile Gly Ser Gly Asn
        1155                1160                1165

Asn Phe Glu His Glu Tyr Val Ile Ser Leu Ala Ser Thr His Pro Ser
    1170                1175                1180

Leu Val Thr Ala Ile Asn Met Ser Glu Glu Glu Ala Ser Leu Ile Asp
1185                1190                1195                1200

Lys Pro Met Leu Ala Lys Val Arg Ser Asn Pro Tyr Glu Gly Val Lys
                1205                1210                1215

Thr Arg Phe Val Ile Glu Val Val Arg Leu Ser Glu Ala Leu Arg Glu
            1220                1225                1230

Lys Val Leu Ile Phe Ser Gln Phe Ile Gln Pro Leu Glu Leu Ile Lys
        1235                1240                1245

Glu His Leu Arg Lys Phe Phe Lys Trp Arg Glu Gly Lys Glu Ile Leu
    1250                1255                1260

Gln Met Asp Gly Lys Ile Leu Pro Arg Tyr Arg Gln Ala Ser Ile Glu
1265                1270                1275                1280

Ala Phe Asn Asn Pro Asn Asn Asp Ser Arg Val Leu Leu Ala Ser Thr
                1285                1290                1295

Arg Ala Cys Cys Glu Gly Ile Ser Leu Thr Gly Ala Ser Arg Ile Val
            1300                1305                1310

Leu Leu Asp Val Val Trp Asn Pro Ala Val Gly Arg Gln Ala Ile Ser
        1315                1320                1325

Arg Ala Phe Arg Ile Gly Gln Lys Lys Phe Val Tyr Thr Tyr Asn Leu
    1330                1335                1340

Ile Thr Tyr Gly Thr Gly Glu Gly Asp Lys Tyr Asp Arg Gln Ala Glu
1345                1350                1355                1360

Lys Asp His Leu Ser Lys Leu Val Phe Ser Thr Glu Asp Glu Phe Asn
                1365                1370                1375

Asn Val Arg Asn Met Leu Ser Lys Ala Glu Met Glu His Cys Ser Lys
            1380                1385                1390

Phe Ile Ser Glu Asp Lys Val Leu Glu Glu Met Thr Ser His Asp Gln
        1395                1400                1405

Leu Lys Gly Met Phe Leu Lys Ile His Tyr Pro Pro Thr Glu Ser Asn
    1410                1415                1420

Ile Val Tyr Ser Tyr Asn Gln Ile Ala Thr Glu
1425                1430                1435
```

<210> SEQ ID NO 30
<211> LENGTH: 20
<212> TYPE: DNA
<213> ORGANISM: Artificial Sequence
<220> FEATURE:
<223> OTHER INFORMATION: Synthesized Construct

<400> SEQUENCE: 30
gaagagttgg gtgtgggaaa 20

<210> SEQ ID NO 31
<211> LENGTH: 20
<212> TYPE: DNA
<213> ORGANISM: Artificial Sequence
<220> FEATURE:
<223> OTHER INFORMATION: Synthesized Construct

<400> SEQUENCE: 31
aacatcttgc tctggcctgt 20

<210> SEQ ID NO 32
<211> LENGTH: 20
<212> TYPE: DNA
<213> ORGANISM: Artificial Sequence
<220> FEATURE:
<223> OTHER INFORMATION: Synthesized Construct

<400> SEQUENCE: 32
gtgtcagtgt ttgccgagaa 20

<210> SEQ ID NO 33
<211> LENGTH: 28
<212> TYPE: DNA
<213> ORGANISM: Artificial Sequence
<220> FEATURE:
<223> OTHER INFORMATION: Synthesized Construct

<400> SEQUENCE: 33
ctatagttac aatcaaattg ctactgag 28

<210> SEQ ID NO 34
<211> LENGTH: 21
<212> TYPE: DNA
<213> ORGANISM: Artificial Sequence
<220> FEATURE:
<223> OTHER INFORMATION: Synthesized Construct

<400> SEQUENCE: 34
gttgcagcaa cagaatctag c 21

<210> SEQ ID NO 35
<211> LENGTH: 20
<212> TYPE: DNA
<213> ORGANISM: Artificial Sequence
<220> FEATURE:
<223> OTHER INFORMATION: Synthesized Construct

<400> SEQUENCE: 35
aagcatacat cgcccaaatc 20

<210> SEQ ID NO 36
<211> LENGTH: 20
<212> TYPE: DNA
<213> ORGANISM: Artificial Sequence
<220> FEATURE:
<223> OTHER INFORMATION: Synthesized Construct

<400> SEQUENCE: 36
cacgctgatg ctcatacata 20

<210> SEQ ID NO 37
<211> LENGTH: 20
<212> TYPE: DNA
<213> ORGANISM: Artificial Sequence
<220> FEATURE:
<223> OTHER INFORMATION: Synthesized Construct

<400> SEQUENCE: 37
cccaatcatg caactcctct 20

<210> SEQ ID NO 38
<211> LENGTH: 23
<212> TYPE: DNA
<213> ORGANISM: Artificial Sequence
<220> FEATURE:
<223> OTHER INFORMATION: Synthesized Construct

<400> SEQUENCE: 38
ccataactta ttccaagaat acc 23

<210> SEQ ID NO 39
<211> LENGTH: 27
<212> TYPE: DNA
<213> ORGANISM: Artificial Sequence
<220> FEATURE:
<223> OTHER INFORMATION: Synthesized Construct

<400> SEQUENCE: 39
gtcgtttccc agaatagagt aactttg 27

<210> SEQ ID NO 40
<211> LENGTH: 28
<212> TYPE: DNA
<213> ORGANISM: Artificial Sequence
<220> FEATURE:
<223> OTHER INFORMATION: Synthesized Construct

<400> SEQUENCE: 40
gatatgcaga atactacata tgtttgag 28

<210> SEQ ID NO 41
<211> LENGTH: 20
<212> TYPE: DNA
<213> ORGANISM: Artificial Sequence
<220> FEATURE:
<223> OTHER INFORMATION: Synthesized Construct

<400> SEQUENCE: 41
gcatcttcgc aagttcttca 20

<210> SEQ ID NO 42
<211> LENGTH: 20
<212> TYPE: DNA
<213> ORGANISM: Artificial Sequence
<220> FEATURE:
<223> OTHER INFORMATION: Synthesized Construct

<400> SEQUENCE: 42
tcgtgggaag tcatctcctc 20

<210> SEQ ID NO 43
<211> LENGTH: 20
<212> TYPE: DNA
<213> ORGANISM: Artificial Sequence
<220> FEATURE:
<223> OTHER INFORMATION: Synthesized Construct

<400> SEQUENCE: 43
atgagtagtg ccccatccag 20

<210> SEQ ID NO 44
<211> LENGTH: 21

```
<212> TYPE: DNA
<213> ORGANISM: Artificial Sequence
<220> FEATURE:
<223> OTHER INFORMATION: Synthesized Construct

<400> SEQUENCE: 44

tcagcctctt cttcctcttc c                                               21


<210> SEQ ID NO 45
<211> LENGTH: 19
<212> TYPE: DNA
<213> ORGANISM: Artificial Sequence
<220> FEATURE:
<223> OTHER INFORMATION: Synthesized Construct

<400> SEQUENCE: 45

gatgacgctt ctcatgacg                                                  19


<210> SEQ ID NO 46
<211> LENGTH: 23
<212> TYPE: DNA
<213> ORGANISM: Artificial Sequence
<220> FEATURE:
<223> OTHER INFORMATION: Synthesized Construct

<400> SEQUENCE: 46

atcatcgtag tcatcttcaa agg                                             23
```